US012723271B1

(12) United States Patent
Palluk et al.

(10) Patent No.: US 12,723,271 B1
(45) Date of Patent: Sep. 1, 2026

(54) MODIFIED NUCLEOTIDES AND NUCLEOTIDE CONJUGATES FOR POLYNUCLEOTIDE SYNTHESIS

(71) Applicant: Ansa Biotechnologies, Inc., Emeryville, CA (US)

(72) Inventors: Sebastian Palluk, Oakland, CA (US); Daniel Arlow, San Francisco, CA (US); Jeffrey George Bertram, Montebello, CA (US); Eric Estrin, Oakland, CA (US); Uwe Theo Bornscheuer, Greifswald (DE); Nico Dennis Fessner, Greifswald (DE); Christoffel Petrus Stephanus Badenhorst, Greifswald (DE); Jared Ellefson, El Cerrito, CA (US)

(73) Assignee: Ansa Biotechnologies, Inc., Emeryville, CA (US)

( * ) Notice: Subject to any disclaimer, the term of this patent is extended or adjusted under 35 U.S.C. 154(b) by 804 days.

(21) Appl. No.: 17/953,273

(22) Filed: Sep. 26, 2022

Related U.S. Application Data

(60) Provisional application No. 63/248,166, filed on Sep. 24, 2021.

(51) Int. Cl.
*C12P 19/34* (2006.01)
*C12Q 1/68* (2018.01)

(52) U.S. Cl.
CPC ................ *C12P 19/34* (2013.01); *C12Q 1/68* (2013.01); *C12Q 2525/186* (2013.01)

(58) Field of Classification Search
CPC ..... C12P 19/34; C12Q 1/68; C12Q 2525/186; C07H 21/00
See application file for complete search history.

(56) References Cited

U.S. PATENT DOCUMENTS

| | | | |
|---|---|---|---|
| 11,254,961 | B2 | 2/2022 | Arlow et al. |
| 11,624,079 | B2 | 4/2023 | Arlow et al. |
| 11,732,283 | B2 | 8/2023 | Arlow et al. |
| 2007/0172860 | A1 | 7/2007 | Hardin et al. |
| 2014/0308730 | A1 | 10/2014 | Nikiforov et al. |
| 2015/0086981 | A1 | 3/2015 | Cherkasov et al. |
| 2019/0112627 | A1 | 4/2019 | Arlow et al. |
| 2019/0352327 | A1 | 11/2019 | Wu et al. |
| 2022/0023820 | A1 | 1/2022 | Strauss et al. |
| 2022/0205008 | A1 | 6/2022 | Arlow et al. |
| 2022/0251617 | A1 | 8/2022 | Arlow et al. |
| 2024/0401099 | A1 | 12/2024 | Arlow et al. |

FOREIGN PATENT DOCUMENTS

| | | | |
|---|---|---|---|
| CN | 101346472 | A | 1/2009 |
| JP | 2009519041 | A | 5/2009 |
| JP | 2010166918 | A | 8/2010 |
| WO | 2004092331 | A2 | 10/2004 |
| WO | 2006/079061 | A2 | 7/2006 |
| WO | 2007070542 | A2 | 6/2007 |
| WO | 2007070572 | A2 | 6/2007 |
| WO | 2014142981 | A1 | 9/2014 |
| WO | 2015124955 | A1 | 8/2015 |
| WO | 2017190018 | A1 | 11/2017 |
| WO | 2017223517 | A1 | 12/2017 |
| WO | 2024073349 | A2 | 4/2024 |

OTHER PUBLICATIONS

Pongracz et al. "Synthesis of a 25 base oligonucleotide containing a styrene oxide modification at the O6 position of 2'-deoxyguanosine at a defined site and incorporation studies of the similarly modified 2'-deoxy guanosine-5'-triphosphate" Carcinogenesis, vol. 15, No. 7, pp. 1371-1375, 1994. (Year: 1994).*

Pon et al. "Modification of guanine bases by nucleoside phosphoramidite reagents during the solid phase synthesis of oligonucleotides" Nucleic Acids Research, vol. 13, No. 18, 1985. (Year: 1985).*

Invitation to Pay Additional Fees for PCT/US2023/075020, mailed Mar. 7, 2024, 3 pages.

International Search Report and Written Opinion for PCT/US2023/075020, mailed Apr. 23, 2024, 15 pages.

Chica et al., Semi-rational approaches to engineering enzyme activity: combining the benefits of directed evoulution and rational design, Curr. Opin. Biotechnol. 16(4):378-84 (2005).

Singh et al., Protein Engineering Approaches in the Post-Genomic Era, Curr. Protein Pept. Sci., 18, 1-11 (2017).

Accession F6RGZ5. Jul. 27, 2011 (Year: 2011).

Bundy et al., Site-Specific Incorporation of p-Propargyloxyphenylalanine in a Cell-Free Environment for Direct Protein-Proteing Click Conjugation, Bioconjugate Chem, 21, 255-263 (2010).

Mccombs et al., Antibody Drug Conjugates: Design and Selection of Linker, Payload and Conjugation Chemistry, AAPS J. Mar. 2015; 17(2): 339-351. Published on line Jan. 22, 2015, (2015).

PCT/US2017/039120 International Search Report and Written Opinion of mailed Oct. 12, 2017, 10 pages.

* cited by examiner

*Primary Examiner* — Jezia Riley
(74) *Attorney, Agent, or Firm* — Goodwin Procter LLP

(57) ABSTRACT

Disclosed herein are improved methods for the de novo synthesis of nucleic acids by cyclic extension using a template-independent polymerase. Secondary structure formation in the nascent chain, which may inhibit extension reactions, is suppressed by the use of monomers with O-alkylated nucleobases that prevent Watson-Crick base pairing and/or other structures. After the synthesis is completed, the nucleobases can be converted back into native form by enzymatic removal of the alkyl groups.

12 Claims, 19 Drawing Sheets

Specification includes a Sequence Listing.

MODIFIED NUCLEOTIDES AND NUCLEOTIDE CONJUGATES FOR POLYNUCLEOTIDE SYNTHESIS

CROSS-REFERENCE TO RELATED APPLICATIONS

This application claims the benefit of U.S. Provisional Application No. 63/248,166, filed Sep. 24, 2021, the contents of which is incorporated by reference in its entirety.

SEQUENCE LISTING

The instant application contains a Sequence Listing which has been submitted electronically in XML file format and is hereby incorporated by reference in its entirety. Said XML copy, created on Mar. 16, 2026, is named ABB-005US-_SL.xml and is 34,707 bytes in size.

BACKGROUND

Standard de novo DNA synthesis performed today is based on the nucleoside phosphoramidite method (generally referred to as "chemical synthesis") in which a desired sequence is synthesized by stepwise coupling of blocked monomers. The reactions are performed in organic solvents using highly reactive activated monomers, and the conditions cause side reactions that damage the growing chain, limiting the yield of full-length product. The impurities produced can be difficult or impractical to separate from the desired oligonucleotide product, limiting the usefulness of the method for producing sequences longer than approximately 200 bases.

As an alternative, different enzymatic de novo DNA synthesis strategies using template-independent polymerases have more recently been developed, allowing an environmentally friendly synthesis of longer DNA molecules than with chemical synthesis. However, as the nucleic acid is being synthesized, it can base-pair with itself, inhibiting the extension reaction for a template-independent polymerase that has low activity on a duplex structure.

Elevation of temperature has been explored to reduce secondary structure (Barthel et al., Enhancing Terminal Deoxynucleotidyl Transferase Activity on Substrates with 3' Terminal Structures for Enzymatic De Novo DNA Synthesis, *Genes* 2020, 11(1), 102). However, elevated temperature induces damage to DNA (and quickly damages RNA), and secondary structure remains even in elevated temperatures suitable for synthesis. Synthesis reactions at elevated temperatures also require thermostable polymerases. Wild-type template independent polymerases such as Terminal deoxynucleotidyl Transferase (TdT) are not thermostable. Use of bases with exocyclic amines masked by acyl groups (DNA Script WO2021/018921A1) has been explored. However, N-acylation does not prevent Watson-Crick base pairing, and high efficiency de-acylation of the synthesized polynucleotides is challenging. Use of bases with exocyclic amines masked as azido groups has also been explored (Nuclera Nucleics PCT Publication WO2020/229831A1). However, the unmasking reagent (TCEP) causes DNA damage, and there are doubts about the stability of the azido modification.

What is needed, therefore, are improved reagents and methods for enzymatic nucleic acid synthesis that allow efficient synthesis with reduced inhibition from secondary structure formation, while resulting in a synthesized polynucleotide in which base pairing is regenerated to the behavior of naturally occurring polynucleotides.

SUMMARY OF THE INVENTION

The present disclosure includes a method of synthesizing a polynucleotide, comprising, providing a polynucleotide comprising one or more alkylated nucleobases; and removing one or more alkyl groups from said one or more alkylated nucleobases. In some embodiments, providing said polynucleotide comprises contacting a precursor polynucleotide with a polymerase and a nucleotide comprising said alkylated nucleobase; and adding said nucleotide to the 3' end of said precursor polynucleotide via said polymerase. In some embodiments, providing said polynucleotide comprises contacting a precursor polynucleotide with a conjugate comprising a nucleotide covalently linked to a polymerase via a linker, wherein said nucleotide comprises said alkylated nucleobase; and adding said nucleotide to the 3' end of said precursor polynucleotide via said polymerase.

In some embodiments, the linker is cleavable.

In some embodiments, the method of synthesizing a polynucleotide further comprises cleaving said cleavable linker after addition of said nucleotide to said precursor polynucleotide. In some embodiments, the method of synthesizing a polynucleotide further comprises repeating said contacting, adding, and optionally said cleaving steps one or more times.

In some embodiments, the polymerase is a template independent polymerase. In some embodiments, the polymerase is TdT.

In some embodiments, the nucleotide comprises a 2' or 3' modification.

In some embodiments, the removal of said one or more alkyl groups comprises contacting said polynucleotide with an enzyme capable of removing said one or more alkyl groups from said alkylated nucleobases.

In some embodiments, the enzyme is an alkyl transferase. In some embodiments, the alkyl transferase dis from EC 2.1.1.63. In some embodiments, the alkyl transferase is selected from an alkyl transferase listed in Table 1 or Table 2. In some embodiments, the alkyl transferase is O6-alkylguanine DNA alkyltransferase. In some embodiments, the alkyl transferase is AlkB.

In some embodiments, the method of synthesizing a polynucleotide comprises contacting said polynucleotide with two or more enzymes capable of removing said one or more alkyl groups from said alkylated nucleobases.

In some embodiments, the conjugate is represented by:

I

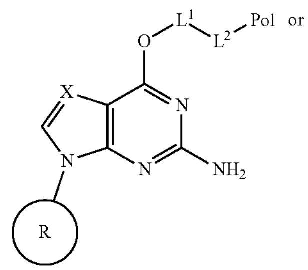

or

-continued

II

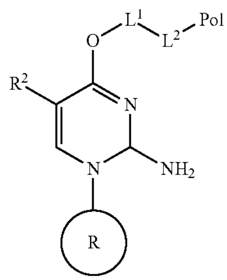

wherein $L^1$ is selected from the group consisting of an optionally substituted $C_{1-6}$ alkylene chain, an optionally substituted $C_{2-6}$ alkenylene chain, and an optionally substituted $C_{1-6}$ alkynylene chain, wherein 1-4 methylene units are optionally and independently replaced with —O—, —N($R^a$)—, —C(O)—, —S—, —S(O)—, —$S(O)_2$—, or phenylene;

$L^2$ is a cleavable linker;

X is —N═ or —C(H)═;

each $R^a$ is independently hydrogen or $C_{1-6}$ alkyl;

$R^2$ is hydrogen or methyl;

R is a ribose polyphosphate or deoxyribose polyphosphate; and

Pol is a polymerase.

In some embodiments, the conjugate is represented by

II-a

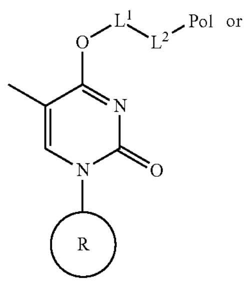

or

II-b

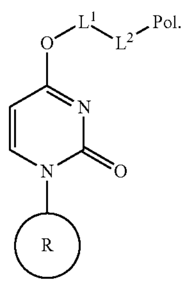

In some embodiments, $L^1$ is selected from the group consisting of:

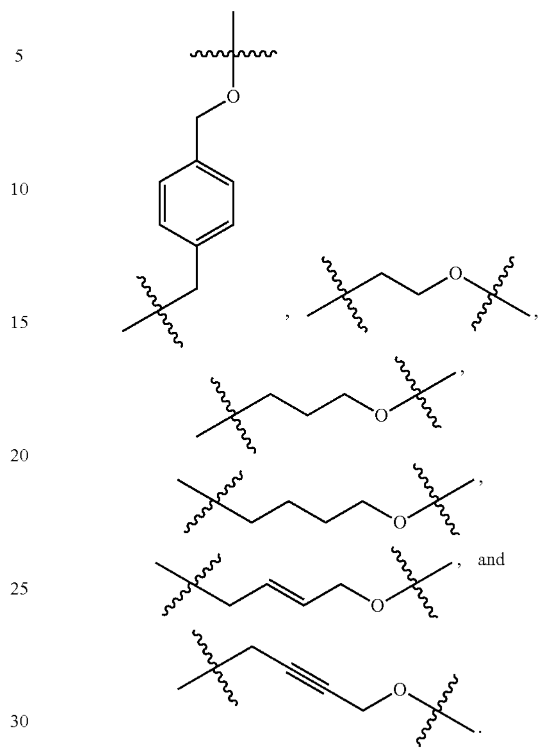

In some embodiments, the conjugate is selected from the group consisting of:

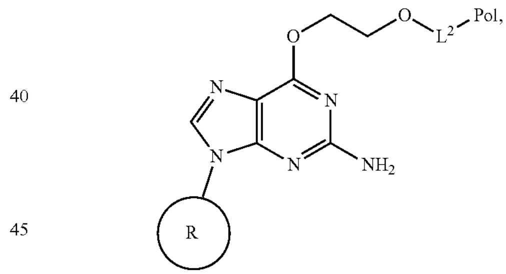

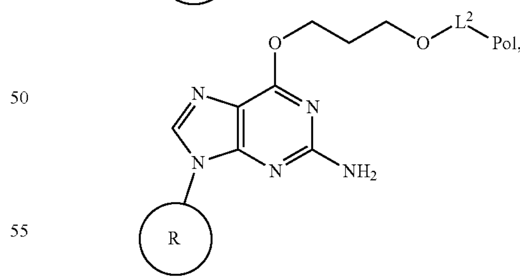

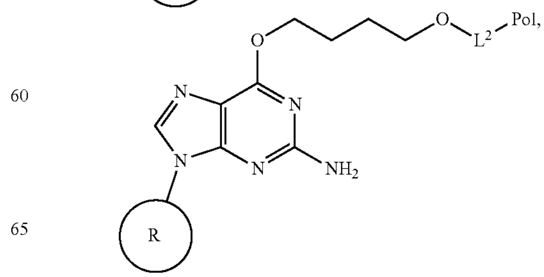

-continued
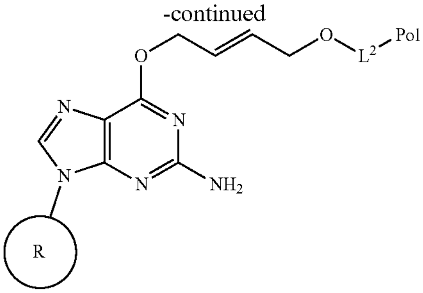
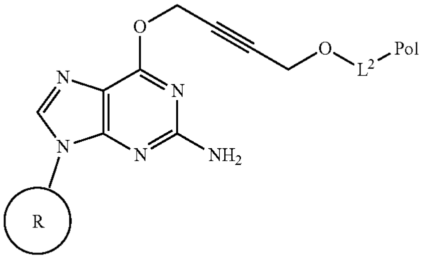
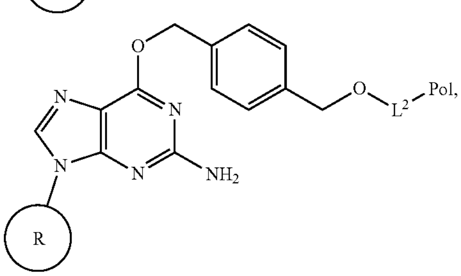
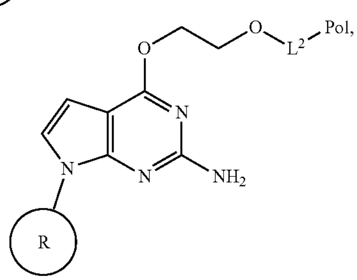
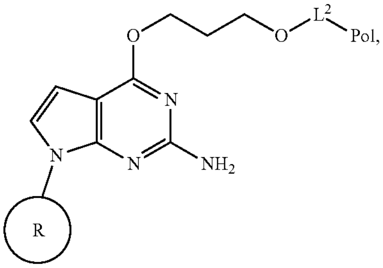
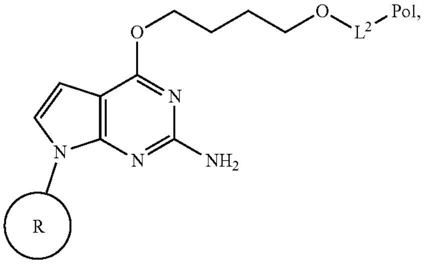
-continued
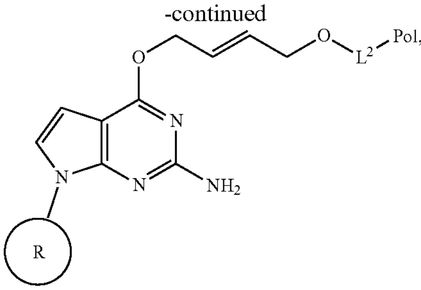
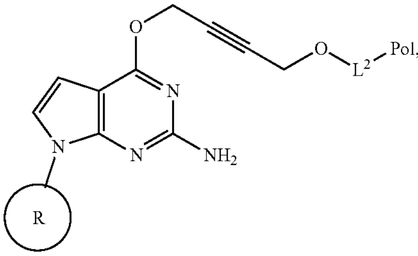
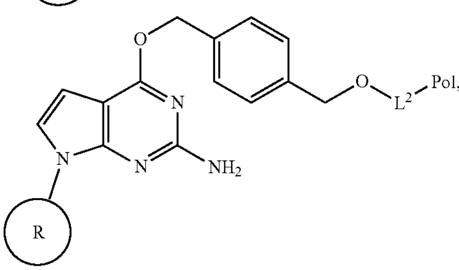
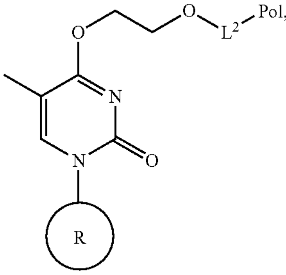
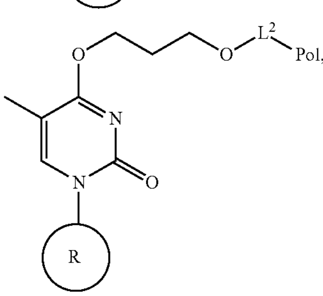
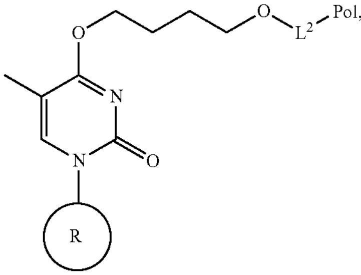

-continued

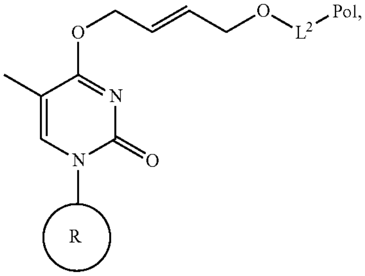

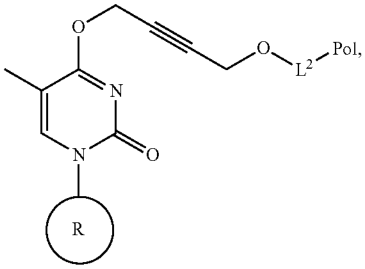

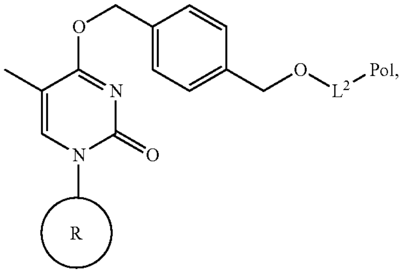

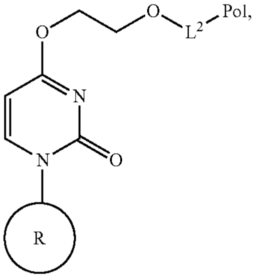

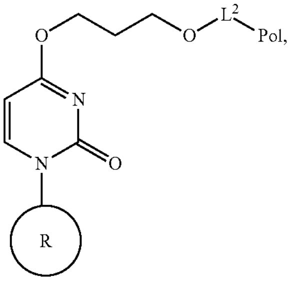

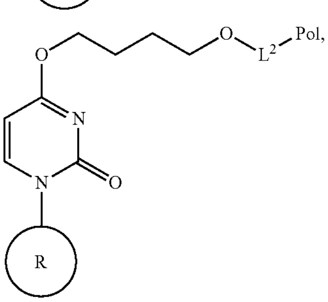

-continued

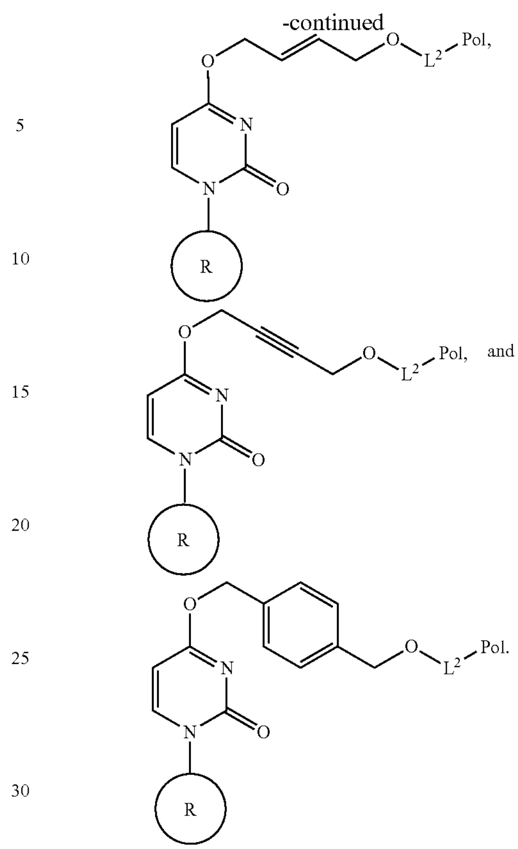

and

In some embodiments, the conjugate is represented by:

III

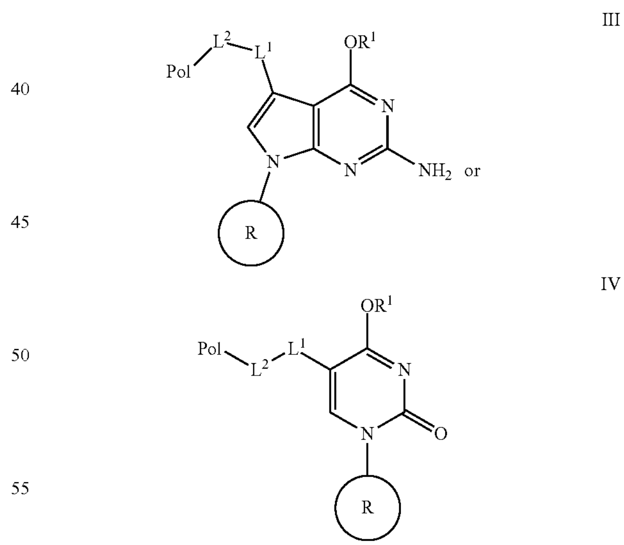

or

IV wherein $L^1$ is selected from the group consisting of an optionally substituted $C_{1-4}$ alkylene chain, wherein 1-2 methylene units is optionally and independently replaced with —O—, —N($R^a$)—, —C(O)—, —S—, —S(O)—, —S(O)$_2$—, or phenylene;

$L^2$ is a cleavable linker;

each $R^a$ is independently hydrogen or $C_{1-6}$ alkyl;

$R^1$ is $C_{1-6}$ alkyl, $C_{2-6}$ alkenyl, $C_{1-6}$ alkynyl, and $-(CH_2)_{0-3}Ph$, wherein $R^1$ is optionally substituted with 1-6 instances of $R^{1a}$;

each $R^{1a}$ is independently selected from halogen, $C_{1-6}$ alkyl, $-(CH_2)_{0-3}OR^{1b}$, $-NO_2$, $-N_3$, $-OPO_2OH$, and $-(CH_2)_{0-3}NHR^{1b}$; and each $R^{1b}$ is independently selected from hydrogen, $C_{1-6}$ alkyl, $-C(O)(C_{1-6}$ alkyl), $C_{1-6}$ haloalkyl, $-C(O)(C_{1-6}$ haloalkyl), and $-CH_2OAc$;

R is a ribose polyphosphate or deoxyribose polyphosphate; and

Pol is a polymerase.

In some embodiments, $R^1$ is $C_{1-3}$ alkyl. In some embodiments, $R^1$ is methyl.

In some embodiments, the conjugate is

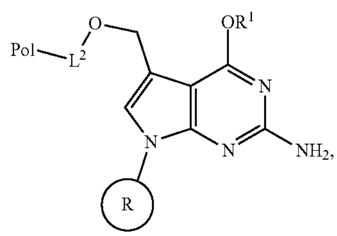

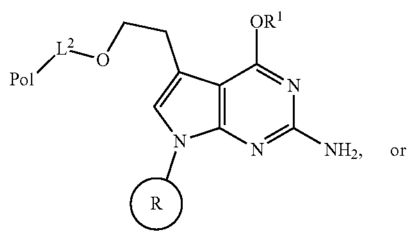

or

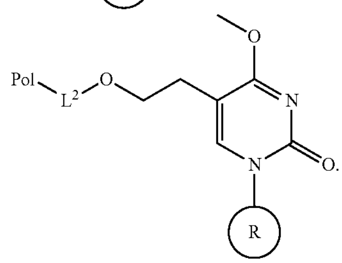

In some embodiments, the alkylated nucleobase in the polynucleotide is represented by:

V

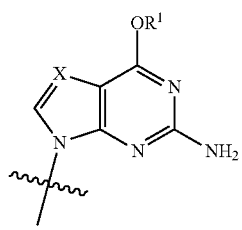

or

-continued

VI

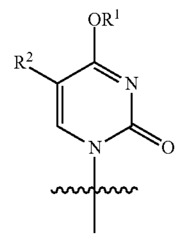

wherein

X is $-C(R^2)=$ or $-N=$;

$R^1$ is selected from the group consisting of $C_{1-6}$ alkyl, $C_{2-6}$ alkenyl, $C_{1-6}$ alkynyl, and $-(CH_2)_{0-3}Ph$, wherein $R^1$ is optionally substituted with 1-6 instances of $R^{1a}$;

each $R^{1a}$ is independently selected from halogen, $C_{1-6}$ alkyl, $-(CH_2)_{0-3}OR^{1b}$, $-NO_2$, $-N_3$, $-OPO_2OH$, and $-(CH_2)_{0-3}NHR^{1b}$; and each $R^{1b}$ is independently selected from hydrogen, $C_{1-6}$ alkyl, $-C(O)(C_{1-6}$ alkyl), $C_{1-6}$ haloalkyl, $-C(O)(C_{1-6}$ haloalkyl), and $-CH_2OAc$;

$R^2$ is selected from the group consisting of hydrogen, optionally substituted $C_{1-4}$ alkyl chain, wherein 1-2 methylene units is optionally and independently replaced with $-O-$, $-N(R^a)-$, $-C(O)-$, $-S-$, $-S(O)-$, $-S(O)_2-$, or phenylene, wherein $R^2$ is optionally substituted with 1-6 instances of $R^{2a}$;

each $R^{2a}$ is independently selected from halogen, $C_{1-6}$ alkyl, $-(CH_2)_{0-3}OR^{2b}$, $-NO_2$, $-N_3$, $-OPO_2OH$, and $-(CH_2)_{0-3}NHR^{2b}$; and each $R^{2b}$ is independently selected from hydrogen and $C_{1-6}$ alkyl.

In some embodiments, $R^1$ is $C_{1-4}$ alkyl. In some embodiments, $R^1$ is selected from the group consisting to methyl, ethyl, n-propyl, and n-butyl.

In some embodiments, $R^1$ is selected from the group consisting of:

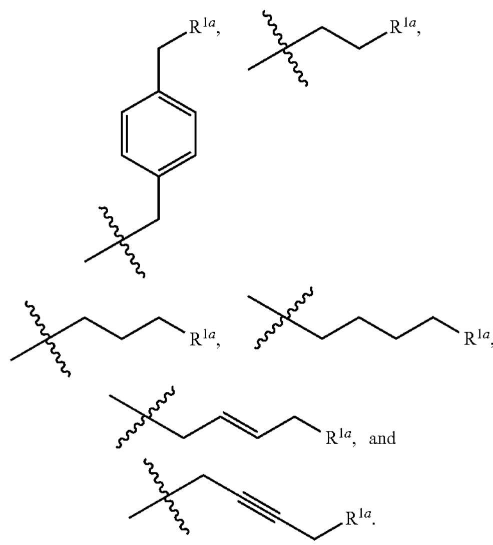

In some embodiments, $R^{1a}$ is $-OR^{1b}$. In some embodiments, $R^{1b}$ is hydrogen.

In some embodiments, alkylated nucleobase in the polynucleotide is selected from the group consisting of:
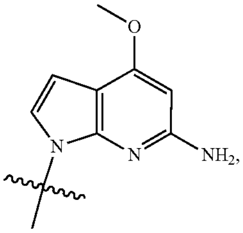
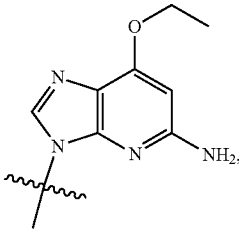
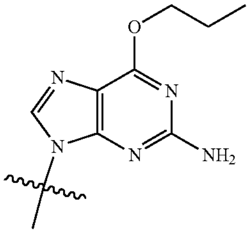
,
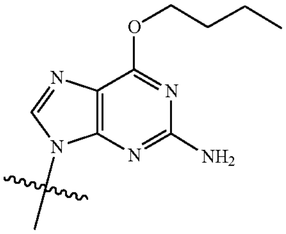
,
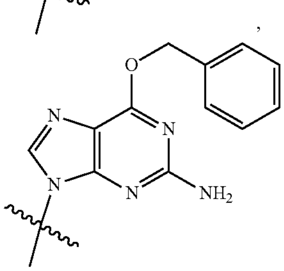
,
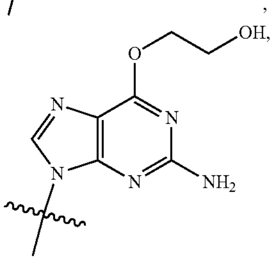
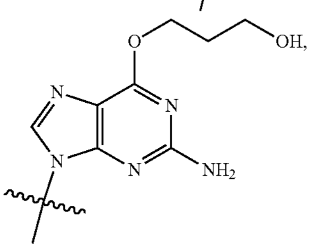
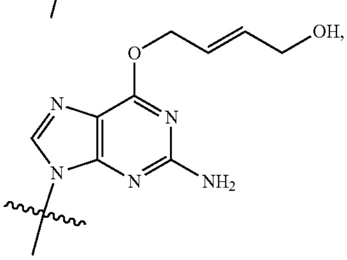
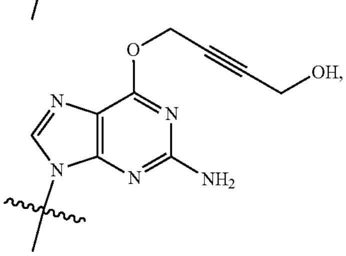
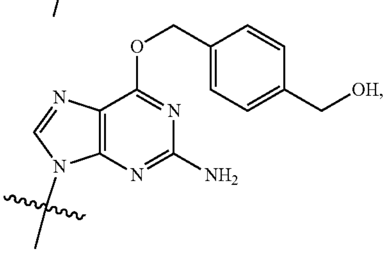
-continued
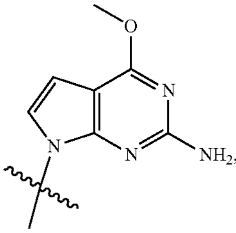
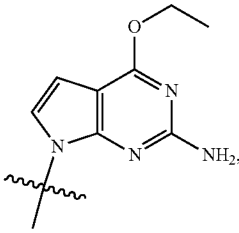
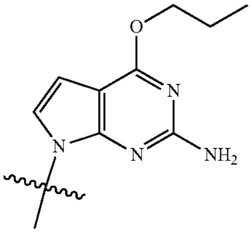
,
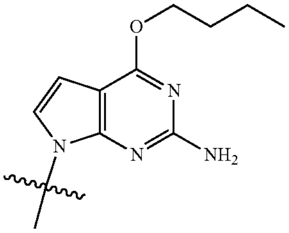
,
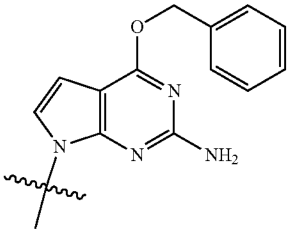
,
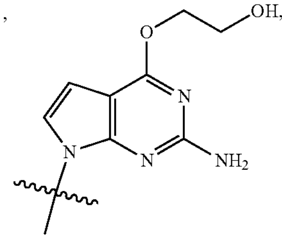
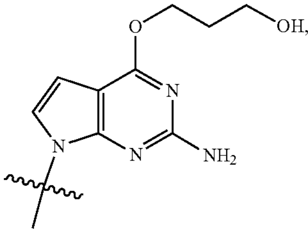
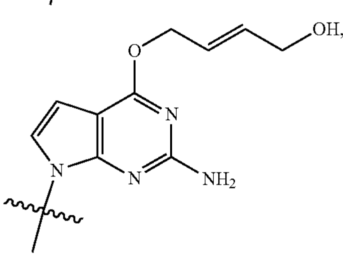
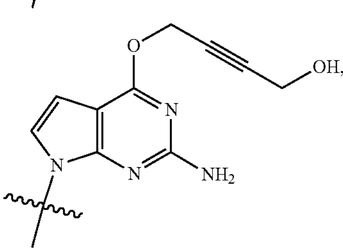
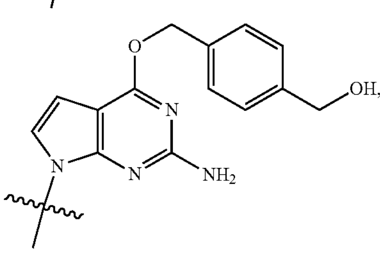

-continued
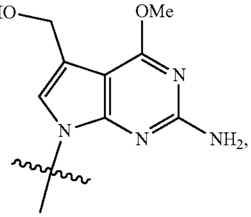
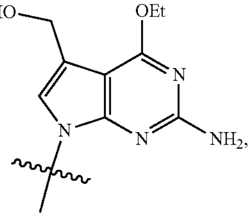
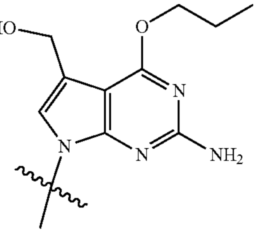
,
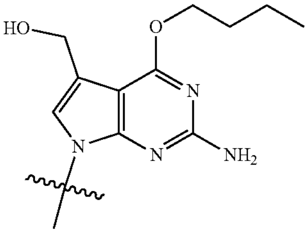
,
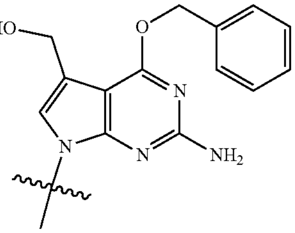
,
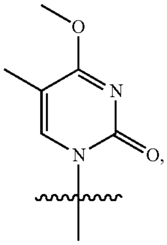
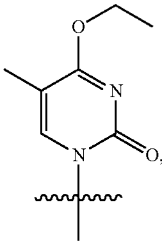
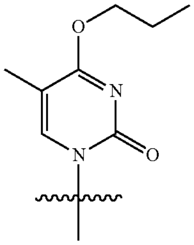
,
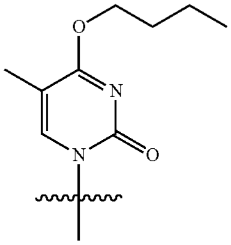
,
-continued
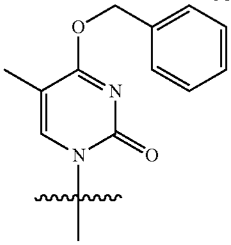
,
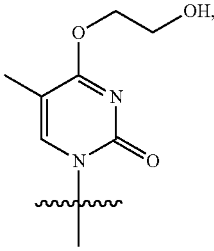
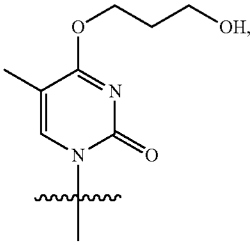
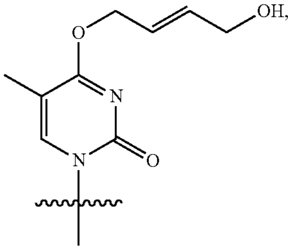
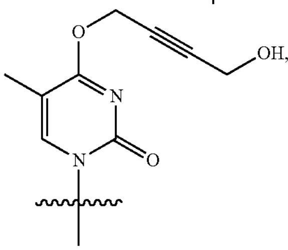
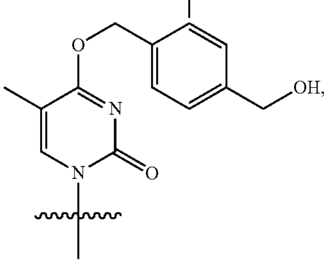
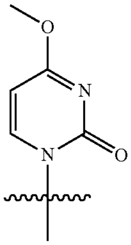
,
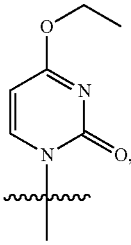
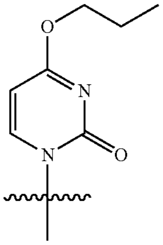
,
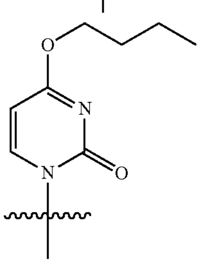
,
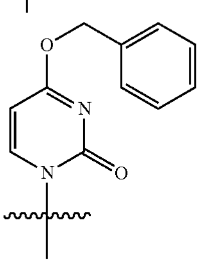
,
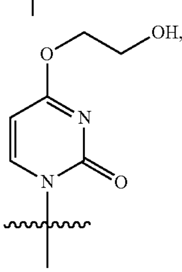
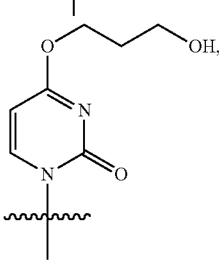

-continued

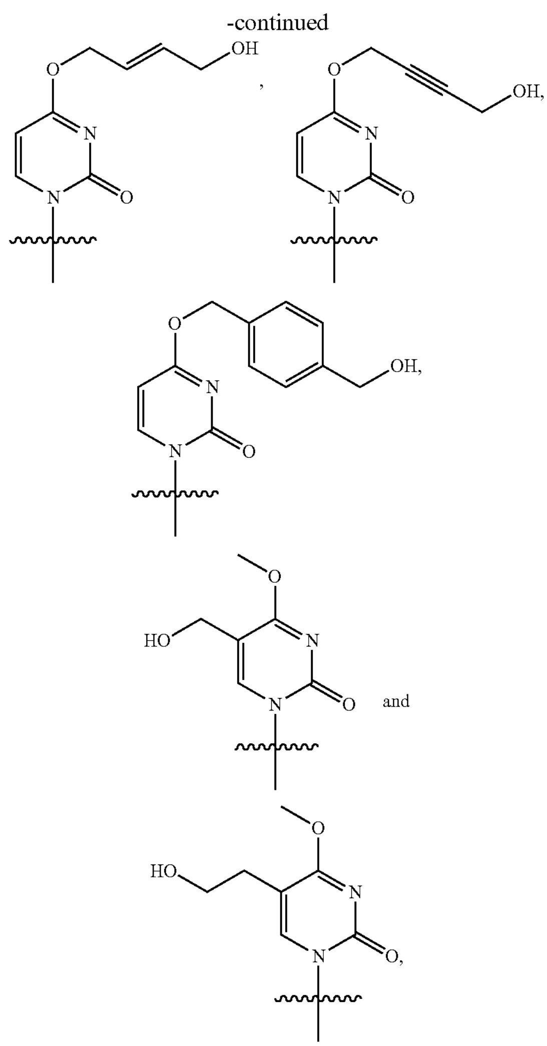

In some embodiments, the nucleotide is represented by

VI

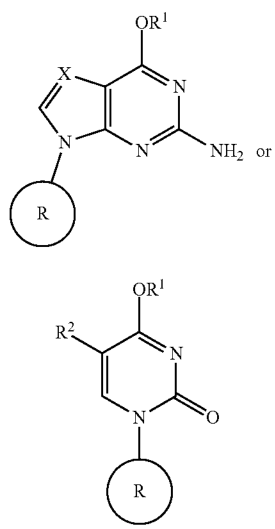

VII wherein $R^1$ is selected from the group consisting of $C_{1-6}$ alkyl, $C_{2-6}$ alkenyl, $C_{1-6}$ alkynyl, and $-(CH_2)_{0-3}Ph$, wherein $R^1$ is optionally substituted with 1-6 instances of $R^{1a}$;

each $R^{1a}$ is independently selected from halogen, $C_{1-6}$ alkyl, $-(CH_2)_{0-3}OR^{1b}$, $-NO_2$, $-N_3$, $-OPO_2OH$, and $-(CH_2)_{0-3}NHR^{1b}$; and each $R^{1b}$ is independently selected from hydrogen, $C_{1-6}$ alkyl, $-C(O)(C_{1-6}$ alkyl), $C_{1-6}$ haloalkyl, $-C(O)(C_{1-6}$ haloalkyl), and $-CH_2OAc$;

$R^2$ is hydrogen or methyl;

X is $-N=$ or $-C(H)=$; and

R is a ribose polyphosphate or deoxyribose polyphosphate.

In some embodiments, $R^1$ is $C_{1-3}$ alkyl. In some embodiments, $R^1$ is methyl.

In some embodiments, the nucleotide is selected from the group consisting of

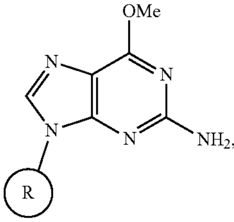

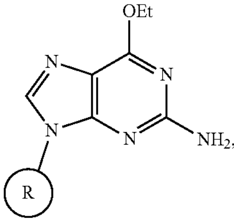

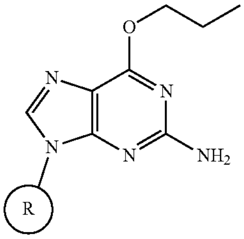

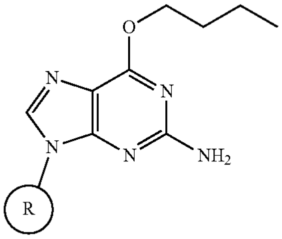

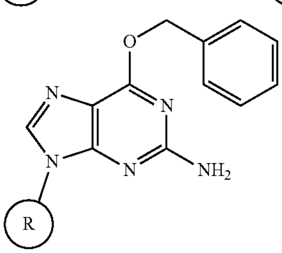

,

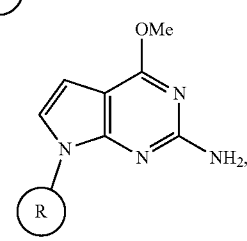

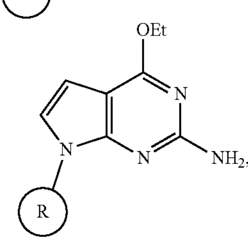

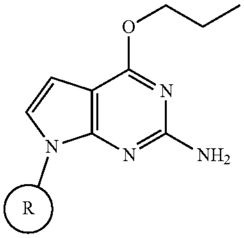

,

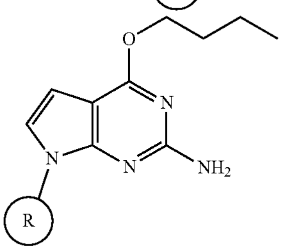

-continued

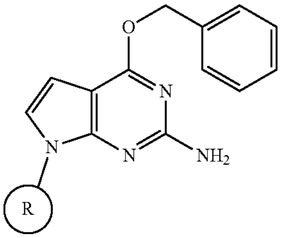,
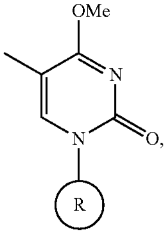

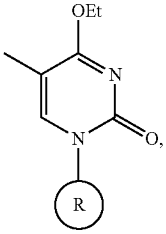
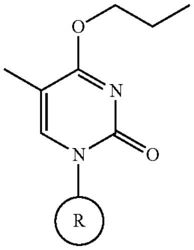,

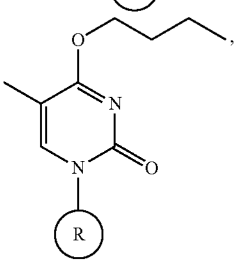,
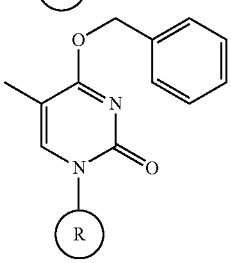,

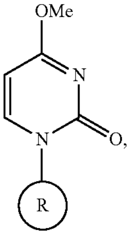
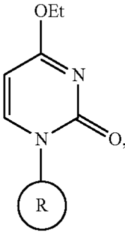
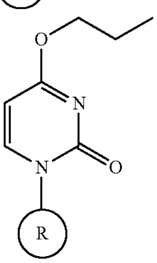,

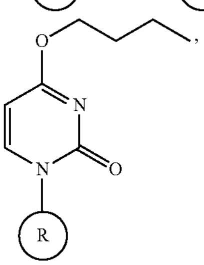, and
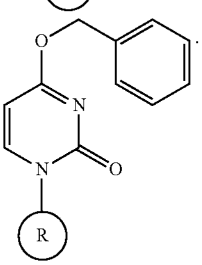.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

DETAILED DESCRIPTION

Figure 1A:
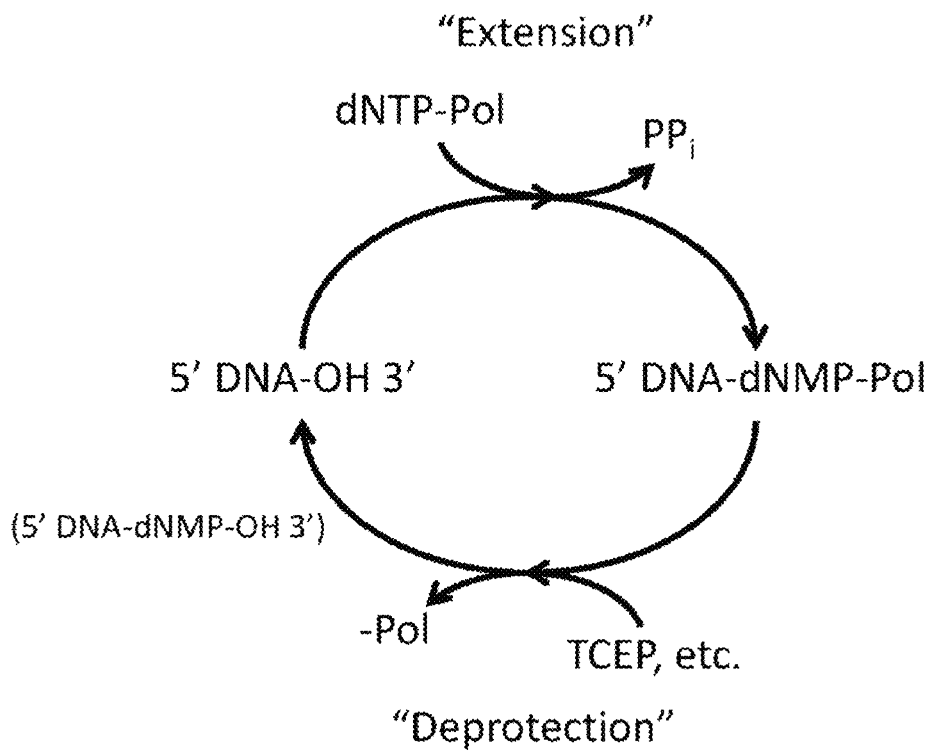
FIG. 1A. depicts a scheme for two-step cyclic nucleic acid synthesis using polymerase-nucleotide conjugates. In the first step, a conjugate binds to a DNA molecule via its linked dNTP moiety; in the second step the linkage between the polymerase and the elongated DNA molecule including the dNTP moiety is cleaved, deprotecting the end of the DNA molecule for subsequent elongation.

The details of various embodiments of the invention are set forth in the description below. Other features, objects, and advantages of the invention will be apparent from the description and the drawings, and from the claims.

Polynucleotide Synthesis Using O-Alkylated Nucleotides

The present disclosure includes a method of synthesizing a polynucleotide comprising one or more alkylated nucleobases, and removing one or more alkyl groups from said alkylated nucleobases. In some embodiments, inclusion of one or more alkylated nucleobases prevents base pairing or the formation of undesirable secondary structure during synthesis. In some embodiments, an alkylated nucleobase is described below in classes and subclasses herein.

These methods include improved methods for synthesis of nucleic acids by cyclic extension using a template-independent polymerase. As shown herein, secondary structure formation in the nascent chain, which may inhibit extension reactions, is suppressed by the use of modified nucleotides with methylation or other alkylations of the exocyclic oxygen of nucleobases that prevent Watson-Crick base pairing and/or other structures. After the synthesis is completed, the nucleobases can be converted back into their native form by enzymatic removal of the alkyl group.

In some embodiments, the present disclosure includes a method of synthesizing a polynucleotide, comprising: providing a polynucleotide comprising one or more alkylated nucleobases and removing one or more alkyl groups from said alkylated nucleobases. In some embodiments, providing a polynucleotide comprises: contacting a precursor polynucleotide with a nucleotide comprising an alkylated nucleobase and a template-independent polymerase; and adding said nucleotide to the 3' end of said precursor polynucleotide via said template-independent polymerase. In some embodiments, a method of synthesizing a polynucleotide further comprises repeating contacting and adding step one or more times.

After completion of synthesis of a polynucleotide using one or more alkylated nucleotides, the resulting polynucleotide can then be treated with an alkyl transferase to remove the alkyl group bound to the nucleotides, resulting in a polynucleotide with unmodified nucleobases. In some embodiments, removal of one or more alkyl groups from the synthesized polynucleotide comprises contacting the polynucleotide with one or more enzymes capable of removing said one or more alkyl groups from an alkylated nucleobase. In some embodiments, the enzyme suitable for de-alkylation of the alkylated nucleobase is an alkyl transferase. In some embodiments, a suitable enzyme for de-alkylating the polynucleotide is an alkyl transferase from EC 2.1.1.63. In some embodiments, the alkyl transferase is an AGT (alkylguanine transferase) enzyme, e.g., $O^6$-alkylguanine DNA alkyl transferase. In some embodiments the enzyme used to remove the alkyl group from the alkylated nucleobase is AlkB (*E. coli*), which is an alpha-ketoglutarate-dependent hydroxylase, which oxidatively dealkylates the DNA substrate.

Figure 2:
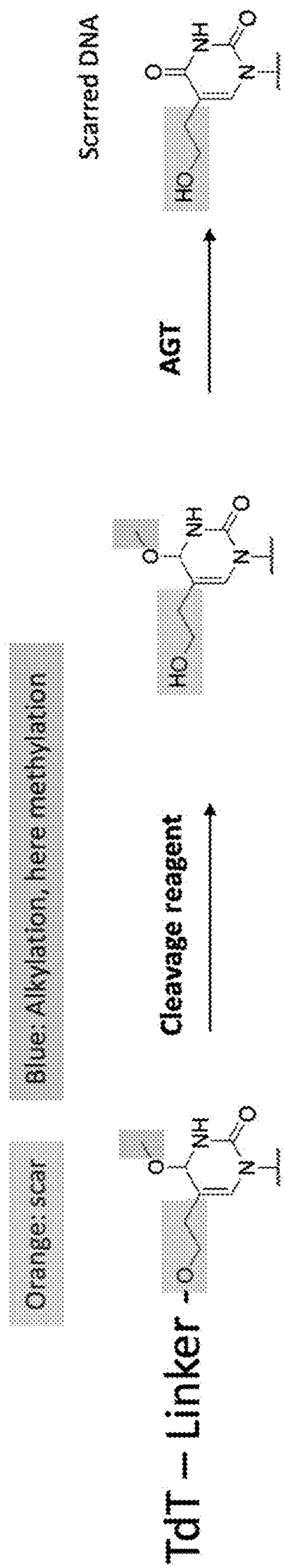
FIG. 2 depicts a scheme for nucleic acid synthesis using TdT-dNTP conjugates where the dNTP has an O-alkyl modification separate from its binding site to the linker. Cyclic nucleic acid synthesis comprises cleavage of the linker to remove TdT from the added dNTP using a cleavage agent which leaves a scar. Once nucleic acid synthesis is complete, the O-alkyl group is removed from the nucleotide(s) using AGT.
Figure 3:
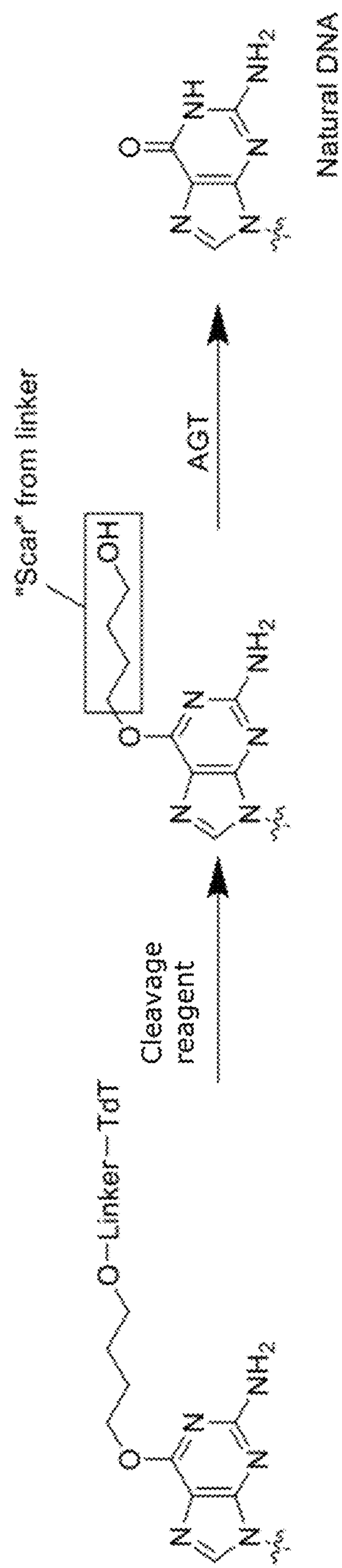
FIG. 3 depicts a scheme for nucleic acid synthesis using TdT-dNTP conjugates where cleavage of the linker to remove TdT from the added dNTP using a cleavage agent results in a nucleotide comprising an O-alkyl scar from the cleavage. Once nucleic acid synthesis is complete, the O-alkyl group is removed from the nucleotide(s) using AGT.

FIG. 2 and FIG. 3 show a reaction including cleavage of a linker in a nucleotide-TdT conjugate and removal of an alkyl group from an alkylated nucleotide by an AGT enzyme. In FIG. 2, the linker is separate from the alkyl modification of the nucleotide. In FIG. 3, the TdT is linked to the alkyl modification of the nucleotide and the alkyl group remains after cleavage of the linker binding the nucleotide and the TdT.

Suitable enzymes for use in de-alkylating alkylated nucleobases after completion of synthesis can be determined by screening a set of enzymes known to be involved in a de-alkylation reaction of a nucleobase or closely related reaction. One example of an easy screening method is described herein in Example 8. Using such screening methods, one of ordinary skill in the art can identify suitable enzymes for de-alkylation and implementations of this DNA synthesis strategy.

For example, although $O^6$-alkylguanine DNA alkyltransferase and AlkB are exemplified enzymes suitable for dealkylation, a number of other enzymes from various species are closely related and could also be suitable for use in the de-alkylation of the synthesized nucleotides. Tables 1 and 2 below provides a list of alkyl transferases that could be suitable to de-alkylate polynucleotide synthesis products described herein.

TABLE 1

| Alkyl transferase enzyme list (wild type) | |
|---|---|
| Alkyl Transferase Enzyme | Protein Sequence |
| AGT of *Homo sapiens* (NCBI Reference Sequence: NP_002403.3) | MDKDCEMKRTTLDSPLGKLELSGCEQGLHEIKLLGKGTS AADAVEVPAPAAVLGGPEPLMQCTAWLNAYFHQPEAIEE FPVPALHHPVFQQESFTRQVLWKLLKVVKFGEVISYQQL AALAGNPKAARAVGGAMRGNPVPILIPCHRVVCSSGAVG NYSGGLAVKEWLLAHEGHRLGKPGLGGSSGLAGAWLKGA GATSGSPPAGRN(SEQ ID NO: 1) |
| OGT of *Escherichia coli* (GenBank: EHH7550609.1) | MLRLLEEKIATPLGPLWVICDEQFRLRAVEWEEYS ERMVQLLDIHYRKEGYERISATNPGGLSDKLREYF AGNLSIIDTLPTATGGTPFQREVWKILRTIPCGQV MHYGQLAEQLGRPGAARAVGAANGSNPISIVVPCH RVIGRNGTMTGYAGGVQRKEWLLRHEGYLLL (SEQ ID NO: 2) |

TABLE 1-continued

| Alkyl transferase enzyme list (wild type) | |
|---|---|
| Alkyl Transferase Enzyme | Protein Sequence |
| Ada of *Escherichia coli* (NCBI Reference Sequence: WP_000710375.1) | MKKATCLTDDQRWQSVLARDPNADGEFVFAVRITG IFCRPSCRARHALRENVSFYANASEALAAGFRPCK RCQPEKANAQQHRLDKITHACRLLEQETPVTLEAL ADQVAMSPFHLHRLFKATTGMTPKAWQQAWRARRL RESLAKGESVTTSILNAGFPDSSSYYRKADETLGM TAKQFRHGGENLAVRYALADCELGRCLVAESERGI CAILLGDDDATLISELQQMFPAADNAPADLMFQQH VREVIASLNQRDTPLTLPLDIRGTAFQQQVWQALR TIPCGETVSYQQLANAIGKPKAVRAVASACAANKL AIIIPCHRVVRGDGTLSGYRWGVSRKAQLLRREAE NEER(SEQ ID NO: 3) |
| AGT of *Archaeoglobus fulgidus* (NCBI Reference Sequence: WP_010879803.1) | MFSVKWGELYFNVVMEGGKAVKSYFSTYPSFSSSD SEYARQLERYFSGERVEVRIPYRLKASSFTRRVLE EVSRIPYGMVRMYSDIAKALNTSPRAVGQAVKRNP LPVIIPCHRVVGKKEIGGYTVSCSDIDGKSLKKRL LRLEGVF(SEQ ID NO: 4) |
| AGT of *Aquifex aeolicus* (GenBank: AAC07432.1) | MSTERRREVISGTSAQIALIILRKITIRGAELQDL PEERYVKSVYSLKSQTKKTVIPITVLKTALTPSLS LEIFFDKGKISKISILKKKEQKIIPEFLLYFLKEG DPLINLEYLDLKRINPKCIKVYLKLKEVASFGKII TYGELARLTDLHPRFVGYCMKINPFPVIIPCHRVI SKRDLGGFNQGIEIKSELLKHEGLIL (SEQ ID NO: 5) |
| AGT of *Ferroplasma acidarmanus* (NCBI Reference Sequence: WP_009886675.1) | MKNNNIKIQYYKTKIGELILGSFEGNLCILDFRYS KKRTTIDNRIKTGLKANFLEEEDEILAETKKQVAE YLDGNRKEFDIPLLMVGTDFQKNVWNALLKIPYGT TITYLQLAKNIGNAKAVRAVANADGANAMAVIIPC HRVIESNGGLGGYGGGVAIKKQLLELEKGNPEQ (SEQ ID NO: 6) |
| AGT of *Methanococcus jannaschi* (NCBI Reference Sequence: WP_010871053.1) | MIIQIEEYFIGMIFKGNQLVRNTIPLRREEIFNEM DGEVVSNPEDEHLKVAEIILKLYFAEIDDKKVREL ISYKLEVPEFTKKVLDIVKDIEFGKTLTYGDIAKK LNTSPRAVGMALKRNPLPLIIPCHRVVAKNSLGGY SYGLDKKKFILERERLNMVSFKFNKVY (SEQ ID NO: 7) |
| AGT of *Mycobacterium tuberculosis* (GenBank: AAK45619.1) | MIHYRTIDSPIGPLTLAGHGSVLINLRMLEQTYEP SRTHWTPDPGAFSGAVDQLNAYFAGELIEFDVELD LRGTDFQQRVWKALLTIPYGETRSYGEIADQIGAP GAARAVGLANGHNPIAIIVPCHRVIGASGKLIGYG GGINRKRALLELEKSRAPADLTLFD (SEQ ID NO: 8) |
| AGT of *Pyrococcus furiosus* (NCBI Reference Sequence: WP_011013017.1) | MILEVRKFQVKNKAVYIGTLSEDKIFGIIFSIDEP EVIRHRIPTLINFLEKRLNKKLEIKEGNSGFSDVV FKTLIGKISNEEAAEFIEVSYLTKFERKLYIYLVE NVKRGEVITYGELAKILNTSSRAVGAAVKRNPYPI IVPCHRVIGRKNPYLYTPKPEYKKFLLEVEGWTS (SEQ ID NO: 9) |
| AGT of *Sulfolobus solfataricus* (NCBI Reference Sequence: WP_010923891.1) | MLVYGLYKSPLGYITVAKDDKGFIMLDFCDCVEGN SRDDSSFTEFFHKLDLYFEGKPINLREPINLKTYP FRLSVFKEVMKIPWGKVMTYKQIADSLGTSPRAVG MALSKNPILLIIPCHRVIAENGIGGYSRGVKLKRA LLELEGVKIPE (SEQ ID NO: 10) |
| AGT of *Sulfolobus tokodaii* (NCBI Reference Sequence: WP_010978968.1) | MIVYGLYKSPFGPITVAKNEKGFVMLDFCDCAERS SLDNDYFTDFFYKLDLYFEGKKVDLTEPVDFKPEN EFRIRVFKEVMRIKWGEVRTYKQVADAVKISPRAV GTALSKNNVLLIIPCHRVIGEKSLGGYSRGVELKR KLLELEGIDVAKFIEK (SEQ ID NO: 11) |
| AGT of *Thermococcus kodakarensis* (NCBI Reference Sequence: WP_011250921.1) | MLSVEKFRVGERVVWIGVIFSGRVQGIAFAFDRGT LMKRIHDLAEHLGKRGVSISLDVQPSDYPEKVFKV LIGELDNASFLRELSFEGVTPFEKKVYEWLIKNVK RGSVITYGDLAKALNISPRAVGGAMKRNPYPIVVP CHRVVAHDGIGYYSSGIEEKKFLLEIEGVKEWTS (SEQ ID NO: 12) |

TABLE 1-continued

| Alkyl transferase enzyme list (wild type) | |
|---|---|
| Alkyl Transferase Enzyme | Protein Sequence |
| AGT of *Thermotoga neapolitana* (GenBank: ACM23864.1) | MRDRFFHRSDRSQIYTPFMESSSNEPVIILSGGGD FFMKDLPGNISVRVENGKVVEIKLGSDESNCPPKV KKELEEYFSGKRKEFSFPVEIRGTSFQKKVWEEVR KIPYGETRTYREIAEKLNTSPRAVGQALAKNPLPL YIPCHRVVSKRGLGGFSAGLEWKRFLIDLERGSR (SEQ ID NO: 13) |

TABLE 2

| Alkyl transferase enzyme list (engineered variants) | |
|---|---|
| Alkyl Transferase Enzyme | Protein Sequence |
| hOGT chimera (McManus F.P. and Wilds C.J., *Toxicol. Res.*, 2013, 2, 158; DOI: 10.1039/c2tx20075a) | MDKDCEMKRTTLDSPLGKLELSGCEQGLHEIKLLGKGTSA ADAVEVPAPAAVLGGPEPLMQCTAWLNAYFHQPEAIEEFP VPALHHPVFQQESFTRQVLWKLLKVVKFGEVISYQQLAAL AGNPKAARAVGGAMRGNPIPIVVPCHRVIGRNGTMTGYAG GLAVKEWLLAHEGHRLGKPGLGGSSGLAGAWLKGAGATSG SPPAGRN (SEQ ID NO: 14) |
| OGTS134P mutant (Schoonhoven N., O'Flaherty D.K., McManus F.P., Sacre L., Noronha A.M., Kornblatt M.J. and Christopher J. Wilds, *Molecules*, 2017, 22, 1948; DOI: 10.3390/molecules22111948) | MLRLLEEKIATPLGPLWVICDEQFRLRAVEWEEYSERMVQ LLDIHYRKEGYERISATNPGGLSDKLREYFAGNLSIIDTL PTATGGTPFQREVWKTLRTIPCGQVMHYGQLAEQLGRPGA ARAVGAANGSNPIPIVVPCHRVIGRNGTMTGYAGGVQRKE WLLRHEGYLLL (SEQ ID NO: 15) |
| $^{PGEG}$hAGT mutant (Juillerat A., Gronemeyer T., Keppler A., Gendreizig S., Pick H., Vogel H., and Johnsson K., *Chem. Biol.*, 2003, 10, 313; DOI 10.1016/S1074-5521(03)00068-1) | MDKDCEMKRTTLDSPLGKLELSGCEQGLHEIKLLGKGTSA ADAVEVPAPAAVLGGPEPLMQCTAWLNAYFHQPEAIEEFP VPALHHPVFQQESFTRQVLWKLLKVVKFGEVISYQQLAAL AGNPKAARAVGGAMRGNPVPILIPCHRVVCSSGAVGGYEG GLAVKEWLLAHEGHRLGKPGLGGSSGLAGAWLKGAGATSG SPPAGRN (SEQ ID NO: 16) |
| $^{PGEA}$hAGT mutant (Juillerat A., Gronemeyer T., Keppler A., Gendreizig S., Pick H., Vogel H., and Johnsson K., *Chem. Biol.*, 2003, 10, 313; DOI 10.1016/S1074-5521(03)00068-1) | MDKDCEMKRTTLDSPLGKLELSGCEQGLHEIKLLGKGTSA ADAVEVPAPAAVLGGPEPLMQCTAWLNAYFHQPEAIEEFP VPALHHPVFQQESFTRQVLWKLLKVVKFGEVISYQQLAAL AGNPKAARAVGGAMRGNPVPILIPCHRVVCSSGAVGGYEA GLAVKEWLLAHEGHRLGKPGLGGSSGLAGAWLKGAGATSG SPPAGRN (SEQ ID NO: 17) |
| AGT53 mutant (Juillerat A., Heinis C., Sielaff I., Barnikow J., Jaccard H., Kunz B., Terskikh A., and Johnsson K., *ChemBioChem* 2005, 6, 1263; DOI : 10.1002/cbic.200400431) | MDKDCEMKRTTLDSPLGKLELSGCEQGLHEIKLLGKGTSA ADAVEVPAPAAVLGGPEPLMQCTAWLNAYFHQPEAIEEFP VPALHHPVFQQESFTRQVLWKLLKVVKFGEVISYQQLAAL AGNPKAARAVVHALRGNPVPILIPCHRVVCSSGAVGGYEG GLAVKEWLLAHEGHRLGKPGLGGSSGLAGAWLKGAGATSG SPPAGRN (SEQ ID NO: 18) |
| AGT54 mutant (Juillerat A., Heinis C., Sielaff I., Barnikow J., Jaccard H., Kunz B., Terskikh A., and Johnsson K., *ChemBioChem* 2005, 6, 1263; DOI: 10.1002/cbic.200400431) | MDKDCEMKRTTLDSPLGKLELSGCEQGLHEIKLLGKGTSA ADAVEVPAPAAVLGGPEPLMQCTAWLNAYFHQPEAIEEFP VPALHHPVFQQESFTRQVLWKLLKVVKFGEVISYQQLAAL AGNPKAARAVKTALSGNPVPILIPCHRVVCSSGAVGGYEG GLAVKEWLLAHEGHRLGKPGLGGSSGLAGAWLKGAGATSG SPPAGRN (SEQ ID NO: 19) |
| 56-8 mutant (Encell L.P., Loeb L.A., *Biochemistry*, 1999, 38, 12097; DOI: 10.1021/bi9913606) | MDKDCEMKRTTLDSPLGKLELSGCEQGLHEIKLLGKGTSA ADAVEVPAPAAVLGGPEPLMQCTAWLNAYFHQPEAIEEFP VPALHHPVFQQESFTRQVLWKLLKVVKFGEVISYQQLAAL AGNPKAARAVGGAMRGNPVPILIPCHRVVYSRGSGGTYSG GLAVREWLLAHEGHRLGKPGLGGSSGLAGAWLKGAGATSG SPPAGRN(SEQ ID NO: 20) |
| hAGT-01 mutant (Fang Q., Kanugula S., Tubbs J.L., Tainer J.A., and Pegg A.E., *J. Biol.* | MDKDCEMKRTTLDSPLGKLELSGCEQGLHEIKLLGKGTSA ADAVEVPAPAAVLGGPEPLMQCTAWLNAYFHQPEAIEEFP VPALHHPVFQQESFTRQVLWKLLKVVKFGEVISYQQLAAL |

TABLE 2-continued

| Alkyl transferase enzyme list (engineered variants) | |
|---|---|
| Alkyl Transferase Enzyme | Protein Sequence |
| *Chem.* 2010, 285, 8185; DOI 10.1074/jbc.M109.045518) | AGNPKAARAVGGAMRGNPISIVVPCHRVIGRNGTMTGYAG GVQRKEWLLAHEGHRLGKPGLGGSSGLAGAWLKGAGATSG SPPAGRN(SEQ ID NO: 21) |
| hAGT-02 mutant (Fang Q., Kanugula S., Tubbs J.L., Tainer J.A., and Pegg A.E., *J. Biol. Chem.* 2010, 285, 8185; DOI 10.1074/jbc.M109.045518) | MDKDCEMKRTTLDSPLGKLELSGCEQGLHEIKLLGKGTSA ADAVEVPAPAAVLGGPEPLMQCTAWLNAYFHQPEAIEEFP VPALHHPVFQQESFTRQVLWKLLKVVKFGEVISYQQLAAL AGNPKAARAVGGAMRGNPISIVVPCHRVIGRNGTMTGYAG GVQRKEWLLAHEGHRLGKPGLGGSSGLAGAWLKGAGATSG SPPAGRN (SEQ ID NO: 22) |
| hAGT-03 mutant (Fang Q., Kanugula S., Tubbs J.L., Tainer J.A., and Pegg A.E., *J. Biol. Chem.* 2010, 285, 8185; DOI 10.1074/jbc.M109.045518) | MDKDCEMKRTTLDSPLGKLELSGCEQGLHEIKLLGKGTSA ADAVEVPAPAAVLGGPEPLMQCTAWLNAYFHQPEAIEEFP VPALHHPVFQQESFTRQVLWKLLKVVKFGEVISYQQLAAL AGNPKAARAVGGAMRGNPVPILIPCHRVIGRNGTMTGYSG GLAVKEWLLAHEGHRLGKPGLGGSSGLAGAWLKGAGATSG SPPAGRN (SEQ ID NO: 23) |

In some embodiments, an alkylated nucleobase is represented by Formula (V) or (VI):

V

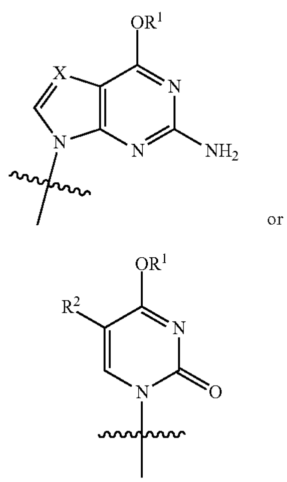

or

VI wherein

X is —C($R^2$)═ or —N═;

$R^1$ is selected from the group consisting of $C_{1-6}$ alkyl, $C_{2-6}$alkenyl, $C_{1-6}$ alkynyl, and —$(CH_2)_{0-3}$Ph, wherein $R^1$ is optionally substituted with 1-6 instances of $R^{1a}$;

each $R^{1a}$ is independently selected from halogen, $C_{1-6}$ alkyl, —$(CH_2)_{0-3}OR^{1b}$, —$NO_2$, —$N_3$, —$OPO_2OH$, and —$(CH_2)_{0-3}NHR^{1b}$; and each $R^{1b}$ is independently selected from hydrogen, $C_{1-6}$ alkyl, —C(O)($C_{1-6}$ alkyl), $C_{1-6}$ haloalkyl, —C(O)($C_{1-6}$ haloalkyl), and —$CH_2OAc$;

$R^2$ is selected from the group consisting of hydrogen, optionally substituted $C_{1-4}$ alkyl chain, wherein 1-2 methylene units is optionally and independently replaced with —O—, —N($R^a$)—, —C(O)—, —S—, —S(O)—, —$S(O)_2$—, or phenylene, wherein $R^2$ is optionally substituted with 1-6 instances of $R^{2a}$;

each $R^{2a}$ is independently selected from halogen, $C_{1-6}$ alkyl, —$(CH_2)_{0-3}OR^{2b}$, —$NO_2$, —$N_3$, —$OPO_2OH$, and —$(CH_2)_{0-3}NHR^{2b}$; and each $R^{2b}$ is independently selected from hydrogen and $C_{1-6}$ alkyl.

In some embodiments, $R^1$ is $C_{1-4}$ alkyl. In some embodiments, $R^1$ is selected from the group consisting to methyl, ethyl, n-propyl, and n-butyl. In some embodiments, $R^1$ is methyl. In some embodiments, $R^1$ is ethyl. In some embodiments, $R^1$ is n-propyl. In some embodiments, $R^1$ is n-butyl.

In some embodiments, $R^1$ is selected from the group consisting of:

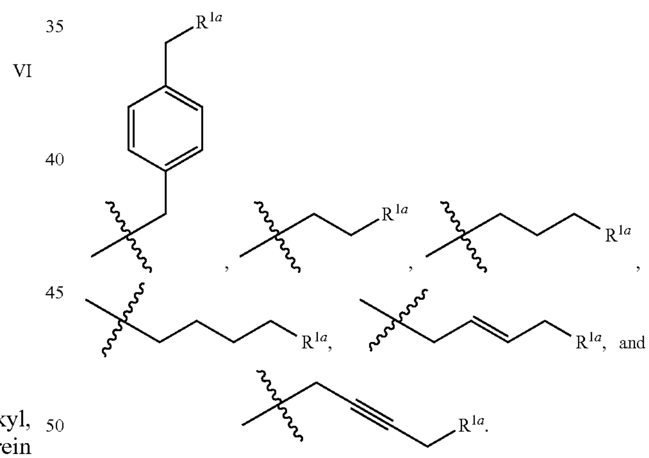

In some embodiments, $R^1$ is selected from the group consisting of:

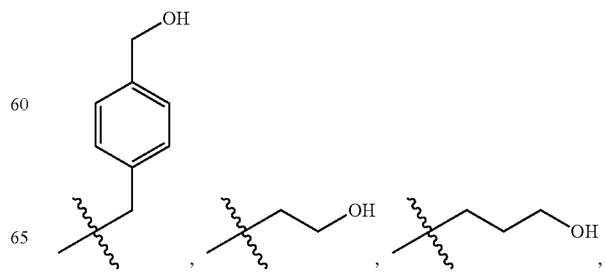

-continued
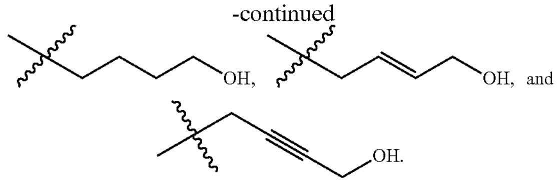
In some embodiments, X is —C($R^2$)═ or —N═. In some embodiments, X is —C($R^2$). In some embodiments, X is —N═.
In some embodiments, $R^2$ is selected from the group consisting of hydrogen or $C_1$-$C_2$ alkyl optionally substituted with —OH.
In some embodiments, an alkylated nucleobase is selected from the group consisting of:
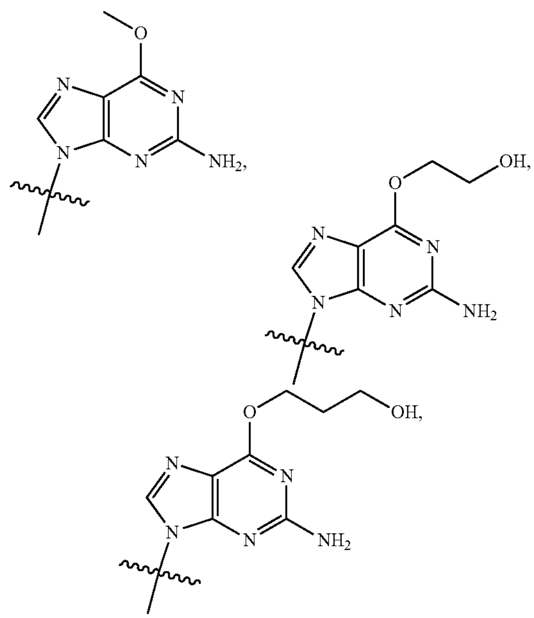
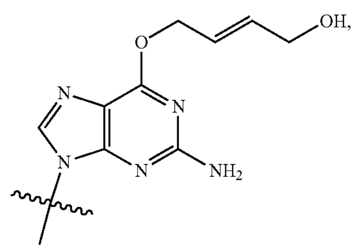
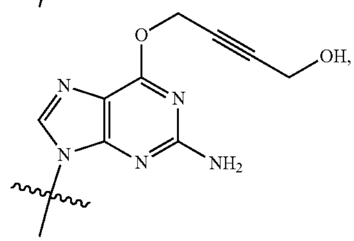
-continued
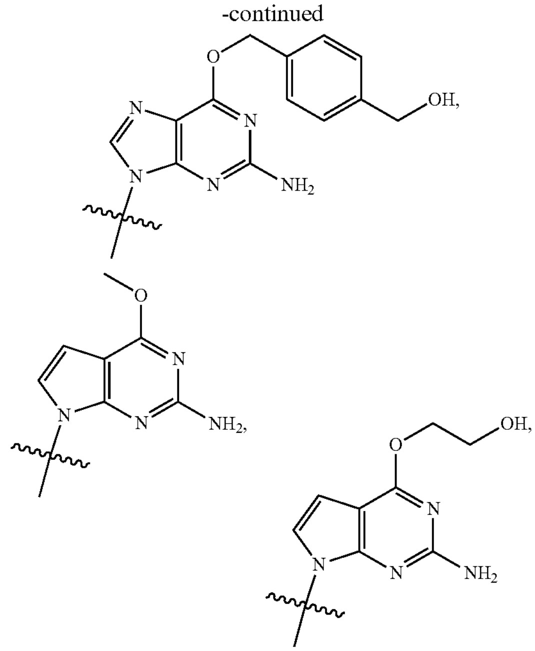
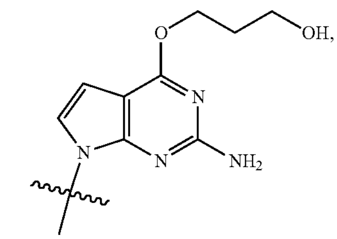
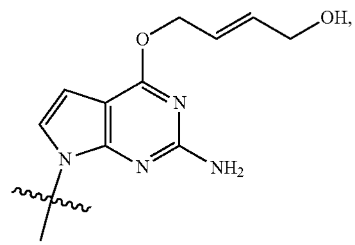
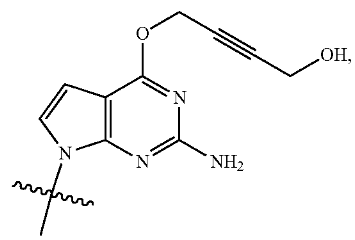
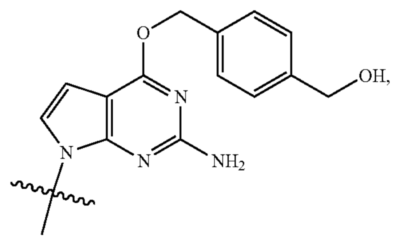

-continued
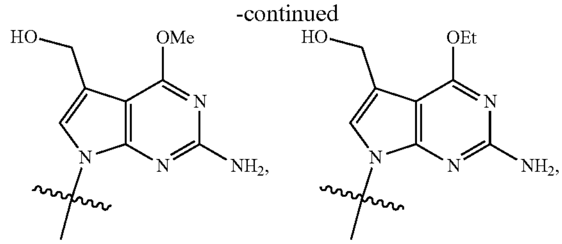
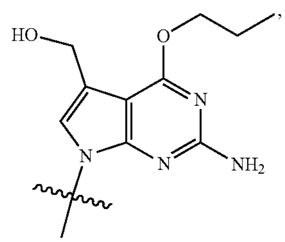
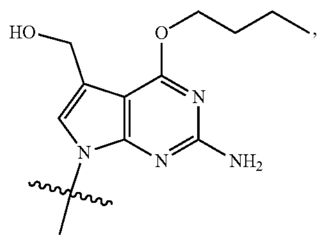
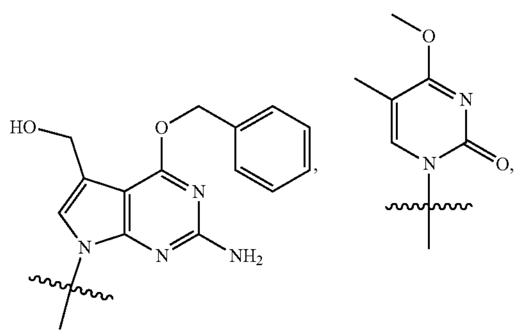
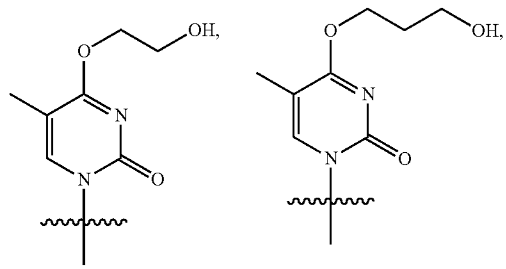
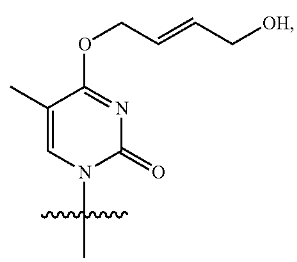
-continued
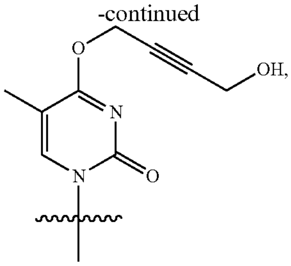
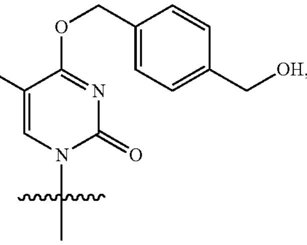
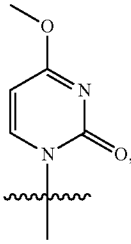
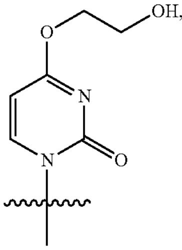
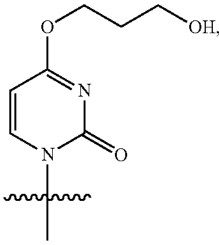
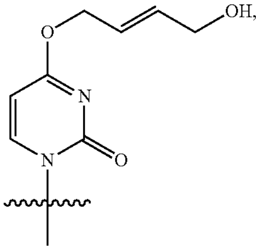
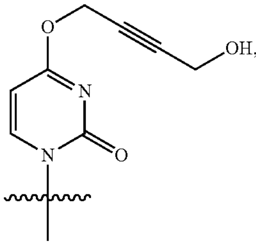
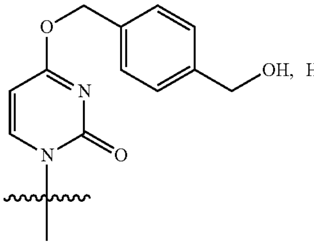
and
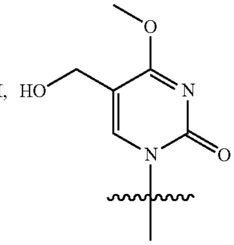
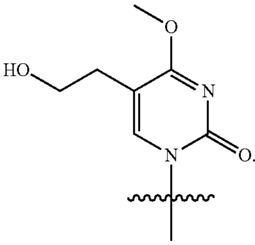
Conjugates
In some embodiments, the present disclosure includes use of TdT with free nucleotides that have a 3' modification to enable single extensions. In some embodiments, the present disclosure also includes use of TdT with a tethered nucleotide (we call this polymerase-nucleotide conjugate). Linkage of the dNTP can occur via a tether to the nucleobase. In some embodiments, a nucleotide comprises an optionally substituted O-alkyl group. Additional tethered nucelotides can be found, e.g., in PCT Publication WO2017/223517 "Nucleic Acid Synthesis and Sequencing Using Tethered Nucleoside Triphosphates," the entirety of which is incorporated by reference.

Described herein is a method for the de novo synthesis of nucleic acids using conjugates comprising a polymerase and a nucleoside triphosphate. In some embodiments of the method, conjugates comprise the polymerase Terminal deoxynucleotidyl Transferase (TdT). In other embodiments, the method may employ conjugates comprising another template-independent polymerase.

Figure 1B:
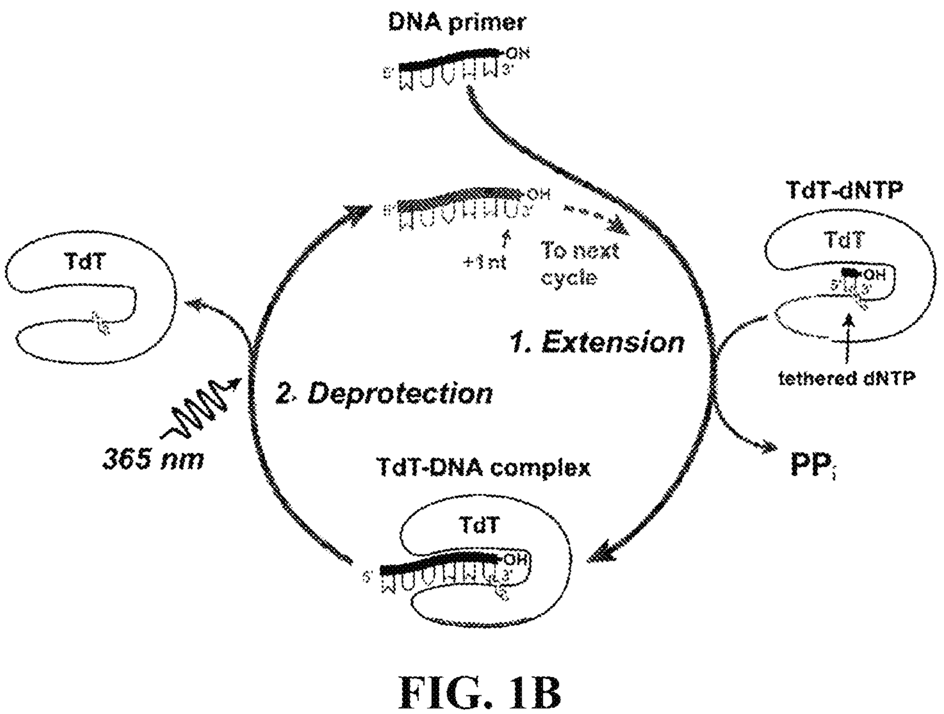
FIG. 1B depicts a scheme for two-step cyclic nucleic acid synthesis using TdT-dNTP conjugates comprising a TdT molecule site-specifically linked to a dNTP via a cleavable linker.

FIG. 1A illustrates a typical process for the stepwise synthesis of a defined sequence using a template-independent polymerase. A nucleic acid that serves as an initial substrate for elongation (i.e. "starter molecule") is incubated with a first polymerase-nucleotide conjugate. Once the nucleic acid has been elongated by the tethered nucleotide of a conjugate, no further elongations occur because the conjugates implement a termination mechanism. In the second step of the process, the linker is cleaved to release the polymerase and reverse the termination mechanism, thus enabling subsequent elongations. The elongation products are then exposed to the second conjugate, and these two steps are iterated to elongate the nucleic acid by a defined sequence. FIG. 1B illustrates a synthesis procedure using a conjugate comprising TdT and a photocleavable linker. As described above, other strategies are available for the attachment and cleavage of the linker.

For RNA synthesis applications, tethered ribonucleoside triphosphates may be used. In these embodiments, a RNA specific nucleotidyl transferase, such as *E. coli* Poly(A) Polymerase (IUBMB EC 2.7.7.19) or Poly(U) Polymerase, among others, may be employed. The RNA nucleotidyl transferases can contain modifications, e.g., single point mutations, that influence the substrate specificity towards a specific rNTP (Lunde et al., Nucleic acids research 40.19 (2012): 9815-9824.). In some embodiments, a very short tether between an RNA nucleotidyl transferase and a ribonucleoside triphosphate may be used to induce a high effective concentration of the nucleoside triphosphate, thereby forcing incorporation of an rNTP that might not be the natural substrate of the nucleotidyl transferase.

In some embodiments, the linker is attached to a different position of the base than the alkylation.

In some embodiments, the linker is specifically attached to an amino acid of the polymerase. In these cases, it is preferable to attach the linker to an amino acid at a position that can be mutated without loss of the polymerase activity, e.g. positions 180, 188, 253 or 302 of murine TdT (numbering as in the crystal structure PDB ID: 4127). It is preferable to not attach the linker to an amino acid involved in the catalytic activity of the polymerase to avoid interfering with catalysis. Residues known to be involved with catalysis and methods for determining if a residue is involved with catalysis (e.g. by site-specific mutagenesis) will be apparent to those skilled in the art and are reviewed in literature (e.g. Joyce et al. (Journal of Bacteriology 177.22 (1995): 6321.) and Jara and Martinez (The Journal of Physical Chemistry B 120.27 (2016): 6504-6514.))

In some embodiments, a linker of a conjugate may be attached to the 7-position of deaza dGTP or the 5-position of dTTP or dUTP.

In some embodiments, the linker of the conjugate is cleaved to leave a scar. In such cases, scars may remain on the DNA after cleavage. In some embodiments, a scar comprises a hydroxyl. In some embodiments, a scar comprises an amine. In some embodiments, a scar comprises a hydroxylalkyl group.

In some embodiments, the linker of a conjugate is attached to an O-alkylated nucelobase at the alkyl group. In particular embodiments, the linker of a conjugate attached to an O-alkylated nucleobase is cleaved to leave a scar. In some embodiments, a scar is removed using an enzyme capable of removing said one or more alkyl groups from an alkylated nucleobase.

In some embodiments, a conjugate is represented by a structure of Formula (I) or (II):

I

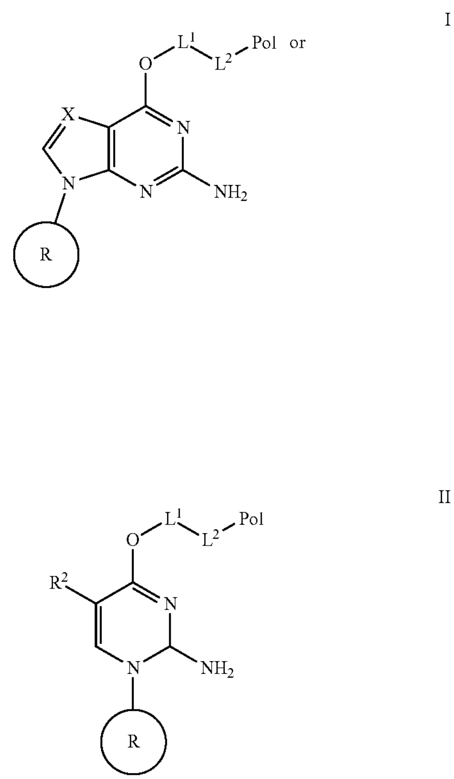

or

II wherein $L^1$ is selected from the group consisting of an optionally substituted $C_{1-6}$ alkylene chain, an optionally substituted $C_{2-6}$ alkenylene chain, and an optionally substituted $C_{1-6}$ alkynylene chain, wherein 1-4 methylene units are optionally and independently replaced with —O—, —N($R^a$)—, —C(O)—, —S—, —S(O)—, —$S(O)_2$—, or phenylene;

$L^2$ is a cleavable linker;

X is —N═ or —C(H)═;

each $R^a$ is independently hydrogen or $C_{1-6}$ alkyl;

$R^2$ is hydrogen or methyl;

R is a ribose polyphosphate or deoxyribose polyphosphate; and

Pol is a polymerase.

In some embodiments, the conjugate is represented by
II-a
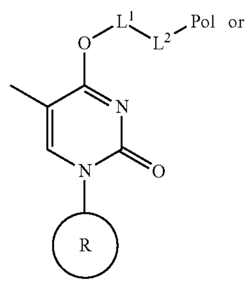
or
II-b
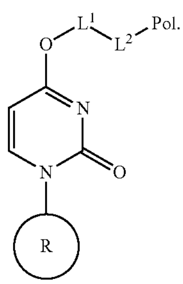
In some embodiments, $L^1$ is selected from the group consisting of
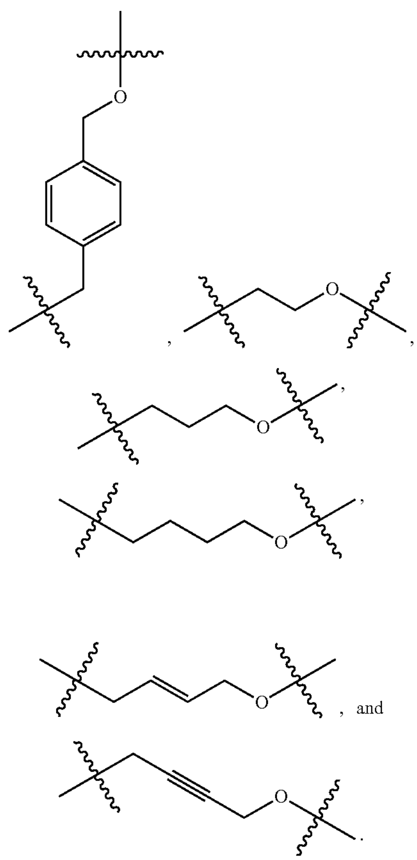
In some embodiments, the conjugate is selected from the group consisting of
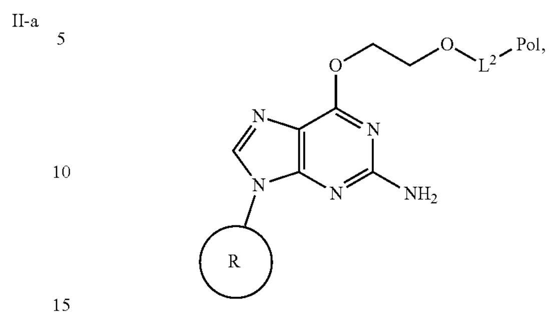
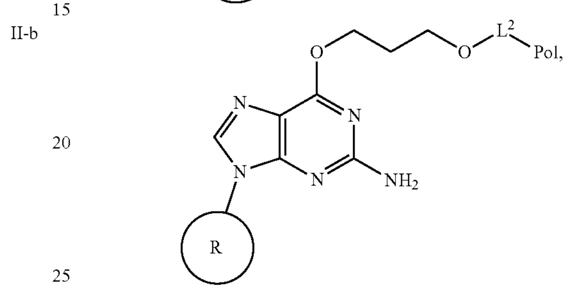
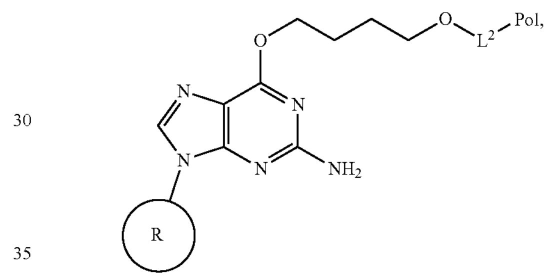
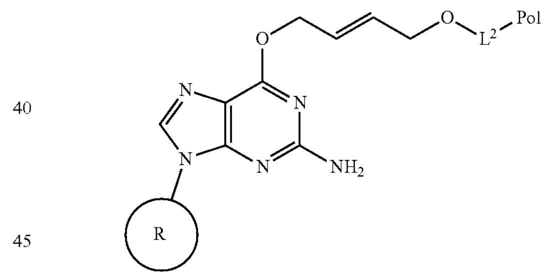
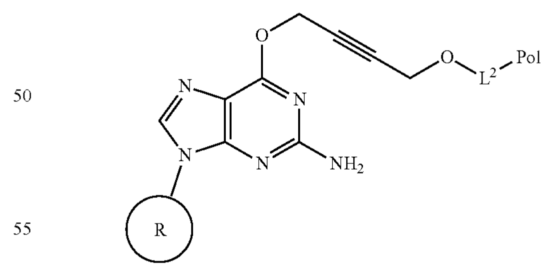
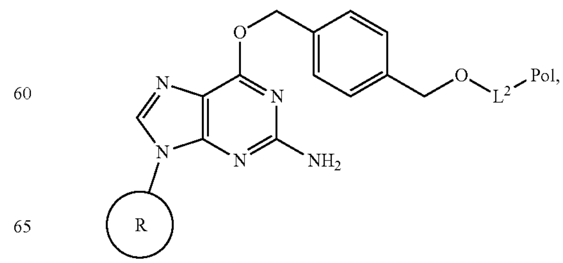

-continued
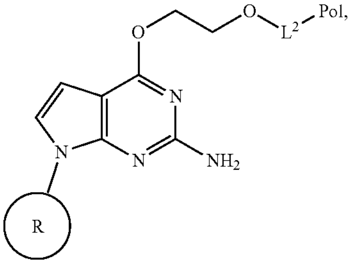
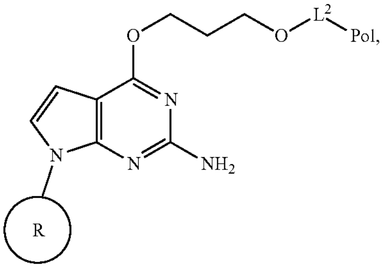
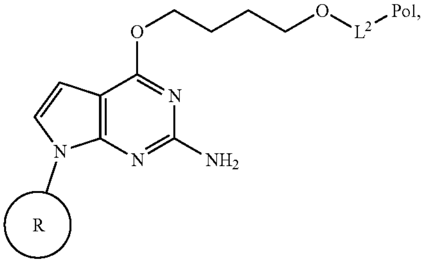
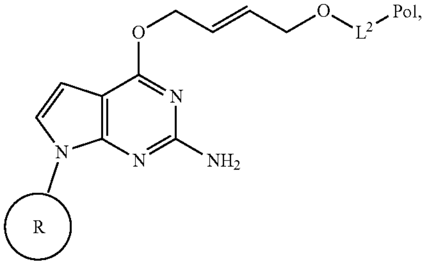
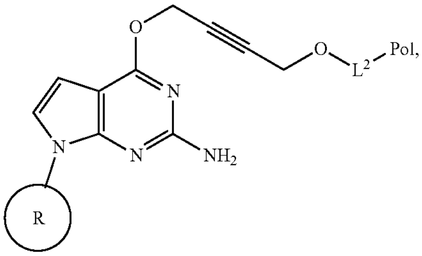
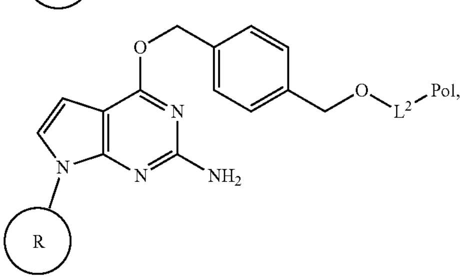
-continued
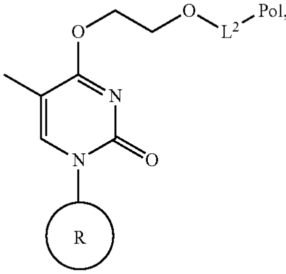
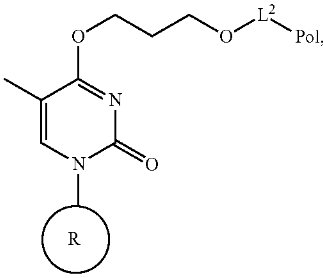
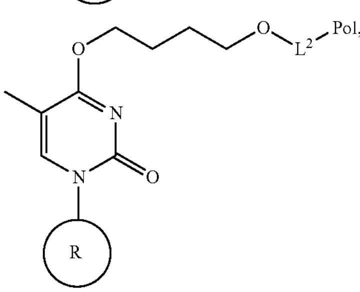
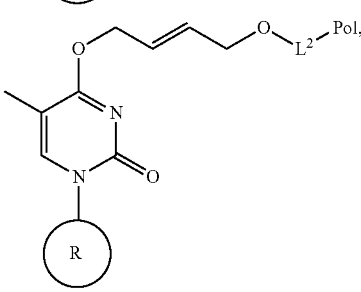
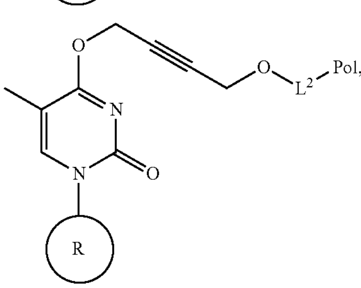
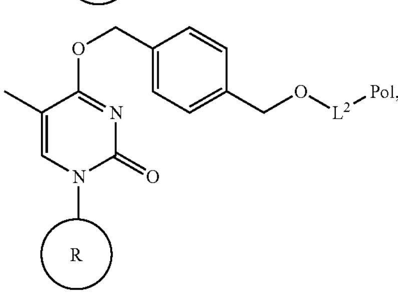

-continued

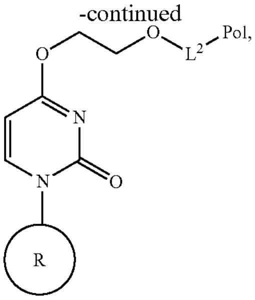

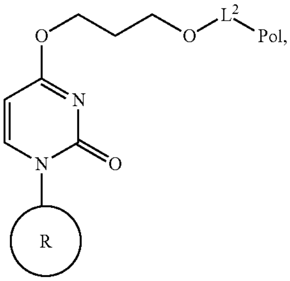

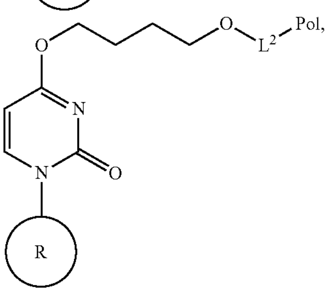

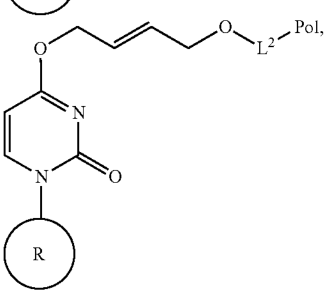

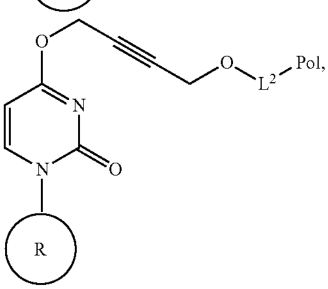

and

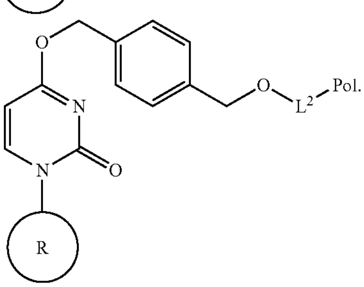

In some embodiments, a ribose polyphosphate is selected from the group consisting of ribose triphosphate, ribose tetraphosphate, ribose pentaphosphate, and ribose hexaphosphate. In some embodiments, a ribose polyphosphate is a ribose triphosphate. In some embodiments, a ribose polyphosphate is a ribose hexaphosphate. In some embodiments, ribose phosphate is a pentaphosphate. In some embodiments, ribose polyphosphate is a ribose tetraphosphate.

Method of Synthesis

In some embodiments, the present disclosure includes a method of treating a polynucleotide synthesized with alkylated nucleobases, comprising:

providing a polynucleotide comprising one or more alkylated nucleobases; and removing one or more alkyl groups from said one or more alkylated nucleobases.

In some embodiments, the present disclosure includes a method of synthesizing a polynucleotide comprising an alkylated nucleobase, comprising:

contacting a precursor polynucleotide with a polymerase and a nucleotide comprising said alkylated nucleobase;

adding said nucleotide to the 3' end of said precursor polynucleotide via said polymerase.

In some embodiments, the present disclosure includes a method of synthesizing a polynucleotide comprising contacting a precursor polynucleotide with a conjugate comprising a nucleotide covalently linked to a polymerase via a cleavable linker, wherein said nucleotide comprises said alkylated nucleobase. In some embodiments, the method of synthesizing a polynucleotide comprises cleaving a cleavable linker after addition of a nucleotide to a precursor polynucleotide. In some embodiments, the method of synthesizing a polynucleotide comprises repeating contacting, adding, and optionally cleaving steps described herein one or more times. In some embodiments, removal of one or more alkyl groups described herein comprises contacting said polynucleotide with an enzyme capable of removing said one or more alkyl groups from said alkylated nucleobases. In some embodiments, a method of synthesizing a polypeptide comprising contacting said polynucleotide with two or more enzymes capable of removing said one or more alkyl groups from said alkylated nucleobases.

In some embodiments, synthesis of a polynucleotide comprises adding nucleotides stepwise to a starter molecule (e.g., an initial oligonucleotide) via the cycled steps of: addition of polymerase-nucleotide conjugate to an oligonucleotide, binding of the nucleotide to the 3' end of the oligonucleotide catalyzed by the polymerase, and cleavage of the polymerase from the added nucleotide. These steps can be repeated until a desired polynucleotide is synthesized. As described herein, the use of nucleotides comprising alkylated nucleobases during polynucleotide synthesis helps to improve the efficiency and accuracy of synthesis by inhibiting secondary structure formation which can interferen with the addition of the incoming nucleotide by the polymerase during synthesis.

Although synthesis can be completed entirely with alkylated nucleotides, synthesis with a combination of unmodified and alkylated nucleotides can also be used effectivley to improve polynucleotide synthesis. In some embodiments, only one of the four nucleotides added (e.g., from G or T) is alkylated during synthesis. In some embodiments, alkylated nucleotides are only added at targeted positions where secondary structure or ternary structure is predicted, which could interfere with synthesis. Such structures can be predicted based on the presence of complementary DNA regions in various ways and respective tools exist, such as the NUPACK algorithms (http://www.nupack.org/home/model). Thus, in some embodiments, synthesis of a completed polynucleotide where synthesis is improved can include the use of only 1 or 2 alkylated nucleotides. In some embodiments, about 5%, about 10%, about 20%, about 30%, about 50%, substantially all, or 100% of a specific nucleotide is incorporated into the polynucleotide in their alkylated version. In some embodiments, less than 5%, less than 10%, less than 20%, less than 30%, or less than 50% of a specific nucleotide is incorporated into the polynucleotide in its alkylated version. In some embodiments, more than 5%, more than 10%, more than 20%, more than 30%, or more than 50% of a specific nucleotide is incorporated into the polynucleotide in its alkylated version. In some embodiments, only alkylated guanine nucleotides are used in the nucleotide synthesis reaction. The removal of alkylations in the terminal positions of a nucleic acid with alkyl transferases may be more challenging than the removal from internal DNA positions. Therefore, in some embodiments, nucleotide synthesis is performed such that the last and first 1, 2, or 3 positions of the synthesized nucleic acid does not comprise alkylated nucleotides.

In some embodiments, the nucleotides analogs described herein comprise a reversible terminator group, such as such as an O— azidomethyl or O—NH2 group on the 3' position of the sugar or an (alpha-tertbutyl-2-nitrobenzyl)oxymethl group on the 5 position of pyrimidines or the 7 position of 7-deazapurines (for an overview see, e.g. Chen et al., Genomics, Proteomics & Bioinformatics 2013 11: 34-40). In these embodiments, the nucleotide analog prevents or hinders further elongation once incorporated into a nucleic acid to achieve controlled termination of synthesis. In some embodiments, when used as part of a conjugate, the RTdNTP-polymerase conjugates do not rely on the shielding effect to achieve termination, e.g. when a 3' modified RTdNTP is tethered to the polymerase, the linker used may exceed 100 Å or 200 Å in length.

O-Alkyl Modified Nucleotides (Synthesis and Structures)

$O^6$-alkylguanine-DNA alkyltransferase (AGT) irreversibly transfers an alkyl group from its substrate, a modified nucleotide. Described herein are alkyl modified nucleotides useful during synthesis, where the alkyl group can be removed by AGT. In some embodiments, this removal converts a 'scarred' nucleotide to a naturally occurring nucleotide or nucleobase in a synthesized oligonucleotide. Several forms of the enzyme can be used considered provided they have similar properties in reacting with an alkyl group substrate (such as human, murine, rat, a chimera, or other species of AGT). The As used herein, the alkyl group refers to any group that can act as a substrate and is removed from the nucleotide by an AGT enzyme.

In the present invention, O6-alkylguanine-DNA alkyltransferase also includes variants of a wild-type AGT which may differ by virtue of one or more amino acid substitutions, deletions or additions, but which still retain the property of transferring a label present on a substrate to the AGT part of the fusion protein. AGT variants may be obtained by chemical modification using techniques well known to those skilled in the art. AGT variants may preferably be produced using protein engineering techniques known to the skilled person and/or using molecular evolution to generate and select new O6-alkylguanine-DNA alkyltransferases. Such techniques are e.g. saturation mutagenesis, error prone PCR to introduce variations anywhere in the sequence, DNA shuffling used after saturation mutagenesis and/or error prone PCR, or family shuffling using genes from several species.

In some embodiments, an alkylated nucleobase is a nucleobase of formula (I) or formula (II):

VI

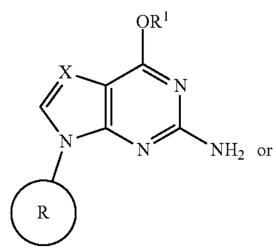

or

VII

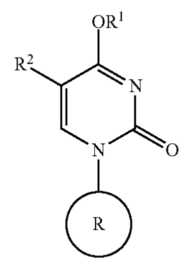

wherein $R^1$ is selected from the group consisting of $C_{1-6}$ alkyl, $C_{2-6}$ alkenyl, $C_{1-6}$ alkynyl, and $—(CH_2)_{0-3}Ph$, wherein $R^1$ is optionally substituted with 1-6 instances of $R^{1a}$;

each $R^{1a}$ is independently selected from halogen, $C_{1-6}$ alkyl, $—(CH_2)_{0-3}OR^{1b}$, $—NO_2$, $—N_3$, $—OPO_2OH$, and $—(CH_2)_{0-3}NHR^{1b}$; and each $R^{1b}$ is independently selected from hydrogen, $C_{1-6}$ alkyl, $—C(O)(C_{1-6}$ alkyl), $C_{1-6}$ haloalkyl, $—C(O)(C_{1-6}$ haloalkyl), and $—CH_2OAc$;

$R^2$ is hydrogen or methyl;

X is —N═ or —C(H)═; and

R is a ribose polyphosphate or deoxyribose polyphosphate.

In some embodiments, X is —C(H)═ or —N═. In some embodiments, X is —C(H)═. In some embodiments, X is —N═.

In some embodiments, $R^1$ is selected from the group consisting of $C_{1-6}$ alkyl, $C_{2-6}$ alkenyl, $C_{1-6}$ alkynyl, and $—(CH_2)_{0-3}Ph$, wherein $R^1$ is optionally substituted with 1-6 instances of $R^{1a}$. In some embodiments, $R^1$ is selected from the group consisting of $C_{2-6}$ alkyl, $C_{2-6}$ alkenyl, $C_{2-6}$ alkynyl, and $—(CH_2)_{0-3}Ph$, wherein $R^1$ is optionally substituted with 1-6 instances of $R^a$. In some embodiments, $R^1$ is selected from the group consisting of $C_{1-3}$ alkyl, $C_{2-4}$ alkenyl, $C_{24}$ alkynyl, and $—CH_2Ph$, wherein $R^1$ is optionally substituted with one instance of $R^a$. In some embodiments, $R^1$ is selected from the group consisting of methyl, ethyl, $C_4$ alkenyl, $C_4$ alkynyl, and $—CH_2Ph$, wherein $R^1$ is optionally substituted with one instance of $R^a$. In some embodiments, $R^1$ is selected from the group consisting of ethyl, $C_4$ alkenyl, $C_4$ alkynyl, and $—CH_2Ph$, wherein $R^1$ is optionally substituted with one instance of $R^a$. In some embodiments, $R^1$ is selected from the group consisting of $C_1$-$C_3$ alkyl, wherein $R^1$ is optionally substituted with 1-3 instances of $R^a$. In some embodiments, $R^1$ is selected from the group consisting of $C_1$-$C_3$ alkyl, wherein $R^1$ is optionally substituted with 1-3 instances of $R^a$.

In some embodiments, $R^1$ is selected from the group consisting of

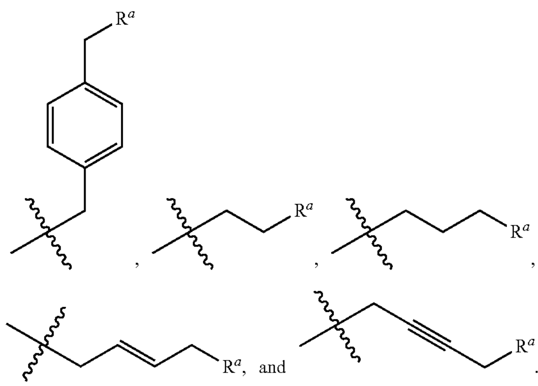

In some embodiments, $R^1$ is selected from the group consisting of methyl, ethyl, and n-propyl optionally substituted with 1-3 instances of $R^a$.

In some embodiments, $R^1$ is methyl.

In some embodiments, the nucleotide is selected from the group consisting of

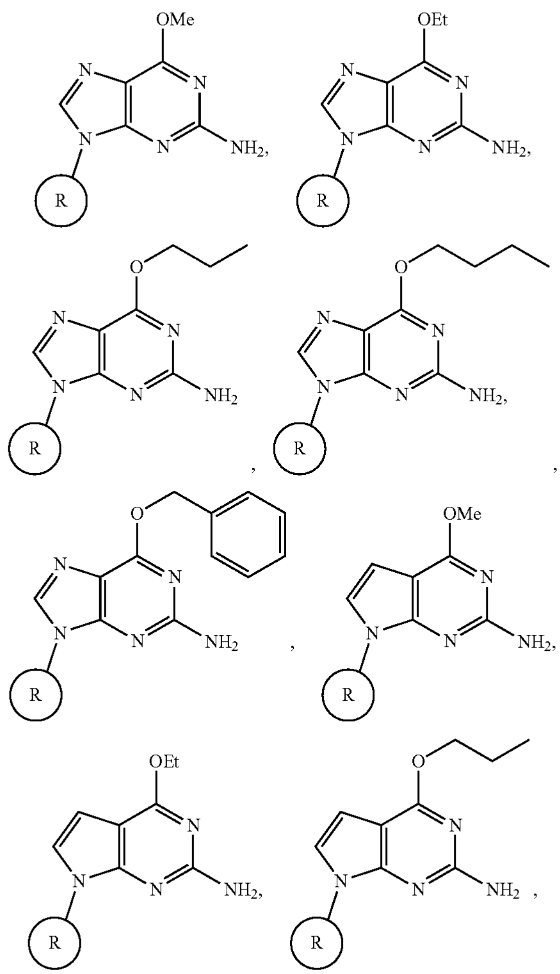

-continued

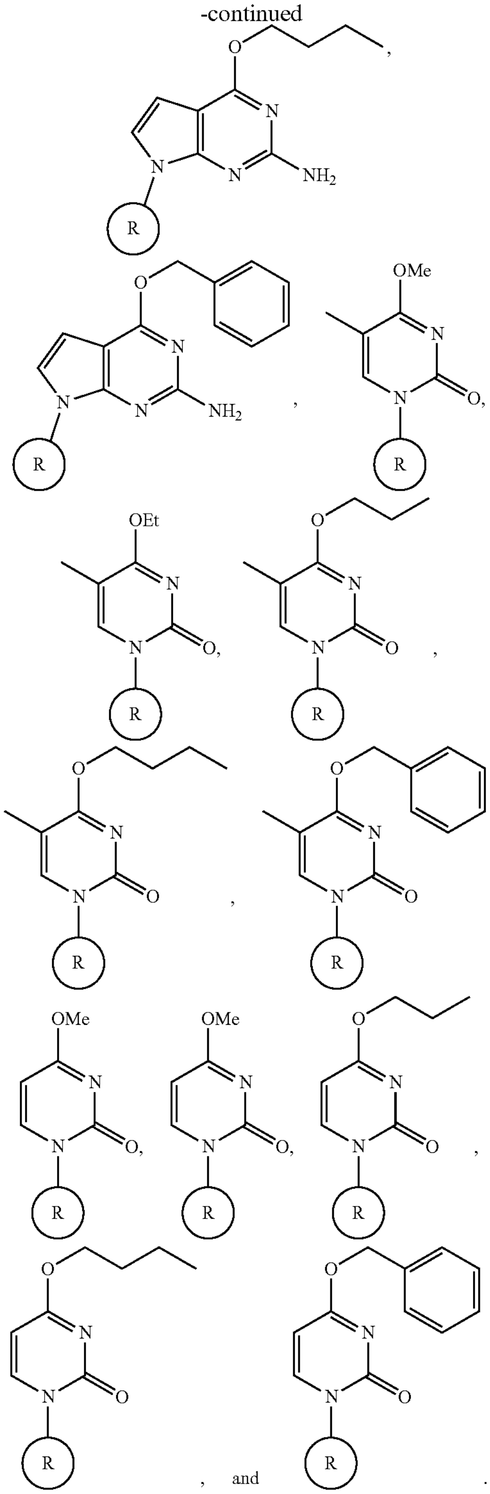

Definitions

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted"

group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH{=}CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR^\circ$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $-SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(halo$R^\bullet$), $-(CH_2)_{0-2}OH$, $-(CH_2)_{0-2}OR^\bullet$, $-(CH_2)_{0-2}CH(OR^\bullet)_2$; $-O$(halo$R^\bullet$), $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, -(halo$R^\bullet$), $-OH$, $-OR^\bullet$, $-O$(halo$R^\bullet$), $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $-C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of Rt, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(halo$R^\bullet$), $-OH$, $-OR^\bullet$, $-O$(halo$R^\bullet$), $-CN$, $-C(O)OH$, $-C(O)OR^\bullet$, $-NH_2$, $-NHR^\bullet$, $-NR^\bullet_2$, or $NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

In an alternative embodiment, compounds described herein may also comprise one or more isotopic substitutions. For example, hydrogen may be $^2H$ (D or deuterium) or $^3H$ (T or tritium); carbon may be, for example, $^{13}C$ or $^{14}C$; oxygen may be, for example, $^{18}O$; nitrogen may be, for example, $^{15}N$, and the like. In other embodiments, a particular isotope (e.g., $^3H$, $^{13}C$, $^{14}C$, $^{18}O$, or $^{15}N$) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Tethered Modified Nucleotides (Synthesis and Structures)

Overview

When a conjugate comprising a polymerase and a nucleoside triphosphate is incubated with a nucleic acid, it preferentially elongates the nucleic acid using its tethered nucleotide (as opposed to using the nucleotide of another conjugate molecule). As described above, the polymerase then remains attached to the nucleic acid via its tether to the added nucleotide until exposed to some stimulus that causes cleavage of the linkage to the added nucleotide. In this situation, further extensions by polymerase-nucleotide conjugates are hindered due to "shielding" when: 1) the attached polymerase molecule hinders other conjugates from accessing the 3' OH of the extended DNA molecule and 2), other nucleoside triphosphates in the system are hindered from accessing the catalytic site of the polymerase that remains attached to the 3' end of the extended nucleic acid. (The extent of shielding may be described as the extent to which both of these interactions are hindered.) To enable subsequent extensions, the linker tethering the incorporated nucleotide to the polymerase can be cleaved, releasing the polymerase from the nucleic acid and therefore re-exposing its 3' OH group for subsequent elongation.

Methods for nucleic acid synthesis provided herein that employ the shielding effect to achieve termination comprise an extension step wherein a nucleic acid is exposed to conjugates preferentially in the absence of free (i.e. untethered) nucleoside triphosphates, because the termination mechanism of shielding may not prevent their incorporation into the nucleic acid.

In some embodiments, termination of further elongation may be "complete", meaning that after a nucleic acid molecule has been elongated by a conjugate, further elongations cannot occur during the reaction. In other embodiments, termination of further elongation may be "incomplete", meaning that further elongations can occur during the reaction but at a substantially decreased rate compared to the initial elongation, e.g., 100 times slower, or 1000 times slower, or 10,000 times slower, or more. Conjugates that achieve incomplete termination may still be used to extend a nucleic acid by predominantly a single nucleotide (e.g. in methods for nucleic acid synthesis and sequencing) when the reaction is stopped after an appropriate amount of time. In some embodiments, the reagent containing the conjugate may additionally contain polymerases without tethered nucleoside triphosphates, but those polymerases should not significantly affect the reaction because there are no free dNTPs in the mix.

Reagents based on conjugates employing the shielding effect to achieve termination preferentially only contain polymerase-nucleotide conjugates in which all polymerases remain folded in the active conformation. In some cases, if the polymerase moiety of a conjugate is unfolded, its tethered nucleoside triphosphate may become more accessible to the polymerase moieties of other conjugate molecules. In these cases, the unshielded nucleotides may be more readily incorporated by other conjugate molecules, circumventing the termination mechanism.

Polymerase-nucleotide conjugates employing the shielding effect to achieve termination are preferentially only labeled with a single nucleoside triphosphate moiety. Polymerase-nucleotide conjugates labeled with multiple nucleoside triphosphates that can access the catalytic site can, in some cases, incorporate multiple nucleoside triphosphates into the same nucleic acid. Additional tethered nucleotides may therefore lead to additional, undesired nucleotide incorporations into a nucleic acid during a reaction. Furthermore, only one tethered nucleoside triphosphates can occupy the (buried) catalytic site of its polymerase at a time so the other tethered nucleoside triphosphate(s) may have an increasing accessibility to the polymerase moieties of other conjugate molecules, as discussed below.

Polymerase-nucleotide conjugates employing the shielding effect to achieve termination preferentially comprise as short of a linker as possible that still enables the nucleoside triphosphate to frequently access the catalytic site of its tethered polymerase molecule in a productive conformation, in order to enable fast incorporation of the nucleotide into a nucleic acid. Such conjugates may also preferentially employ an attachment position of the linker to the polymerase as close to the catalytic site as possible, enabling use of a shorter linker. The length of the linker will determine the maximum distance from the attachment point a tethered nucleoside triphosphate or a tethered nucleic acid can reach. A smaller distance may lead to a reduced accessibility of the tethered moiety to other polymerase-nucleotide molecules, as discussed below. In some embodiments, linkers are approximately 24 and 28 Å long. Shorter linkers, e.g. with lengths of 8-15 Å may increase shielding; longer linkers, e.g. linkers longer than 50 Å, 70 Å or 100 Å, may reduce shielding. The shielding effect may be influenced by a combination of factors including, but not limited to, to the structure of the polymerase, the length of the linker, the structure of the linker, the attachment position of the linker to the polymerase, the binding affinity of the nucleoside triphosphate to the catalytic site of the polymerase, the binding affinity of the nucleic acid to the polymerase, the preferred conformation of the polymerase, and the preferred conformation of the linker.

One contribution to shielding can be steric effects that block the 3' OH of a nucleic acid that has been elongated by a conjugate from reaching into the catalytic site of another conjugate's polymerase moiety. Steric effects may also hinder a tethered nucleoside triphosphate from reaching into the catalytic site of another polymerase-nucleotide conjugate molecule due to clashes between the conjugates that would occur during such approaches. These steric effects may result in complete termination if they completely block productive interactions between the tethered nucleoside triphosphate (or elongated nucleic acid) of one conjugate molecule with another conjugate molecule, or may result in incomplete termination if they only hinder such intermolecular interactions.

Another contribution to shielding arises from the binding affinity of the tethered nucleoside triphosphate to the catalytic site of the polymerase. The tethered nucleoside triphosphate of a conjugate will have a high effective concentration with respect to the catalytic site of its tethered polymerase so it may remain bound to that site much of the time. When the nucleoside triphosphate is bound to the catalytic site of its tethered polymerase molecule it is unavailable for incorporation by other polymerase molecules. Thus, tethering reduces the effective concentration of nucleoside triphosphates available for intermolecular incorporation (i.e. incorporation catalyzed by a polymerase molecule to which the nucleotide is not tethered). This shielding effect can enhance termination by reducing the rate by which a nucleic acid is elongated using the nucleoside triphosphate moiety of one conjugate molecule by the polymerase moiety of another conjugate molecule.

Another contribution to shielding arises from the binding affinity of the 3' region of a nucleic acid molecule to the catalytic site of a polymerase molecule. After elongation by a conjugate, the nucleic acid is tethered to the conjugate via it's 3' terminal nucleotide and will have a high effective concentration with respect to the catalytic site of its tethered polymerase so it may remain bound to that site much of the time. When the nucleic acid is bound to the catalytic site of its tethered polymerase molecule it is unavailable for elongation by other conjugate molecules. This effect can enhance termination by reducing the rate by which a nucleic acid that has been elongated by a first conjugate is further elongated by other conjugate molecules.

In some embodiments, the polymerase-nucleotide conjugates comprise additional moieties that sterically hinder the tethered nucleoside triphosphate (or a tethered nucleic acid post-elongation) from approaching the catalytic sites of another conjugate molecule. Such moieties include polypeptides or protein domains that can be inserted into a loop of the polymerase, and those and other bulky molecules such as polymers that can be site-specifically ligated e.g. to an inserted unnatural amino acid or specific polypeptide tag.

In some embodiments, the linker is attached the 5 position of pyrimidines or the 7 position of 7-deazapurines. In other embodiments, the linker may be attached to an exocyclic amine of a nucleobase, e.g. by N-alkylating the exocyclic amine of cytosine with a nitrobenzyl moiety as discussed below. In other embodiments, the linker may be attached to any other atom in the nucleobase, sugar, or oc-phosphate, as will be apparent to those skilled in the art.

Certain polymerases have a high tolerance for modification of certain parts of a nucleotide, e.g. modifications of the 5 position of pyrimidines and the 7 position of purines are well-tolerated by some polymerases (He and Seela., Nucleic Acids Research 30.24 (2002): 5485-5496.; or Hottin et al., Chemistry. 2017 Feb. 10; 23(9):2109-2118). In some embodiments, the linker is attached to these positions.

In some examples, a polymerase-nucleotide conjugate is prepared by first synthesizing an intermediate compound comprising a linker and a nucleoside triphosphate (referred to herein as a "linker-nucleotide"), and then this intermediate compound is attached to the polymerase. In some examples, nucleosides with substitutions compared to natural nucleosides, e.g. pyrimidines with 5-hydroxymethyl or 5-propargylamino substituents, or 7-deazapurines with 7-hydroxymethyl or 7-propargylamino substituents may be useful starting materials for preparing linker-nucleotides. An exemplary set of nucleosides with 5- and 7-hydroxymethyl substituents that may be useful for preparing linker-nucleotides is shown below:

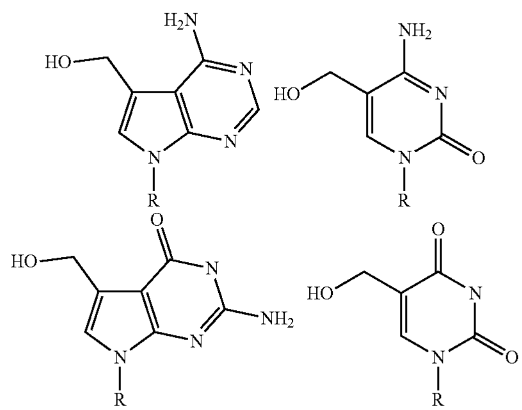

An exemplary set of nucleosides with 5- and 7-deaza-7-propargylamino substituents that may be useful for preparing linker-nucleotides is shown below:

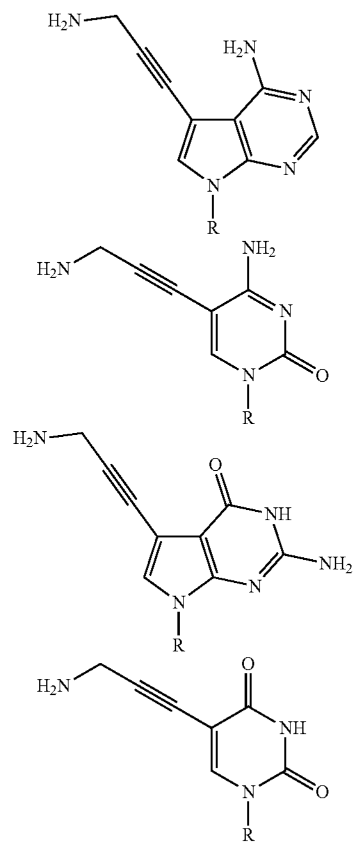

These nucleosides are also commercially available as deoxyribonucleoside triphosphates.

Attachment of a Linker to a Polymerase

In some embodiments, the tethered nucleoside triphosphate may be specifically attached to a cysteine residue of the polymerase using a sulfhydryl-specific attachment chemistry. Possible sulfhydryl specific attachment chemistries include, but are not limited to ortho-pyridyl disulfide (OPSS), maleimide functionalities, 3-arylpropiolonitrile functionalities, allenamide functionalities, haloacetyl functionalities such as iodoacetyl or bromoacetyl, alkyl halides or perfluroaryl groups that can favorably react with sulfhydryls surrounded by a specific amino acid sequence (Zhang, Chi, et al. Nature chemistry 8, (2015) 120-128.). Other attachment chemistries for specific labeling of cysteine residues will be apparent to those skilled in the art or are described in the pertinent literature and texts (e.g., Kim, Younggyu, et al, Bioconjugate chemistry 19.3 (2008): 786-791.).

In other embodiments, the linker could be attached to a lysine residue via an amine-reactive functionality (e.g. NHS esters, Sulfo-NHS esters, tetra- or pentafluorophenyl esters, isothiocyanates, sulfonyl chlorides, etc.). In other embodiments, the linker may be attached to the polymerase via attachment to a genetically inserted unnatural amino acid, e.g. p-propargyloxyphenylalanine or p-azidophenylalanine that could undergo azide-alkyne Huisgen cycloaddition, though many suitable unnatural amino acids suitable for site-specific labeling exist and can be found in the literature (e.g. as described in Lang and Chin., Chemical reviews 114.9 (2014): 4764-4806.).

In other embodiments, the linker may be specifically attached to the polymerase N-terminus. In some embodiments, the polymerase is mutated to have an N-terminal serine or threonine residue, which may be specifically oxidized to generate an N-terminal aldehyde for subsequent coupling to e.g. a hydrazide. In other embodiments, the polymerase is mutated to have an N-terminal cysteine residue that can be specifically labeled with an aldehyde to form a thiazolidine. In other embodiments, an N-terminal cysteine residue can be labeled with a peptide linker via Native Chemical Ligation.

In other embodiments, a peptide tag sequence may be inserted into the polymerase that can be specifically labeled with a synthetic group by an enzyme, e.g. as demonstrated in the literature using biotin ligase, transglutaminase, lipoic acid ligase, bacterial sortase and phosphopantetheinyl transferase (e.g. as described in refs. 74-78 of Stephanopoulos & Francis Nat. Chem. Biol. 7, (2011) 876-884).

In other embodiments, the linker is attached to a labeling domain fused to the polymerase. For example, a linker with a corresponding reactive moiety may be used to covalently label SNAP tags, CLIP tags, HaloTags and acyl carrier protein domains (e.g. as described in refs. 79-82 of Stephanopoulos & Francis Nat. Chem. Biol. 7, (2011) 876-884).

In other embodiments, the linker is attached to an aldehyde specifically generated within the polymerase, as described in Carrico et al. (Nat. Chem. Biol. 3, (2007) 321-322). For example, after insertion of an amino acid sequence that is recognized by the enzyme formylglycine-generating enzyme (FGE) into the polymerase, it may be exposed to FGE, which will specifically convert a cysteine residue in the recognition sequence to formylglycine (i.e. producing an aldehyde). This aldehyde may then be specifically labeled with e.g. a hydrazide or aminooxy moiety of a linker.

In some embodiments, a linker may be attached to the polymerase via non-covalent binding of a moiety of the linker to a moiety fused to the polymerase. Examples of such attachment strategies include fusing a polymerase to streptavidin that can bind a biotin moiety of a linker, or fusing a polymerase to anti-digoxigenin that can bind a digoxigenin moiety of a linker. In some embodiments, site-specific labeling may lead to an attachment of the linker to the polymerase that may readily be reversed (e.g. an ortho-pyridyl disulfide (OPSS) group that forms a disulfide bond with a cysteine that can be cleaved using reducing agents, e.g. using TCEP), other attachment chemistries will produce permanent attachments.

In any embodiment, the polymerase may be mutated to ensure specific attachment of the tethered nucleotide to a particular location of the polymerase, as will be apparent to those skilled in the art. For example, with sulfhydryl-specific attachment chemistries such as maleimides or ortho-pyridyl disulfides, accessible cysteine residues in the wild-type polymerase may be mutated to a non-cysteine residue to prevent labeling at those positions. On this "reactive cysteine-free" background, a cysteine residue may be introduced by mutation at the desired attachment position. These mutations preferentially do not interfere with the activity of the polymerase.

Other strategies for site-specific attachment of synthetic groups to proteins will be apparent to those skilled in the art and are reviewed in literature, (e.g. Stephanopoulos & Francis Nat. Chem. Biol. 7, (2011) 876-884).

Types of Polymerases

In any embodiment, the polymerase can be a template-independent polymerase, i.e., a terminal deoxynucleotidyl transferase or DNA nucleotidylexotransferase, which terms are used interchangeably to refer to an enzyme having activity 2.7.7.31 using the IUBMB nomenclature. A description of such enzymes can be found in Bollum, F. J.

Deoxynucleotide-polymerizing enzymes of calf thymus gland. V. Homogeneous terminal deoxynucleotidyl transferase. J. Biol. Chem. 246 (1971) 909-916; Gottesman, M. E. and Canellakis, E. S. The terminal nucleotidyltransferases of calf thymus nuclei. J. Biol.

Chem. 241 (1966) 4339-4352; and Krakow, J. S., Coutsogeorgopoulos, C. and Canellakis, E. S. Studies on the incorporation of deoxyribonucleic acid. Biochim. Biophys. Acta 55 (1962) 639-650, among others.

In some embodiments, for use with free RTdNTPs, the polymerase is mutated to improve addition of the modified nucleotide.

Linker

In a conjugate, the linker is considered to be at least the atoms that connect the nucleotide to the polymerase. In some embodiments, the linker comprises atoms that connect the base, the sugar, or the α-phosphate of a nucleotide to the polymerase. In some embodiments, the polymerase and the nucleotide are covalently linked and the distance between the linked atom of the nucleotide and the polymerase to which it is attached may be in the range of 4-100 Å, e.g., 15-40 or 20-30 Å, although this distance may vary depending on where the nucleoside triphosphate is tethered. In some embodiments, the linker may be a PEG or polypeptide linker, although, again, there is considerable flexibility on the type of linker used. In some embodiments, the linker should be joined to the base of the nucleotide at an atom that is not involved in base pairing. In such embodiments, the linker is considered to be at least the atoms that connect a Ca atom in the backbone of the polymerase to any atom in the monocyclic or polycyclic ring system bonded to the Γ position of the sugar (e.g. pyrimidine or purine or 7-deazapurine or 8-aza-7-deazapurine). In other embodiments, the linker should be joined to the base of the nucleotide at an atom that is involved in base pairing. In other embodiments, the linker should be joined to the sugar or to the oc-phosphate of the nucleotide. In all embodiments, the linker used should be sufficiently long to allow the nucleoside triphosphate to access the active site of the polymerase to which it is tethered. As will be described in greater detail below, the polymerase of a conjugate is capable of catalyzing the addition of the nucleotide to which it is linked onto the 3' end of a nucleic acid.

Cleavage of Linker

As described above, the linker may be attached to various positions on the nucleotide, and a variety of cleavage strategies may be used. Those strategies may include, but are not limited to, the following examples:

In some embodiments, the linker may be cleaved by exposure to a reducing agent such as dithiothreitol (DTT). For example, a linker comprising a 4-(disulfaneyl)butanoyloxy-methyl group attached to the 5 position of a pyrimidine or the 7 position of a 7-deazapurine may be cleaved by reducing agents (e.g. DTT) to produce a 4-mercaptobutanoyloxymethyl scar on the nucleobase. This scar may undergo intramolecular thiolactonization to eliminate a 2-oxothiolane, leaving a smaller hydroxymethyl scar on the nucleobase. An example of such a linker attached to the 5 position of cytosine is depicted below, but the strategy is applicable to any suitable nucleobase:

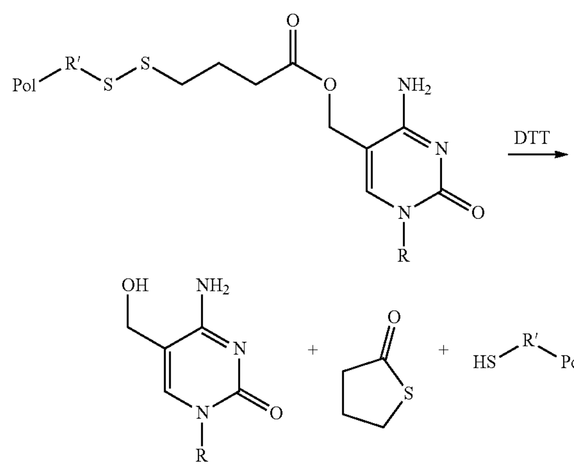

In other embodiments, the linker may be cleaved by exposure to light. For example a linker comprising (2-nitrobenzyl)oxymethyl group may be cleaved with 365 nm light, leaving a hydroxymethyl scar, e.g. as depicted for cytosine below, but as is applicable to any suitable nucleobase:

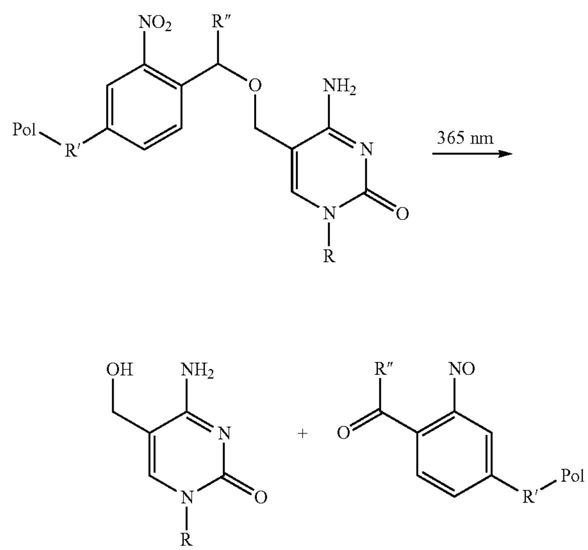

(where, e.g., R"═H or R"═$CH_3$ or R'=i-Bu.)

In other embodiments, the linker may comprise a 3-(((2-nitrobenzyl)oxy)carbonyl)aminopropynyl group that may be cleaved with 365 nm light release a nucleobase with a propargylamino scar. This strategy is applicable to any suitable nucleobase:

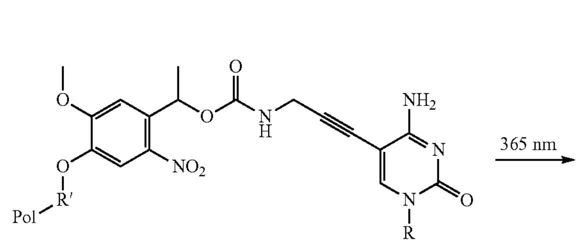

-continued

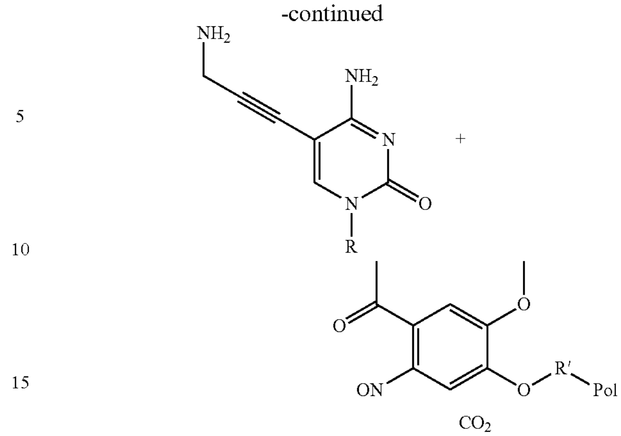

In other embodiments, the linker may comprise an acyloxymethyl group that may be cleaved with a suitable esterase to release a nucleobase with a hydroxymethyl scar, e.g. as depicted for cytosine below, but as is applicable to any suitable nucleobase:

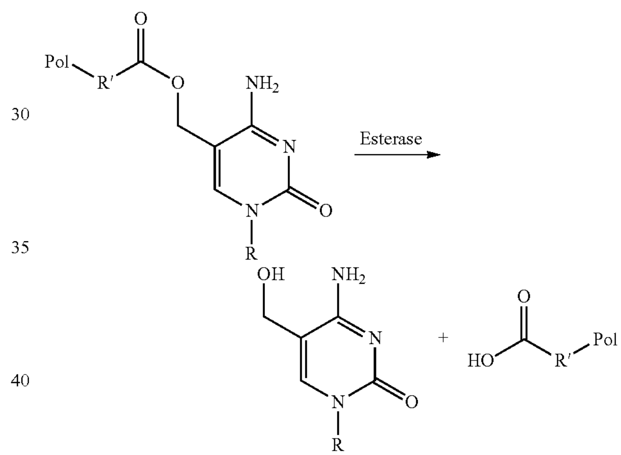

In such embodiments, the linker may comprise additional atoms (included in R' above) adjacent to the ester that increase the activity of the esterase towards the ester bond.

In other embodiments, the linker may comprise an N-acyl-aminopropynyl group that may be cleaved with a peptidase to release a nucleobase with propargylamino scar, e.g. as depicted for 5-propargylamino cytosine below, but as is applicable to any suitable nucleobase:

In such embodiments, the linker may comprise additional atoms (included in R' above)

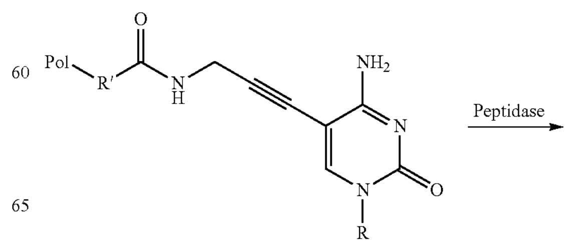

-continued

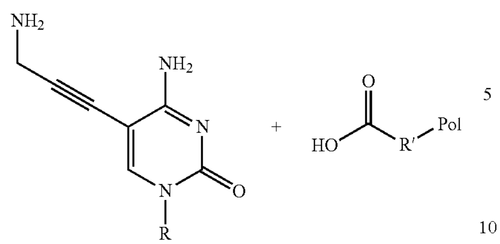

adjacent to the amide that increase the activity of the peptidase towards the amide bond.

In some embodiments, a polymerase-nucleotide conjugate comprises a nucleotide linked to a polymerase using an enzymatically cleavable linker. In some embodiments, a polymerase-nucleotide conjugate comprising an enzymatically cleavable linker comprises a structure Nuc-$L^1$-$L^2$-Pol, wherein Nuc represents a nucleotide, pol represents a polymerase, and $L^1$-$L^2$ represents an enzymatically cleavable linker. In some embodiments, $L^1$ represents a region of an enzymatically cleavable linker connecting the nucleotide to $L^2$, $L^2$ represents a cleavable portion of an enzymatically cleavable linker. In some embodiments, $L^2$ also comprises a portion for connecting $L^2$ to Pol.

In some embodiments, an enzymatically cleavable linker comprises an amino acid ester moiety. In some embodiments, $L^2$ comprises an amino acid ester moiety. In some embodiments, the ester group of an amino acid ester moiety is cleavable by a protease comprising esterase activity. The ester of an amino acid of $L^2$ is attached to $L^1$, which can also be referred to as a spacer or as a scar of a nucleotide after cleavage of the $L^2$ ester. In some embodiments, $L^2$ comprises attachment chemistry for polymerase conjugation. In some embodiments, $L^2$ further comprises additional amino acids bound to the amine of the amino acid ester to serve as a protease substrate. In some embodiments, $L^2$ is optimized for ester stability to prevent spontanous cleavage while retaining the ability to act as a suitable substrate for esterase activity of a protease comprising esterase activity.

In some embodiments, the amino acid ester comprises one or more substitutions at the alpha carbon, such as addition of an aliphatic or bulky substituent. In some embodiments, the amino acid ester is represented by:

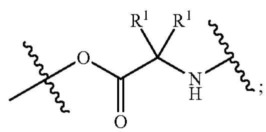;

wherein $R^1$ and $R^{1'}$ are each independently selected from an optionally substituted $C_{1-3}$ alkyl, a halogen, or are optionally taken together with the atom on which they are attached to form an optionally substituted $C_3$-$C_7$ carbocyclic ring.

Exemplary $L^2$ linker structures with different substituents on the alpha carbon of the amino acid ester (e.g., to improve stability of the ester) are shown below (with $L^3$ representing a portion of the $L^2$ linker including attached to the polymerase):

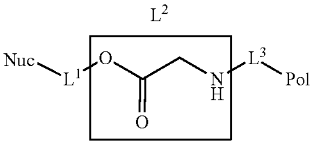

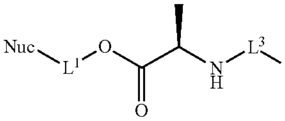,

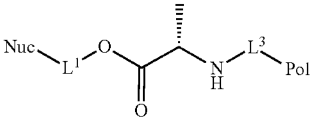

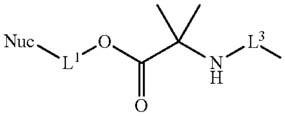,

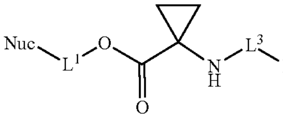,

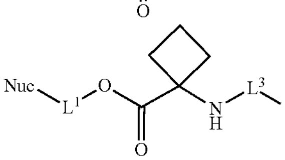,

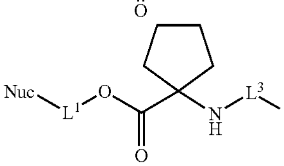,

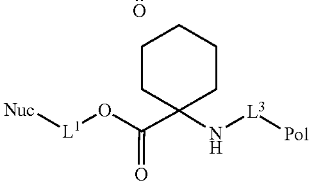

In some embodiments, $L^2$ comprises an amino acid ester adjacent to one or more amino acid residues. In some embodiments, the one or more amino acid residues are bound to the amine group of the amino acid ester.

In some embodiments, $L^2$ comprises or consists of:

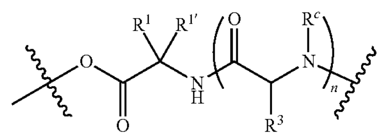

wherein $R^1$ and $R^{1'}$ are independently selected from hydrogen or an optionally substituted $C_{1-3}$ alkyl or are taken together with the atom on which they are attached to form an optionally substituted $C_3$-$C_7$ carbocyclic ring;

each $R^3$ is an optionally substituted group independently selected from hydrogen, $C_{1-6}$ alkyl, benzyl, —OH, —O($C_{1-6}$ alkyl), and —CN;

each $R^c$ is hydrogen or optionally substituted $C_{1-6}$ alkyl; and n is 1, 2, or 3.

In some embodiments, the one or more amino acids linked to the amine of the amino acid ester comprise L- or D-isomers of amino acid residues. The term "naturally-occurring amino acid" refer to Ala, Asp, Cys, Glu, Phe, Gly, His, He, Lys, Leu, Met, Asn, Pro, Gin, Arg, Ser, Thr, Val, Trp, Tyr, or citrulline. "D-" designates an amino acid having the "D" (dextrorotary) configuration, as opposed to the configuration in the naturally occurring ("L-") amino acids. The amino acids described herein can be purchased commercially (Sigma Chemical Co., Advanced Chemtech) or synthesized using methods known in the art. In some embodiments, amino acids with non-natural or artificial side chains are linked to the amine of the amino acid ester.

The one or more amino acids included in the $L^2$ portion of the linker/bound to the amino acid ester can be selected, for example, to optimize protease binding and ester cleavage. A combinatorial library can be generated to test optimal cleavage activity, amino acids can be chosen based on existing known peptide sequence targets for the protease. The protease comprising esterase activity can recognize the peptide portion of the linker and hydrolyzes the ester group of the amino acid ester of $L^2$, resulting in removal of polymerase attached to the nucleotide via the linker, as disclosed herein.

If desired, a spacer can be used between the nucleotide and the linker, or between the linker and the label. Different lengths of spacers can be used in order to increase $L^2$ availability towards the protease/esterase and increase the efficiency and fidelity of polymerases. Exemplary spacers include, for example, polyethyleneglycol or other suitable spacers.

Examples of linkers comprising $L^2$ structures including an amino acid ester bound to one or more amino acid residues is shown below, with '$L^3$' representing a portion of the $L^2$ cleavable linker that is capable of binding to the polymerase:

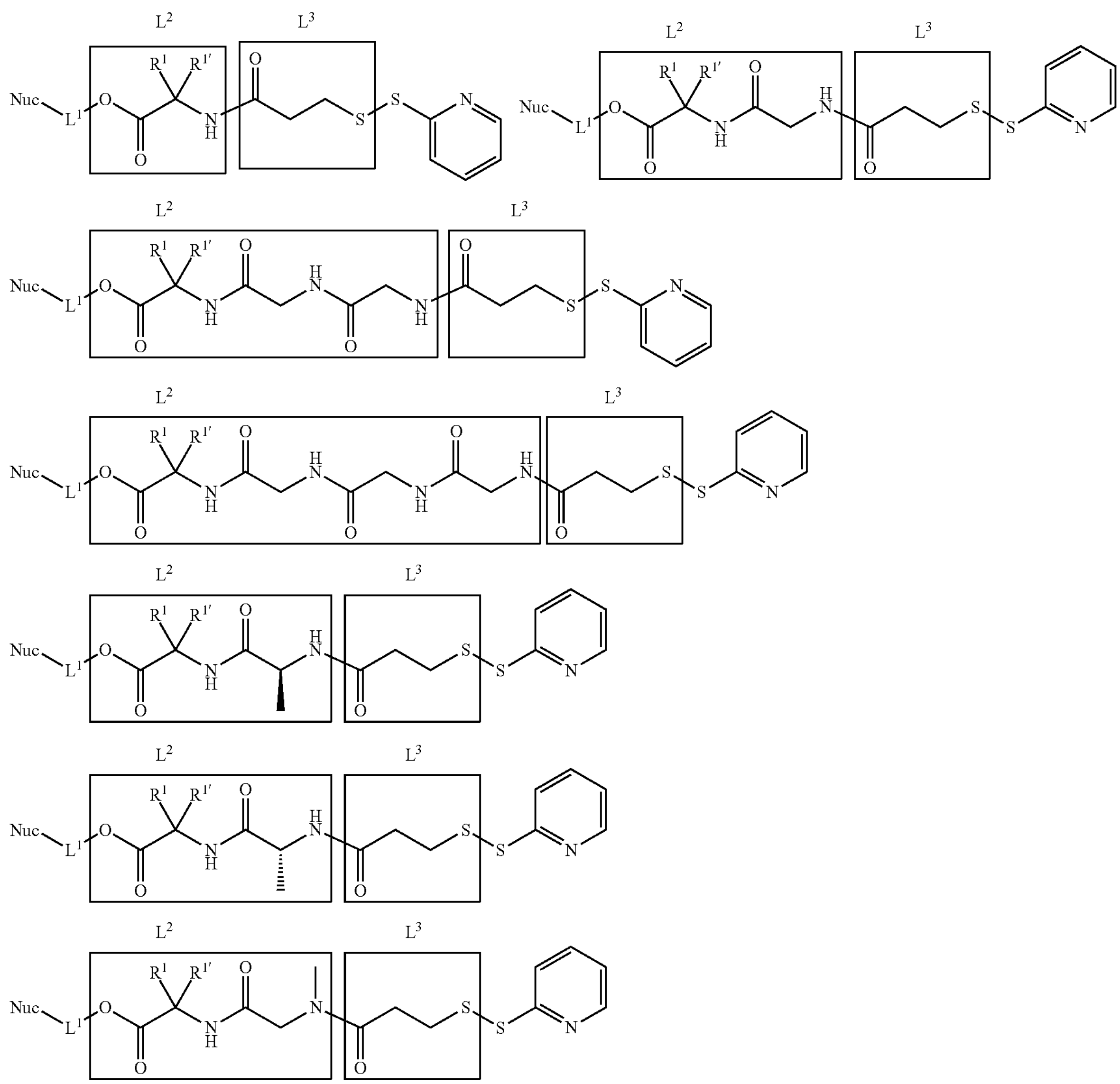

There is considerable flexibility on the type of linker used for regions of the linker not associated with enzymatic cleavage disclosed herein. Examples of suitable linker structures may include, but are not limited to, carbon-chain linkers (e.g., C6, C12, C18, C24, etc.), peptide linkers (e.g., poly-glycine or poly-alanine ranging from about 1 residue to about 1,000 residues in length), or polyether linkers (e.g., PEG, PPG, PAG, PTMG from about 1 polyether unit to about 1,000 polyether units in length).

In some embodiments, the linker comprises a chain of atoms selected from C, N, O, S, Si, and P, preferably having 0-500 atoms, wherein $L^1$ covalently connects to Nuc and $L^2$, and wherein $L^2$ is covalently attached to Pol. The atoms used in forming $L^1$ or including in $L^2$ (e.g., in $L^3$ shown above) may be combined in all chemically relevant ways, such as forming alkylene, alkenylene, and alkynylene, carbamates, carbonates, ethers, polyoxyalkylene, esters, amines, imines, polyamines, hydrazines, hydrazones, amides, ureas, semi-carbazides, carbazides, alkoxyamines, alkoxylamines, urethanes, amino acids, peptides, acyloxylamines, hydroxamic acids, or combination above thereof.

In some embodiments, the linker comprises one or more carbon atoms, zero, one, or more oxygen atoms, zero, one or more nitrogen atoms, zero, one, or more sulfur atoms, or a combination thereof, in different embodiments. In some embodiments, the linker comprises, comprises about, comprises at least, comprises at least about, comprises at most, or comprises at most about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values, carbon atom(s), oxygen atom(s), nitrogen atom(s), sulfur atom(s), or a combination thereof.

In some embodiments, the linker comprises a polymer, such as a homopolymer or a heteropolymer. In some embodiments, the linker comprise a plurality of repeat units. In some embodiments, the plurality of repeating units comprises identical repeating units. In some embodiments, the plurality of repeating units comprises two or more different repeating units. The plurality of repeating units can comprise a polyether such as paraformaldehyde, polyethylene glycol (PEG), polypropylene glycol (PPG), polyalkylene glycol (PAG), polytetramethylene glycol (PTMG), or a combination thereof. For example, the plurality of repeating units can comprise PEGix, PEG23, PEG24, or a combination thereof. The plurality of repeating units can comprise a polyalkylene, such as polyethene, polypropene, polybutene, or a combination thereof. In some embodiments, a repeating unit of the plurality of repeating units comprises no aromatic group. In some embodiments, a repeating unit of the plurality of repeating units comprises one or more aromatic groups.

In some embodiments, the linker comprises any number of basic chemical starting blocks. For example, linkers may comprise linear or branched alkyl, alkenyl, or alkynyl chains, or combinations thereof, that provide a useful distance between the nucleotide and polymerase, the nucleotide and $L^2$, or the polymerase and the cleavable moiety of $L^2$. For instance, amino-alkyl linkers, e.g., amino-hexyl linkers, have been used to attach linkers to nucleotide analogs, and are generally sufficiently rigid to maintain such distances. The longest chain of such linkers may include as many as 2 atoms, 3 atoms, 4 atoms, 5 atoms, 6 atoms, 7 atoms, 8 atoms, 9 atoms, 10 atoms, or even 11-35 atoms, or even 35-50 atoms. The linear or branched linker may also contain heteroatoms other than carbon, including, but not limited to, oxygen, sulfur, phosphate, and nitrogen. A polyoxyethylene chain (also commonly referred to as polyethyleneglycol, or PEG) is a preferred linker constituent due to the hydrophilic properties associated with polyoxyethylene. Insertion of heteroatom such as nitrogen and oxygen into the linkers may affect the solubility and stability of the linkers.

The linker may be rigid in nature or flexible. Rigid structures include laterally rigid chemical groups, e.g., ring structures such as aromatic compounds, multiple chemical bonds between adjacent groups, e.g., double or triple bonds, in order to prevent rotation of groups relative to each other, and the consequent flexibility that imparts to the overall linker. Thus, the degree of desired rigidity may be modified depending on the content of the linker, or the number of bonds between the individual atoms comprising the linker. Further, addition of ringed structures along the linker may impart rigidity. Ringed structures may include aromatic or non-aromatic rings. Rings may be anywhere from 3 carbons, to 4 carbons, to 5 carbons or even 6 carbons in size. Rings may also optionally include heteroatoms such as oxygen or nitrogen and also be aromatic or non-aromatic. Rings may additionally optionally be substituted by other alkyl groups and/or substituted alkyl groups.

Linkers that comprise ring or aromatic structures can include, for example aryl alkynes and aryl amides. Other examples of the linkers of the disclosure include oligopeptide linkers that also may optionally include ring structures within their structure.

In embodiments, the linker comprises is a $C_1$-$C_{10}$ alkylene chain, wherein 1-6 methylene units are optionally and independnetly replaced by —NH—, —O—, —C(O)—, —C(O)NH—, —NHC(O)—, —NHC(O)NH—, —C(O)O—, —OC(O)—, —SS—, optionally substituted cycloalkylene (e.g., $C_3$-$C_8$, $C_3$-$C_6$, or $C_5$-$C_6$), optionally substituted heterocycloalkylene (e.g., 3 to 8, 3 to 6, or 5 to 6 membered), optionally substituted arylene (e.g., $C_6$-$C_{10}$, $C_{10}$, or phenylene), or substituted or unsubstituted heteroarylene (e.g., 5 to 10, 5 to 9, or 5 to 6 membered).

In some embodiments, $L^1$ is a bond, —NH—, —O—, —C(O)—, —C(O)NH—, —NHC(O)—, —NHC(O)NH—, —C(O)O—, —OC(O)—, —SS—, optionally substituted alkylene (e.g., $C_1$-$C_{20}$, $C_{10}$-$C_{20}$, $C_1$-$C_8$, $C_1$-$C_6$, or $C_1$-$C_4$), optionally substituted heteroalkylene (e.g., 2 to 20, 8 to 20, 2 to 10, 2 to 8, 2 to 6, or 2 to 4 membered), optionally substituted cycloalkylene (e.g., $C_3$-$C_8$, $C_3$-$C_6$, or $C_5$-$C_6$), optionally substituted heterocycloalkylene (e.g., 3 to 8, 3 to 6, or 5 to 6 membered), optionally substituted (e.g., $C_6$-$C_{10}$, $C_{10}$, or phenylene), or optionally substituted (e.g., 5 to 10, 5 to 9, or 5 to 6 membered). In some embodiments, $L^1$ is optionally substituted $C_1$-$C_{20}$ alkylene. In some embodiments, $L^1$ is optionally substituted 2 to 20 membered heteroalkylene. In some embodiments, $L^1$ is optionally substituted $C_3$-$C_8$ cycloalkylene. In some embodiments, $L^1$ is optionally substituted 3 to 8 membered heterocycloalkylene. In embodiments, $L^1$ is optionally substituted $C_6$-$C_{10}$ arylene. In embodiments, $L^1$ is optionally substituted 5 to 10 membered heteroarylene.

In some embodiments, $L^1$ is substituted with 1-6 instances of $R^L$. Each $R^L$ is independently selected from the group consisting of oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_2$, —$OCHCI_2$, —$OCHBr_2$, —OCHb, —$OCHF_2$, —$N_3$, optionally substituted alkyl (e.g., $C_1$-$C_{20}$, $C_{10}$-$C_{20}$, $C_1$-$C_8$, $C_1$-$C_6$, or $C_1$-$C_4$), optionally substituted heteroalkyl (e.g., 2 to 20, 8 to 20, 2 to 10, 2 to 8, 2 to 6, or 2 to 4 membered), optionally substituted cycloalkyl (e.g., $C_3$-$C_8$, $C_3$-$C_6$, or $C_5$-$C_6$), optionally substituted heterocycloalkyl (e.g., 3 to 8, 3 to 6, or 5 to 6 membered), optionally substituted aryl (e.g., $C_6$-$C_{10}$, $C_{10}$, or phenyl), and optionally substituted heteroaryl (e.g., 5 to 10, 5 to 9, or 5 to 6 membered).

In some embodiments, L1 acts as an attachment point to the nucleotide and includes a hydroxyl terminal group which binds to a portion of L2 during synthesis.

As described herein, in some embodiments, L1 is a scar that is enzymatically cleavable after cleavage of polymerase-nucleotide linker/removal of the L2-pol moiety.

In some embodiments, L2 comprises a bioconjugate group suitable for conjugation of L2 to the polymerase.

In some embodiments, the bioconjugate group is an N-hydroxysuccinimide ester (NHS) group. In some embodiments, the bioconjugate group is a maleimide group. The linker may then be covalently attached to the polymerase by reaction of the maleimide group with a cysteine residue of the polymerase.

In some embodiments, the polymerase may be operably linked to a linker moiety including a covalent or non-covalent bond; amino acid tag (e.g., poly-amino acid tag, poly-His tag, 6His-tag (SEQ ID NO: 31)); chemical compound (e.g., polyethylene glycol); protein-protein binding pair (e.g., biotin-avidin); affinity coupling; capture probes; or any combination of these. The linker moiety can be separate from or part of a polymerase variant.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols A and B(1992).

Example 1: PolyG Oligonucleotide Synthesis with dGTP and O6-Methyl dGTP

In this example, we tested an extension reaction performed by TDT and either dGTP nucleotides or O6-methyl dGTP nucleotides to synthesize a polyG sequence.

Extension reactions were performed with the following reagents: 250 nM "02-64" DNA oligo with 5' fluorescein and sequence T35 purchased from IDT ("T35" disclosed as SEQ ID NO: 32), 1× Cutsmart Buffer (New England Biolabs), 0.25 mM $CoCl_2$ (New England Biolabs), 1 units/μL of terminal transferase (New England Biolabs), 1 mM of "dG" (deoxyguanosine triphosphate) or 1 mM of "O6m-dG" (O6-Methyl-deoxyguanosine triphosphate).

Reactions were incubated at 37 degrees Celsius at various timepoints (30 seconds, 1 minute, 2 minutes, 4 minutes, or 8 minutes) until the reactions were stopped by the addition of 40 mM ethylenediaminetetraacetic acid. Oligonucleotides were analyzed by capillary electrophoresis.

Figure 4:
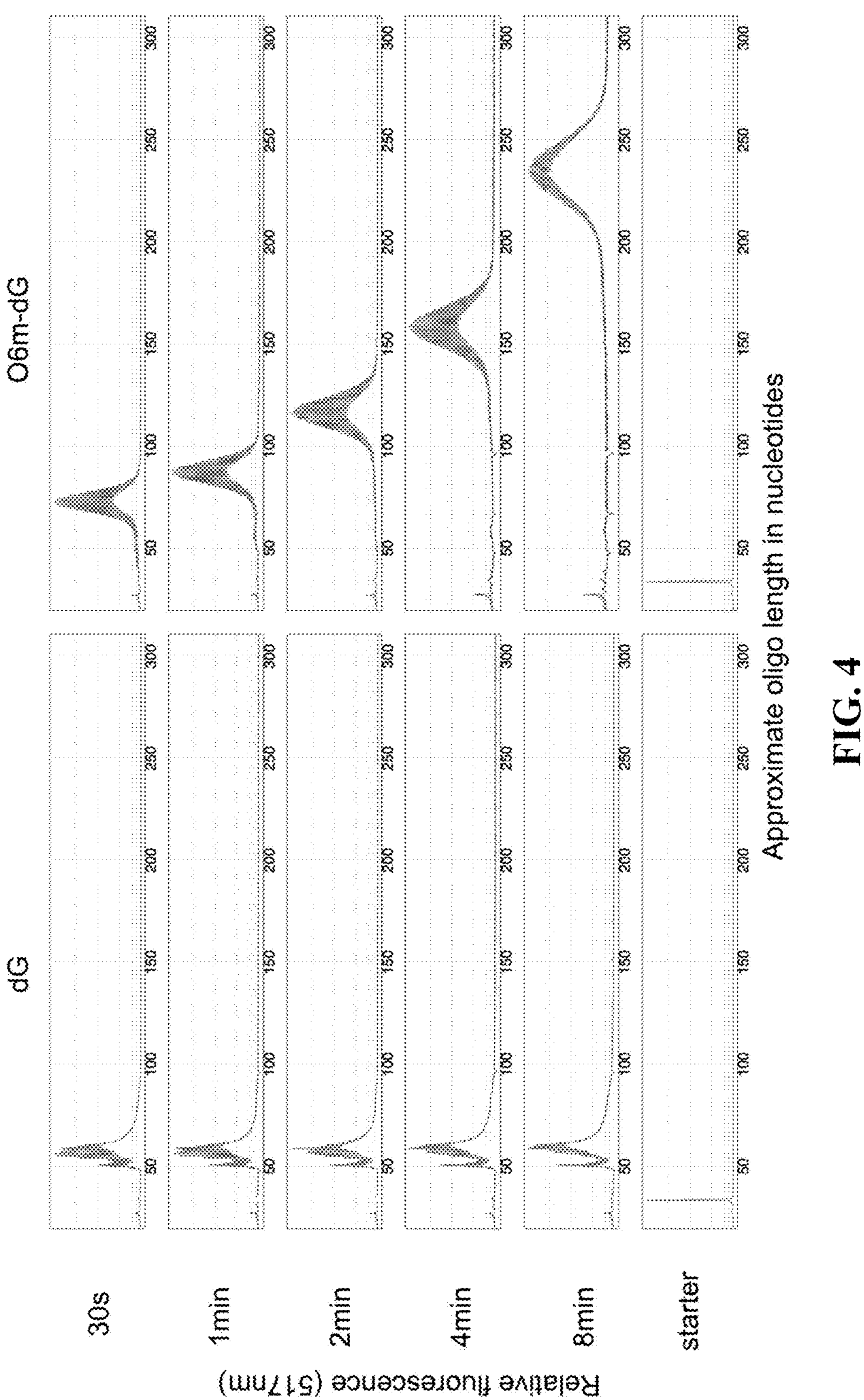
FIG. 4 shows the results of extension reactions with TdT and i) dGTP (left column) and ii) O6-methyl dGTP (right column) performed for 30 seconds, 1 minute, 2 minutes, 4 minutes, or 8 minutes as described in Example 1. The starter is unmodified 02-64 oligo. The x-axis is the approximate oligo length in nucleotides and the y-axis is relative fluorescence of fluorescein at 517 nm.

Result: FIG. 4 shows the results of extension reactions performed for 30 seconds, 1 minute, 2 minutes, 4 minutes, or 8 minutes with dG (left column) or O6m-dG (right column). Starter is unmodified 02-64 oligo. In FIG. 4, the x-axis is the approximate oligo length in nucleotides and the y-axis is relative fluorescence of fluorescein at 517 nm. Extension reaction with TdT and dGTP produces short products where extension stalls (as G-quadruplexes form). In contrast, extension with dGTP having an alkylation at the O6-position (O6-methyl dGTP, purchased from Trilink) shows robust and continuous extension without stalling.

Thus, use of modified nucleotides, such as O6-methyl dGTP, improves polynucleotide synthesis and inhibits secondary structure formation.

Example 2. Preparation of Polymerase-Nucleotide Conjugates

1. Generation of Polymerase (TdT) Mutants with Various Attachment Positions for the Linker An inducible plasmid expressing murine TdT with a single cysteine located at position 182 was produced (see Palluk et al., Nature Biotechnology, 2018 for complete protocol). Also see US Patent Publication No. 2019/0112627, "Nucleic Acid Synthesis and Sequencing Using Tethered Nucleoside Triphosphates" for further details of polymerase-nucleotide conjugate preparation, incorporated by reference herein in its entirety.

2. Protein Expression and Purification of the Mutants

TdT expression was performed using BL21 (DE3) Gold cells (Agilent) in TB media containing antibiotics for resistance marker of the plasmid. An overnight culture of 50 mL was used to inoculate a 400 mL expression culture with 1/20 vol. Cells were grown at 37° C. and 200 rpm shaking until they reached OD 0.6. IPTG was added to a final concentration of 0.5 mM and the expression was performed for 16-20 h at 16° C. Cells were harvested by centrifugation at 8000 G for 10 min and resuspended in 20 mL buffer A (20 mM Tris-HCl, 0.5 M NaCl, pH 8)+5 mM imidazole. Cell lysis was performed using sonication followed by centrifugation at 30,000 G for 20 min. The supernatant was applied to a gravity column containing 1 mL of Ni-NTA agarose (Qiagen). The column was washed with 20 volumes of buffer A+40 mM imidazole, and bound protein was eluted using 4 mL buffer A+500 mM imidazole. The protein was concentrated to ~0.15 mL with Vivaspin 20 columns (MWCO 10 kDa, Sartorius) and then dialyzed against 200 mL TdT storage buffer (100 mM NaCl, 200 mM $K_2HPO_4$, pH 6.5) over night using Pur-A-Lyzer™ Dialysis Kit Mini 12000 tubes (Sigma).

Ni-purified sample was applied to a HiTrap Q HP anion column. Protein was eluted with linear gradient from 100% Q Buffer A (100 mM NaCl, 20 mM $K_2HPO_4$, pH 6.5) to 100% Q Buffer B (1M NaCl, 20 mM $K_2HPO_4$, pH 6.5). SDS-PAGE analysis was used to identify fractions that contained TdT, these samples were pooled and concentrated.

3. Attachment of Tethered Nucleoside Triphosphates to the Polymerase

To prepare TdT-nucleotide conjugates, a cleavable linker-nucleotide with a moiety capable of site specifically conjugating to a cysteine (i.e., maleimide) was first synthesized. Then, equal moles of TdT and linker-nucleotide were incubated overnight at 4° C. in 500 mM NaCl, 20 mM $K_2HPO_4$, pH 6.5. TdT conjugates were separated from unreacted linker-nucleotide using a S200 size exclusion column (Cytiva) pre-equilibrated in 20 mM Tris Acetate, 50 mM Potassium Acetate; pH 7.9.

Example 3. Impact of Alkylation of 6-GC Hairpin on Rate of Addition of TdT-dCTP Conjugate to the 3' End of the Hairpin In this example, we compared the rate of addition of a TdT-dCTP conjugate to the 3' end of a hairpin sequence on i) a polynucleotide where the nucleotides in the hairpin sequence are unmodified, and ii) a polynucleotide where on nucleotide of the hairpin sequence is alkylated.

Specifically, TdT conjugated to cytosine nucleotide was incubated with catalytic divalent metal (e.g., cobalt or magnesium at a concentration in the range of 20-10000 μM) and one of two '6GC hairpin' DNA oligos:

5'-FAM-TTTTTTTTTTTTTTTGCCGCGTTTCGCGGC-3' (SEQ ID NO: 24) or

5'-FAM-TTTTTTTTTTTTTTTGCCGCGTTTCGCXGC-3' (SEQ ID NO: 25) where X=O6-methyl G

Figure 5:
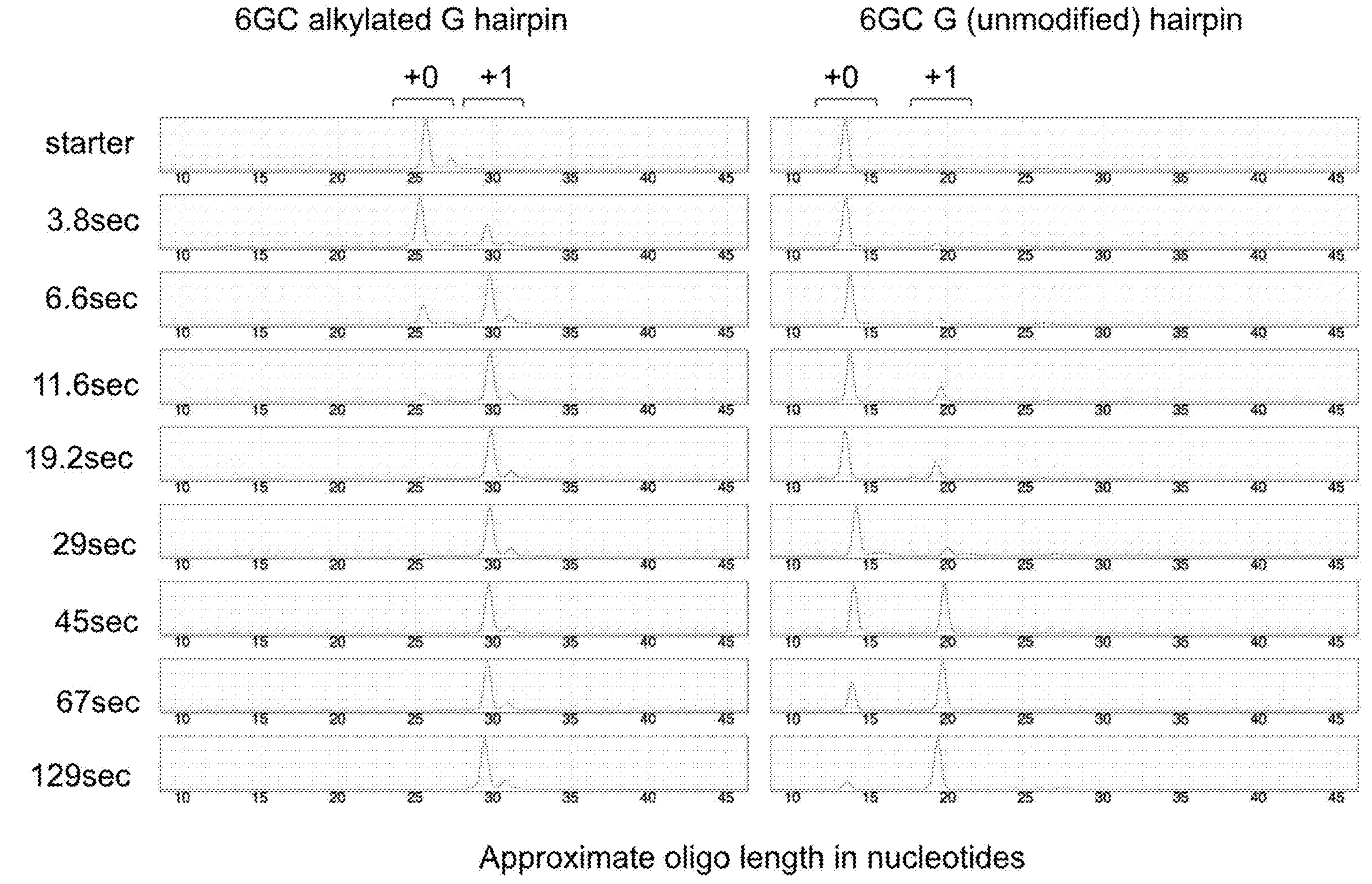
FIG. 5 shows the results of extension reactions performed starting from a nucleotide comprising a 6 GC hairpin that i) is alkylated (left column) or ii) is unmodified (right column) performed for 3.8 seconds, 6.6 seconds, 11.6 seconds, 19.2 seconds, 29 seconds, 45 seconds, 67 seconds, and 139 seconds as described in Example 3.

Both oligos were purchased from ATDBio. Each 6 GC hairpin DNA oligo and TdT-dCTP conjugate were incubated in Tris or HEPES buffer at a pH of 8 and in 50 mM salt (e.g., potassium acetate or NaCl). The reactions were stopped at 3.8 seconds, 6.6 seconds, 11.6 seconds, 19.2 seconds, 29 seconds, 45 seconds, 67 seconds, and 139 seconds by the addition of 40 mM EDTA. Unmodified oligo is labeled as 'Starter.' The resulting oligonucleotide reaction products were sized by detecting the fluorescence of the FAM oligo at 517 nm on an ABI 3730x1 DNA Analyzer (FIG. 5).

Result: As shown in FIG. 5, extension of the polynucleotide with the alkylated 6 GC hairpin proceeded faster than the polynucleotide with the unmodified 6 GC hairpin. Substantially complete turnover is achieved in less than 67 seconds with alkylation, while the reaction remains unfinished after 139 seconds with the unmodified oligo that has no basepairing prevention.

Here, the strong hairpin structure of the unmodified 6 GC hairpin (6 base pairing residues of G and C in a row without an alkyl modification) results in limited accessibility of the 3' end of the polynucleotide, thus slowing extension by a polymerase-nucleotide conjugate. In contrast, a single alkylation disrupts the hairpin structure to increase accessibility of the 3' end of the polynucleotide, leading to substantially increased extension speed. Therefore, the alkylated nucleotide in the hairpin sequence reduces the inhibition of polymerase-nucleotide conjugate addition to a polynucleotide having an adjacent hairpin sequence/secondary structure to its 3' end.

Example 4. Synthesis of 50-Mer without Alkylated Bases, with G-Alkylated Bases, and with Only Two G-Alkylated Bases Cycled polynucleotide synthesis using nucleotide-polymerase conjugates was performed to create a defined 50mer sequence:

5'-AACCGACCAAGCTACGGTTCAGAAAATTCGC-GATGCAATTCGCGATCAGC-3' (SEQ ID NO: 26). Synthesis was performed starting at the 3' end of a FAM labeled DNA oligo (starter molecule):

5'-6-FAM-CTGACAGAGATGATGAAGTCACATGA-GACATGAACTGAGTCTTTT-3' (SEQ ID NO: 27) hybridized to a DNA that was attached to a surface.

Three different 50-mer synthesis reactions were performed:

- The 'O7Et-G' sample has all Gs conjugated to TdT via the O7 position, which does not seem to prevent basepairing.
- The 'O6Bu-G' sample has all Gs conjugated to TdT via the O6 position. After linker cleavage, hydroxybutyl on the O6 position of G nucleotides are retained, which prevents basepairing.
- The 'O7Et-G & O6Bu-G' sample has all O7Et-G, except for two steps of the oligo synthesis, G32 & G44, which contain O6Bu-G bases. These two positions are predicted to have secondary structures within the sequence which can inhibit rapid nucleotide addition by TdT.

DNA extension was performed on the starting molecule by cycled addition of nucleotides via TdT-nucleotide conjugates. Each DNA extension cycle to add one nucleotide to the 3' end of the polynucleotide bound to the surface was performed as follows (at a temperature between 24-37° C.):

1. Nucleotide addition: A solution of TdT-nucleotide conjugate (corresponding to either A, T, C, or G) and divalent metal (for instance cobalt, magnesium, for instance at concentrations between 20-10000 μM) in Tris or HEPES buffer with pH 8 and 50 mM salt (for example, potassium acetate or NaCl) was added to DNA bound to a surface (e.g., a starter molecule). This results in addition of one TdT-nucleotide conjugate to the DNA.
2. Removal of TdT: After addition of the TdT-nucleotide conjugate to the DNA, the linker connecting the nucleotide and TdT in the conjugate is cleaved using a reagent such as a cleavage enzyme or a reducing agent. 40 mM EDTA is added to terminate the TdT extension reaction.
3. Regeneration of surface: A solution of NaOH pH 11 with 0.5 M NaCl was then used to wash away all unbound reaction components from the surface.

Figure 6:
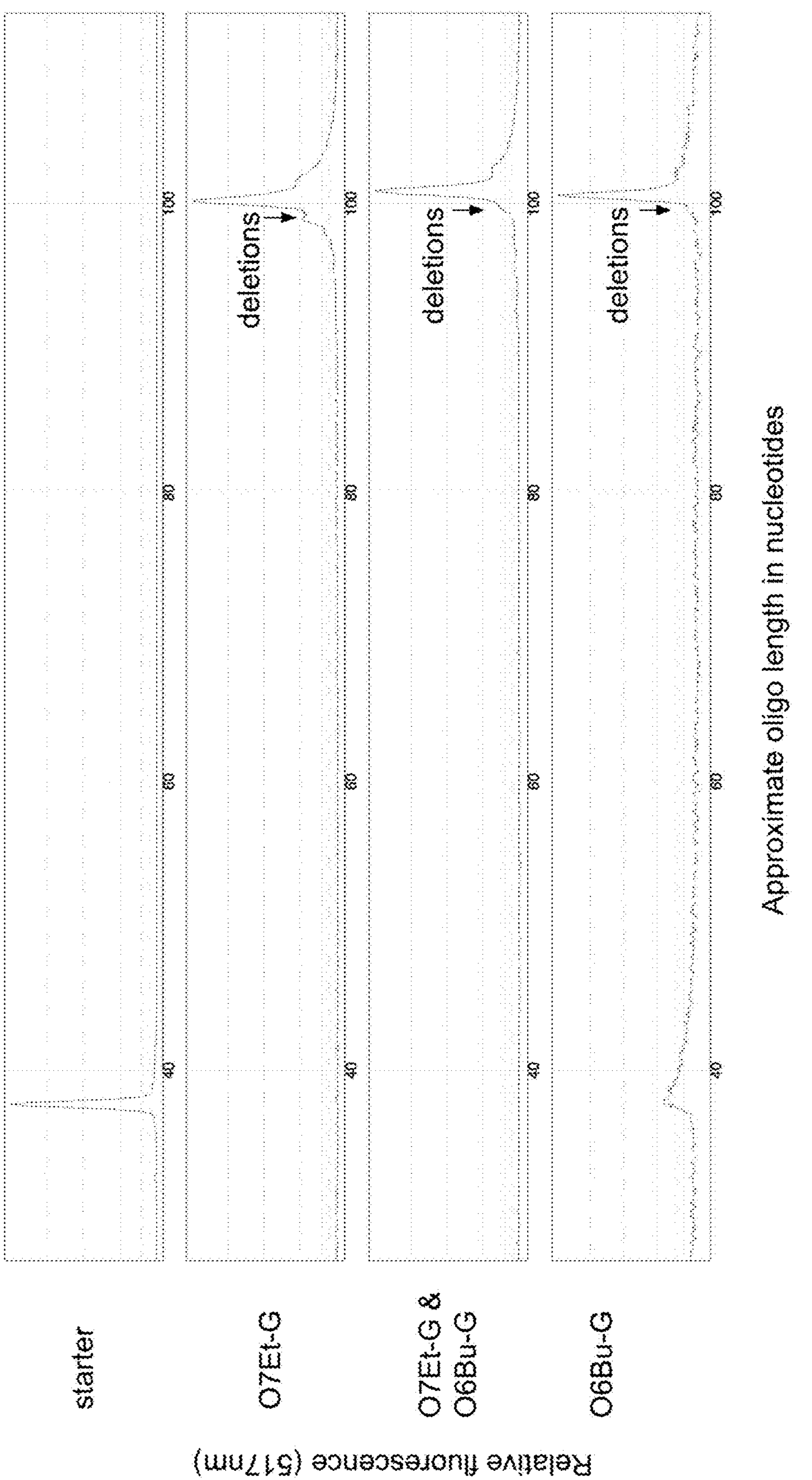
FIG. 6 shows the results of a cyclic nucleotide synthesis reaction using TdT-dNTP conjugates using i) G nucleotides without alkylations in the O6 position (O7Et-G), ii) G nucleotides with alkylation in the O6 position only in two locations with the strongest predicted secondary structure, with the rest of the G nucleotides being without alkylations (O7Et-G & O6Bu-G), and iii) G nucleotides with alkylations in the O6 position (O6Bu-G), as described in Example 4.

The resulting synthesized polynucleotides were analyzed by detecting FAM fluorescence on a SeqStudio Genetic Analyzer (ThermoFisher) DNA Analyzer (see FIG. 6).

Result: As shown in FIG. 6, the synthesis without alkylations on the O6 position (the O7Et-G sample) shows deletions (cycles where no addition occurred) on the order of ~25% of the height of the main peak. The synthesis with alkylations only in the two regions with the strongest secondary structure (the O7Et-G+O6Bu-G sample) shows a strong reduction of deletions by ~2×. The synthesis with fully alkylated G nucleotides (the O6Bu-G sample) shows no detectable deletions.

This data shows how inhibition of secondary structure formation during enzymatic DNA synthesis using alkylated nucleotides leads to substantial decreases in deletions in multi-step cycled synthesis reactions compared to synthesis with non-alkylated nucleotides.

The positions in which G-alkylations are required can be determined based on secondary structure calculations, demonstrated by the two specifically placed alkylations that resulted in a strong deletion reduction.

Example 5. Dealkylation of 50-Mer with O6-Hydroxybutyl-Deoxyguanine

A reverse primer binding site was added to the 3' end of the synthesized regions of the oligonucleotide synthesis products from Example 4 to allow testing of alkylation of the oligonucleotide via PCR amplification. Addition of a reverse primer binding site, such as addition of a homopolymer tail, is taught, e.g., in Palluk et al. 2018 Nature Biotechnology, and in PCT Publication WO2017/223517, "Nucleic Acid Synthesis and Sequencing Using Tethered Nucleoside Triphosphates," incorporated by reference in its entirety.

Following adapter addition, dealkylation of the synthesized oligonucleotides using human alkylguanine transferase ("hAGT Treatment") was performed as follows: 200 μM zinc acetate, 20 mM Tris acetate, 50 mM potassium acetate, 400 μM tris(2-carboxyethyl)phosphine, 1 μM human alkylguanine transferase, and 0.1 volumes of adapter ligated synthesis product was added to the synthesized oligonucleotide. Reactions were incubated at 37° C. for either 10 minutes, 1 hour, or 4 hours. At each ending timepoint, reactions were inactivated by incubation at 80° C. for 10 minutes. Control reactions ("No Treatment") including the above reagents without human alkylguanine transferase were also performed and terminated at each timepoint.

Each of the treated and control samples were then amplified using PCR amplification. PCR reactions used 1×Q5 Master Mix (NEB), 400 nM Forward and Reverse primer, 0.02 volumes of human alkylguanine transferase treated oligonucleotides. Thermocycling of each sample for 40 cycles under standard PCR amplification conditions was performed and the PCR reaction products were run on a 4% Nusieve 3:1 agarose gel (Lonza) at 100 volts for 2 hours and visualized with UV (see FIG. 7).

A 50-mer of the same sequence that was synthesized without any alkylations was used as a positive control to demonstrate what size amplification product is expected if the correct PCR amplification occurs.

Figure 7:
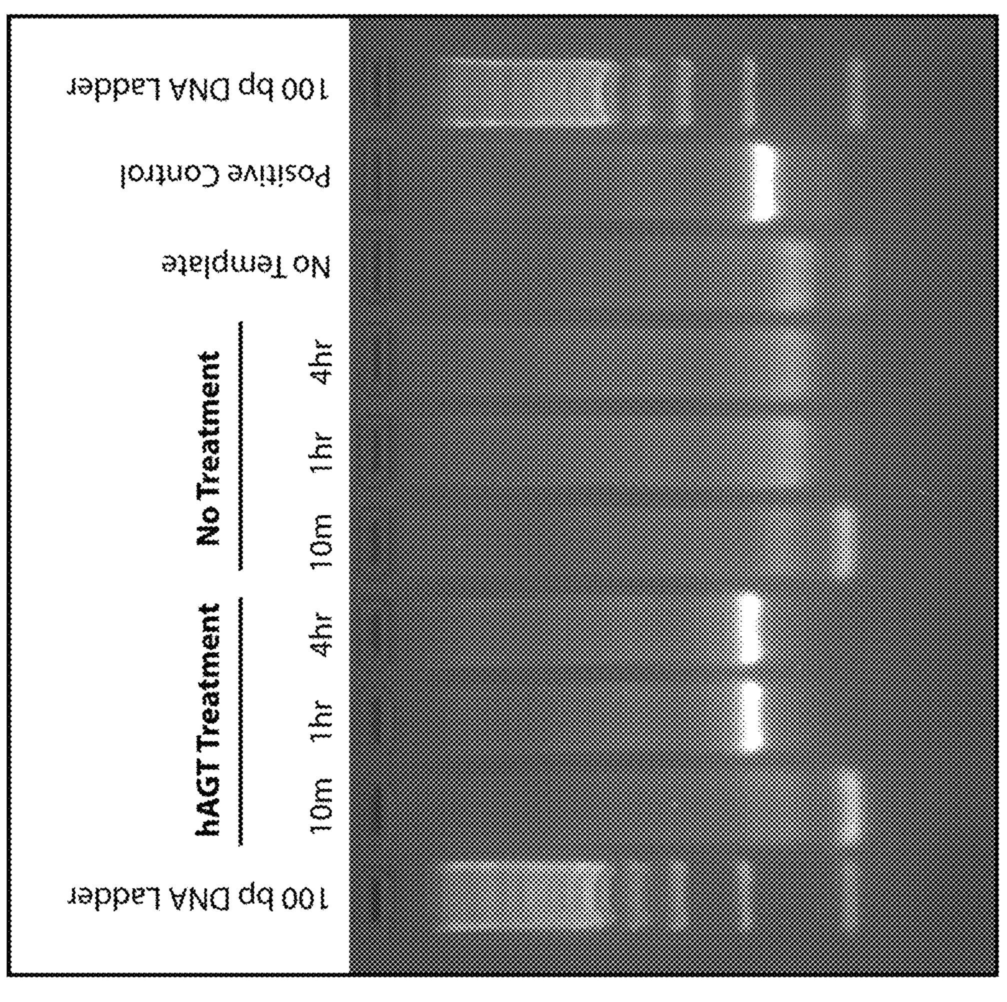
FIG. 7 shows an agarose gel visualized with UV of the product of PCR amplification of a synthesized alkylated 50-mer that was treated or not treated with AGT for the time shown, as described in Example 5. A non-alkylated positive control is also shown for reference.

Result: As shown in FIG. 7, the synthesis products with the alkylations (e.g., No Treatment) are not amplified, because the polymerase cannot read through the alkyl scars remaining on the polynucleotide. However, treatment of the alkylated 50-mer with AGT enables subsequent PCR amplification, resulting in a PCR product that has the expected size as demonstrated by the comparison with the non-alkylated positive control.

This example, combined with example 4, demonstrates the complete process of 1) synthesis of a DNA sequence with alkylations which improves synthesis by reducing deletions, 2) removal of alkylations with AGT to produce natural DNA and 3) successful amplification of the synthesized 50-mer.

Example 6. Synthesis of a Sequence that is Expected to Form G-Quadruplex is Robust with Alkylations on the O6 Position of G Nucleotides Multi-step syntheses were performed to create a 50mer poly-G sequence expected to form strong G-quadruplex structures (see Example 1)

Syntheses were performed extending a FAM labeled DNA oligo (starter molecule): 5'-6-FAM-CTGACAGAGATGATGAAGTCACATGAGACATGAACTGAGTCTTTT-3' (SEQ ID NO: 27) hybridized to a DNA that was attached to a surface. The G nucleobases were conjugated to TdT via the O6 position. After linker cleavage, hydroxybutyl on the O6 position of G bases are retained, so that the synthesized 50mer poly-G sequence retains the alkylated nucleotides. Each DNA extension cycle included:

1. Nucleotide addition: A solution of TdT-nucleotide conjugate (corresponding to either A, T, C, or G) and divalent metal (for instance cobalt, magnesium, for instance at concentrations between 20-10000 μM) in Tris or HEPES buffer with pH 8 and 50 mM salt (for example, potassium acetate or NaCl) was added to DNA bound to a surface (e.g., a starter molecule). This results in addition of one TdT-nucleotide conjugate to the DNA.
2. Removal of TdT: After addition of the TdT-nucleotide conjugate to the DNA, the linker binding the nucleotide and TdT in the conjugate is cleaved using a reagent such as a cleavage enzyme or a reducing agent. 50 mM EDTA is added to terminate the TdT extension reaction.
3. Regeneration of surface: A solution of NaOH pH 11 with 0.5 M NaCl was then used to wash away all unbound reaction components from the surface.

Figure 8:
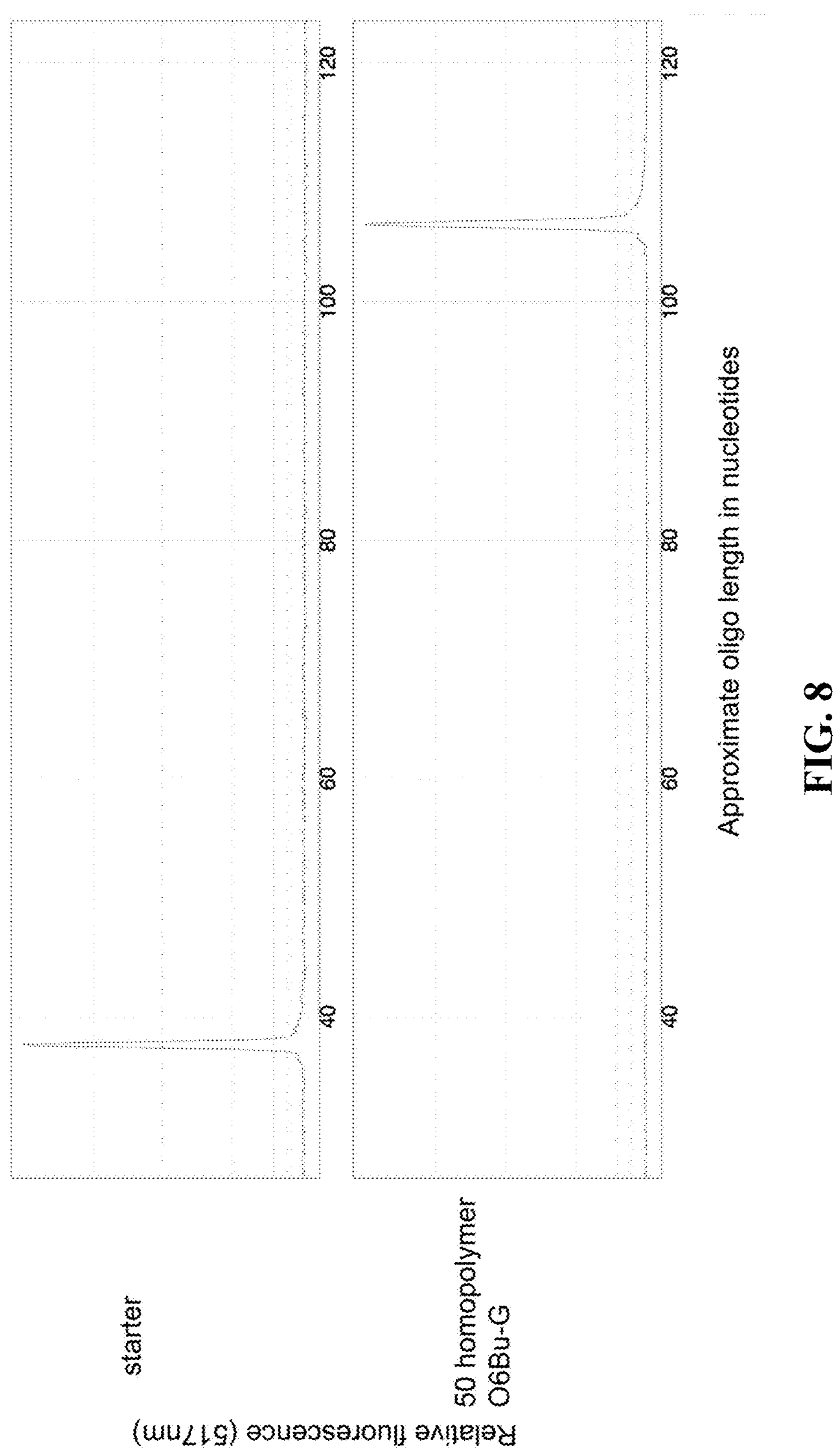
FIG. 8 shows the results of a cyclic nucleotide synthesis reaction TdT-dNTP conjugates of a 50-mer polyG homopolymer using G nucleotides with alkylations in the O6 position, as described in Example 6.

The resulting synthesized polynucleotides were analyzed based on FAM fluorescence on a SeqStudio Genetic Analyzer (ThermoFisher) DNA Analyzer (see FIG. 8).

Result: As shown in FIG. 8, synthesis of a 50mer polyG nucleotide, which was not able to be synthesized using free unmodified nucleotides as shown in Example 1, was achieved here using a TdT-nucleotide conjugate synthesis scheme using alkylated G nucleotides with very high quality.

Example 7. Synthesis of 15GC Hairpin

Figure 9:
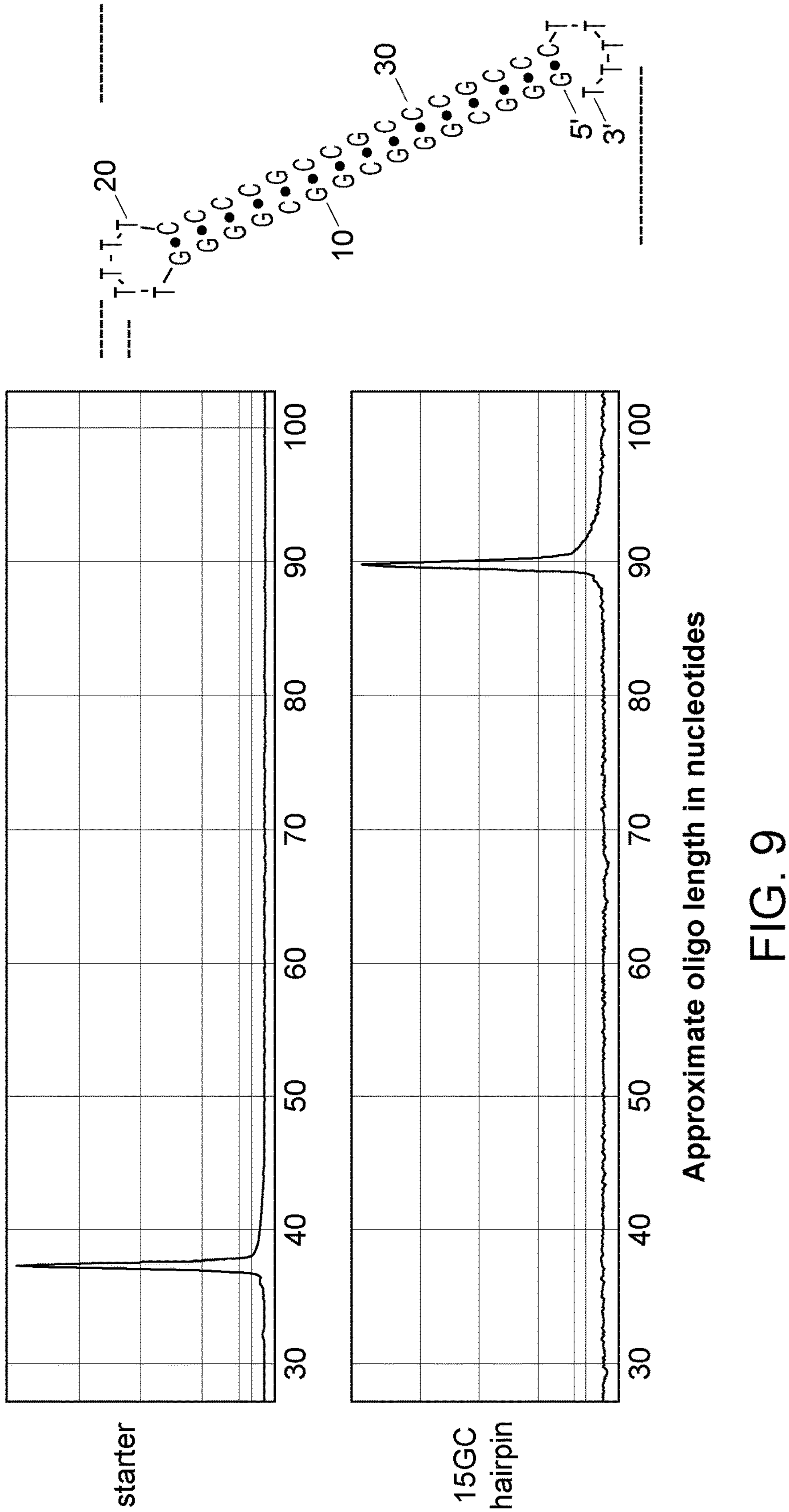
FIG. 9 shows the results of a cyclic nucleotide synthesis reaction TdT-dNTP conjugates of a 40-mer sequence with an expected 15 bp hairpin structure G nucleotides with alkylations in the O6 position, as described in Example 7. Figure discloses SEQ ID NO: 28.

Multi-step syntheses were performed to create a defined 40-mer sequence expected to form a 15 bp hairpin 5'-GGGCGGGCGGCGGGGTTTTTCCCCGCCGCCCGC CCTTTTT-3' (SEQ ID NO: 28), (see secondary structure prediction from MFold—www.unafold.org and FIG. 9). Syntheses were performed extending a FAM labeled DNA oligo (starter molecule) 5'-6-FAM-CTGACAGAGATGAT-GAAGTCACATGAGACATGAACTGAGTCTTTT-3' (SEQ ID NO: 27) hybridized to a DNA that was attached to a surface. The G bases were conjugated to TdT via the O6 position. After linker cleavage, hydroxybutyl on the O6 position of G bases are retained. Each DNA extension cycle included:

1. Nucleotide addition: A solution of TdT-nucleotide conjugate (corresponding to either A, T, C, or G) and divalent metal (for instance cobalt, magnesium, for instance at concentrations between 20-10000 μM) in Tris or HEPES buffer with pH8 and 50 mM salt (for example, potassium acetate or NaCl) was added to DNA bound to a surface (e.g., a starter molecule). This results in addition of one TdT-nucleotide conjugate to the DNA.
2. Removal of TdT: After addition of the TdT-nucleotide conjugate to the DNA, the linker binding the nucleotide and TdT in the conjugate is cleaved using a reagent such as a cleavage enzyme or a reducing agent. 50 mM EDTA is added to terminate the TdT extension reaction.
3. Regeneration of surface: A solution of NaOH pH 11 with 0.5 M NaCl was then used to wash away all unbound reaction components from the surface.

The resulting synthesized oligonucleotides were analyzed by detecting FAM fluorescence on a SeqStudio Genetic Analyzer (ThermoFisher) DNA Analyzer (see FIG. 9).

Result: As shown in FIG. 9, alkylation on the O6 position of G nucleotides enables synthesis of an oligonucleotide with a predicted 15 base-pair GC hairping with minimal deletions.

Example 8. Dealkylation of Incorporated Modified Nucleotides Using AGT

Figure 10:
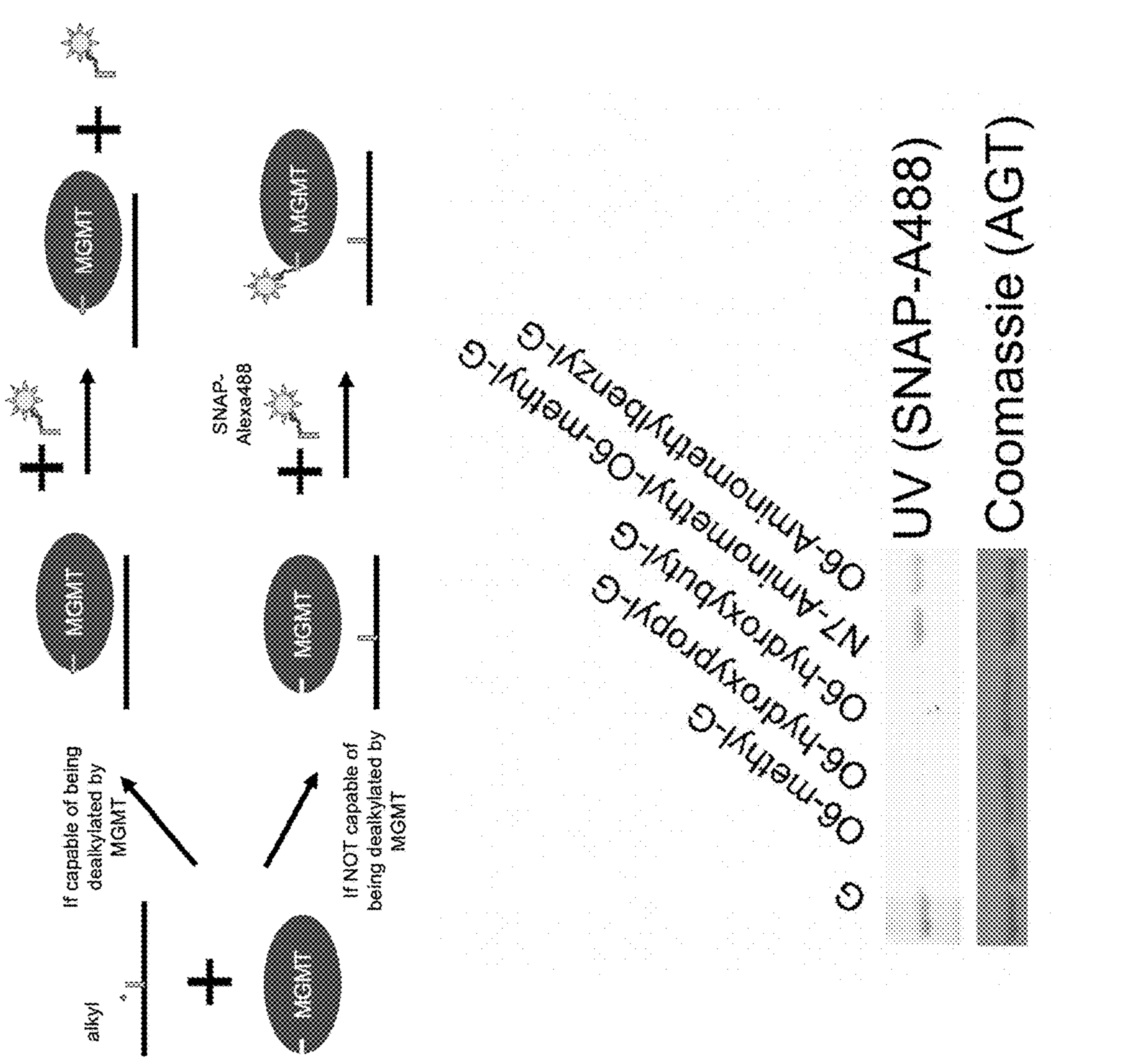
FIG. 10 shows a reaction scheme and to detect activity of human AGT on various O6-alkylated G nucleotides in a synthesized polynucleotide, and a gel showing the results of the assay for O6-methyl-G, O6-hydroxybutyl-G, O6-hydroxypropyl-G, $N_7$-aminomethyl-O6-methyl-G, and O6-aminomethylbenzyl-G as described in Example 8.

An oligonucleotide (5'-FAM-CTGACAGAGATGAT-GAAGTCACATGAGACATGAACTGAGTC-3') (SEQ ID NO: 29) (was tailed with modified G nucleotides (e.g., O6-methyl G, O6-hydroxypropyl G, O6-hydroxybutyl G, N7-aminomethyl-O6-methyl G, and O6-aminomethylbenzyl G, as shown in FIG. 10). Tailing was performed as described by NEB (https://www.neb.com/protocols/0001/01/01/a-typical-dna-tailing-reaction). 50 μM tailed oligos were dealkylated with 10 uM purified human AGT (hAGT) (Abcam), zinc acetate (400 uM), and a reducing agent (e.g., TCEP at 400 uM). To test whether these various alkylated substrates had been successfully dealkylated by hAGT, a dye-labeled, known hAGT substrate, benzyl-guanine-Alexa Fluor 488 (purchased from NEB—product #S9129S), was subsequently incubated with hAGT, which covalently attaches to any hAGT that has not already reacted with the oligo (hAGT can only react once). hAGT was separated from free dye by SDS-PAGE and dye-labeled AGT was visualized with UV light. The gel was then stained with Coomassie dye and subsequently imaged as a hAGT loading control.

The resulting gel is shown in FIG. 10. Lanes 1 & 2 are controls: G-methyl hairpin or G hairpin substrates ('G-methyl hairpin'=5'-FAM-TTTTTTTTTTTTTTTGCCGCGTTTCGCXGC-3' (SEQ ID NO: 25) where X═O6-methyl G or 'G hairpin'=5'-FAM-TTTTTTTTTTTTTTTGCCGCGTTTCGCGGC-3' (SEQ ID NO: 30)) replaced the dGTP modified oligo. The G-methyl hairpin oligo has an alkylation that can react with hAGT, while the G hairpin oligo does not.

Result: As shown in FIG. 10, for ssDNA with O6-methyl-G, O6-hydroxybutyl-G, or O6-hydroxypropyl-G, no bands were observed under UV, indicating human AGT reactivity towards these groups. In contrast, $N_7$-aminomethyl-O6-methyl-G and O6-aminomethylbenzyl-G did not react with human AGT. However, other alkyl transferases, including those described herein, may be suitable as alkylation removal enzymes for these nucleotides.

Figure 11A:
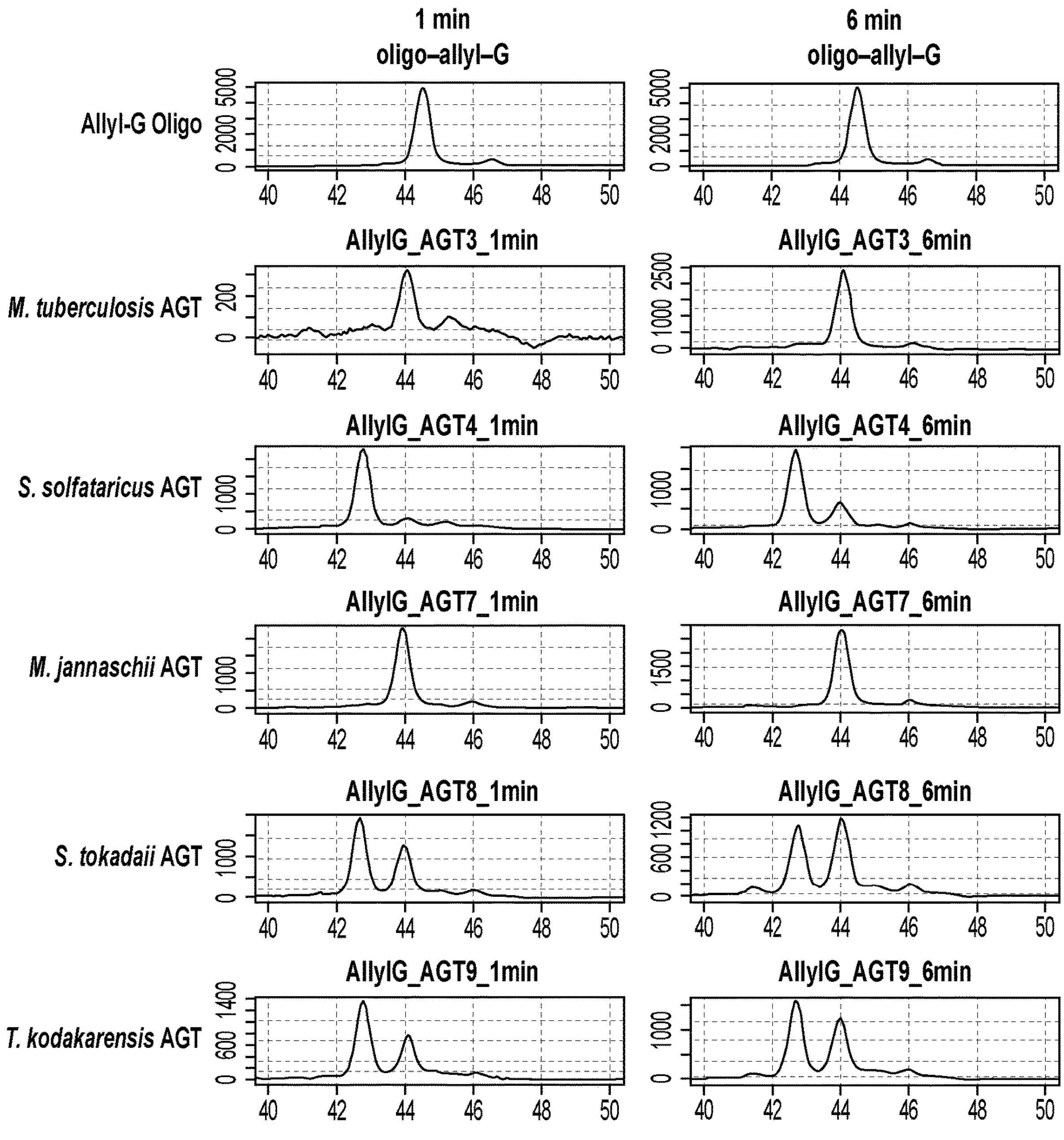
FIGS. 11A and 11B show the results of dealklylation reactions of oligonucleotide comprising 3' G nucleotide with an O6-allyl modified G nucleotide at the 3' end, with resulting oligonucleotides measured by capillary electrophoresis. "Allyl-G" represents a control, untreated oligonucleotide with the O6-allyl modified G nucleotide at the 3' end, whilte the remaining oligonucleotides were treated with the corresponding species of AGT as shown in FIGS. 11A and 11B.
Figure 11A:
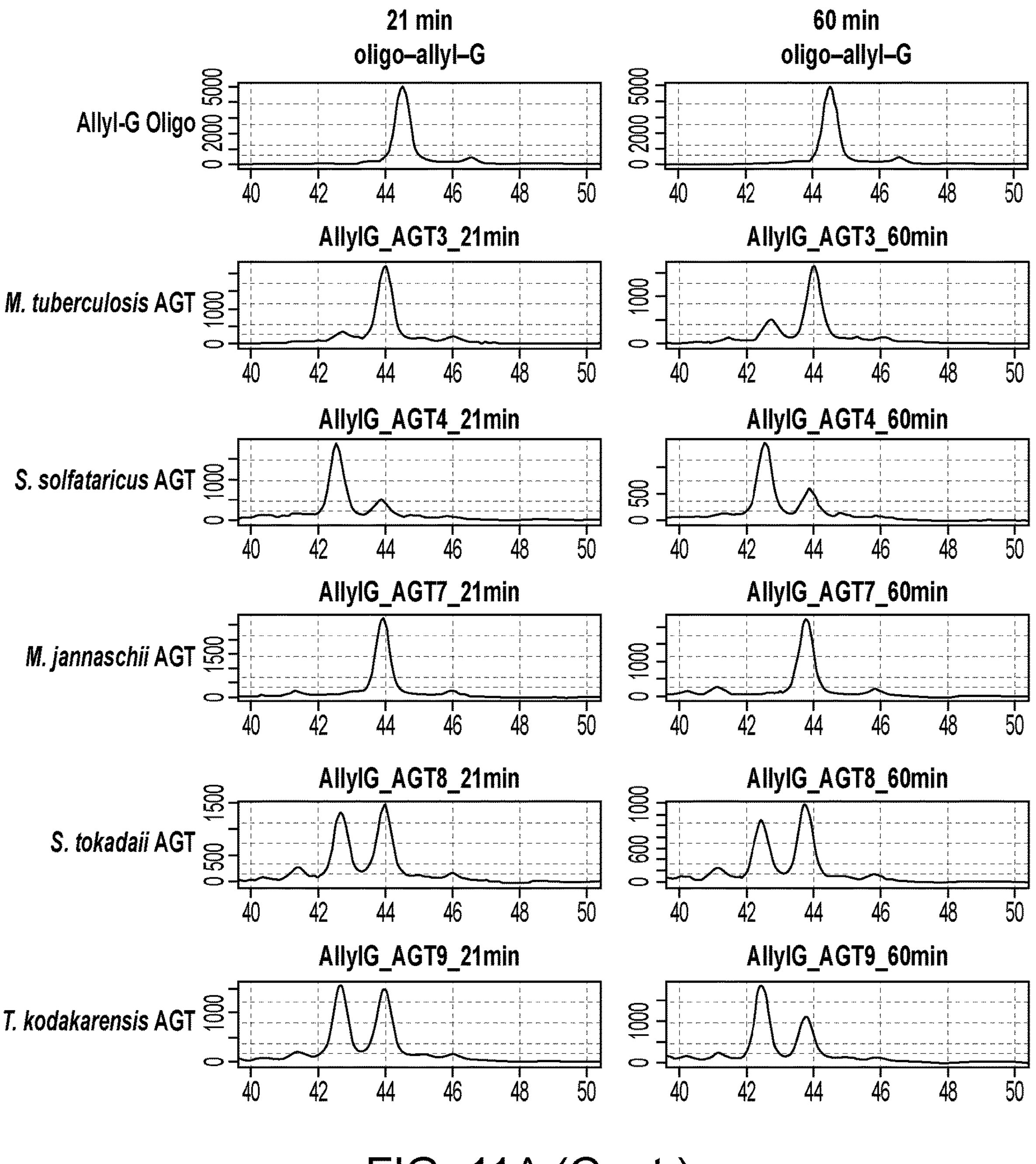
Figure 11B:
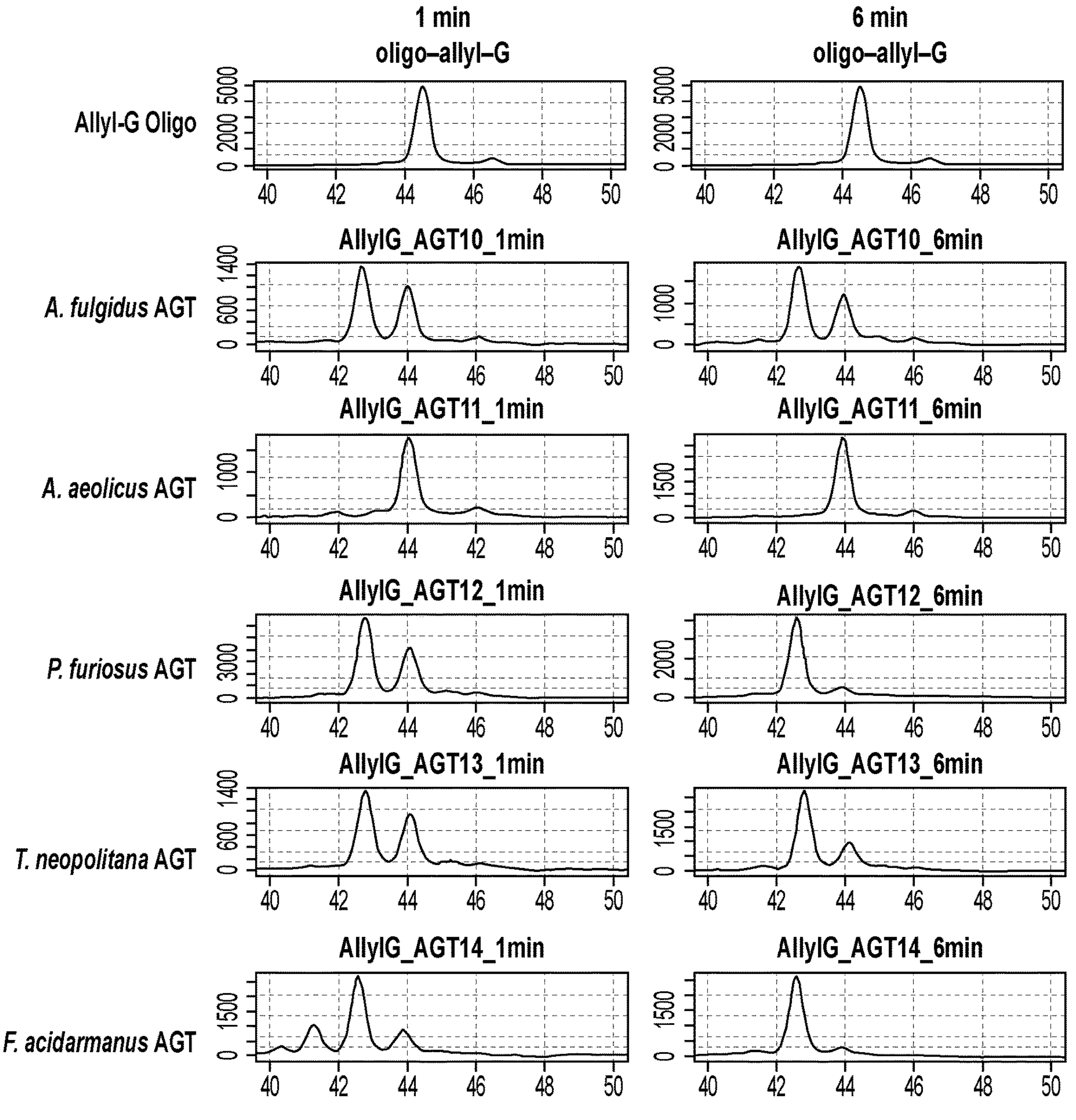
Figure 11B:
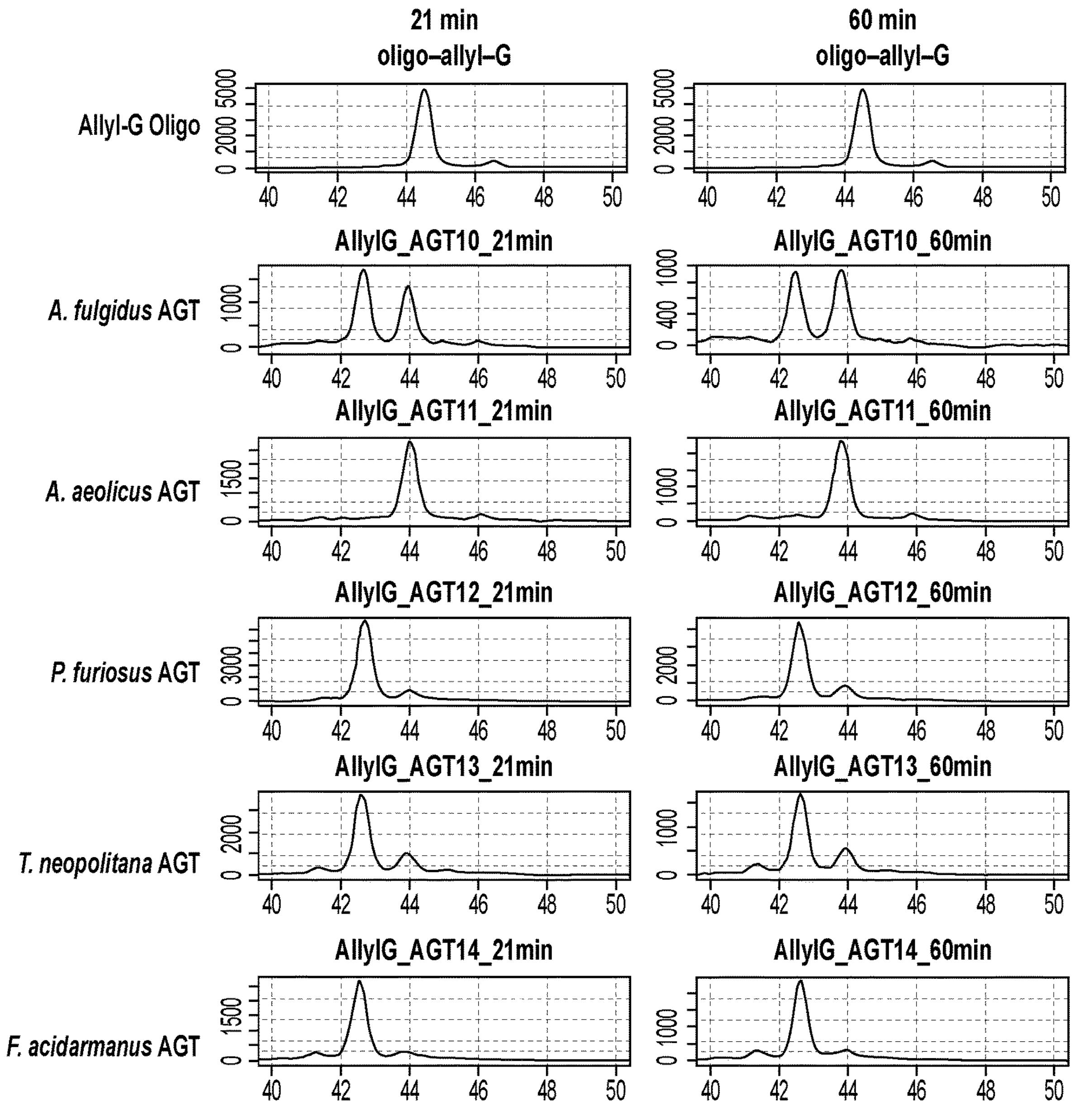

Screening for an appropriate AGT for dealkylation for an O6-allyl modified G nucleotide was performed for several different species of AGT as shown in FIG. 11A and FIG. 11B. Singly extended oligos were produced by incorporating a polymerase-nucleotide G conjugate onto the 3' end of an oligonucleotide. Polymerase was separated from the nucleotide by the addition of 0.05 mg/mL thermolabile proteinase K and an incubation at 37° C. for 25 minutes. Cleavage of the polymerase left a G nucleotide at the 3' end comprising an allyl group at the O6 position. De-alkylation was performed using 5 uM of the corresponding AGT species mixed with 20 nM extended oligonucleotide in 400 μM Zn, 1 mM DTT, and 1×TP8 buffer.

Reactions were started by adding the appropriate singly-extended oligo to the corresponding AGT mix and incubating at 37° C. Reactions were quenched after 1 minute, 6 minutes, 21 minutes, or 60 minutes by the addition of sodium dodecyl sulfate to 0.5%. Oligonucleotides were analyzed for dealkylation of scarred-nucleotide through capillary electrophoresis.

RESULT: FIGS. 11A and 11B demonstrates the results of the dealkyation reactions. The x-axis represents the approximate oligo length in nucleotides. Scarred singly-extended oligos run to the right of singly-extended oligos with natural nucleotides because of the scars. Allyl-G Oligo in FIGS. 11A and 11B shows an untreated oligonucleotide with an O6-allyl modified G nucleotide at the 3' end (without AGT dealkylation). Successful dealkylation reactions with AGT result in a shift to the left of the species that have been dealkylated, approximately where singly-extended oligos with natural nucleotides run, representing the removal of the scars. As shown in FIGS. 11A and 11B, several species of AGT were identified that are capable of removing the alkyl group from the incorporated nucleotide. Using this screen, we can identify suitable AGT for removing alkyl groups from alkyl modified nucleotides incorporated into an oligonucleotide during synthesis.

The scheme described enables rapid screening for alkylation removal enzymes for specific base modifications suitable with removal of alkyl groups on synthesized polynucleotides. AGT-like enzymes are ubiquitous in all classes of organisms. Testing so that one of ordinary skill in the art can identify those that work on implementations of this DNA synthesis strategy is therefore taught herein.

Example 9. Polyoligonucleotide Synthesis with Natural and Modified Nucleotides In this example, we tested extension reactions performed by TDT with natural nucleotides (dGTP and dATP) and modified nucleotides (06Me dG, O6Allyl dG, and O6Bu dG).

Extension reactions were performed with the following reagents: a 50 nM polyT DNA oligo sequence containing 35T (SEQ ID NO: 32) or a polyC DNA oligo sequence containing 30 C (SEQ ID NO: 33). Each oligo was labeled with a 5' fluorescein and purchased from IDT, 1×TP8 Buffer, metal mix containing 1 mM $MgCl_2$ and 0.25 mM $CoCl_2$ (New England Biolabs), 1 units/μL of terminal transferase (New England Biolabs), 250 uM of "dG" (deoxyguanosine triphosphate), "dA" (deoxyadenosine triphosphate) or modified nucleotide triphosphates.

Reactions were incubated at 37 degrees Celsius at various timepoints (30 seconds, 1 minute, 4 minutes, or 8 minutes) until the reactions were stopped by the addition of 40 mM ethylenediaminetetraacetic acid. Oligonucleotides were analyzed by capillary electrophoresis.

Figure 12A:
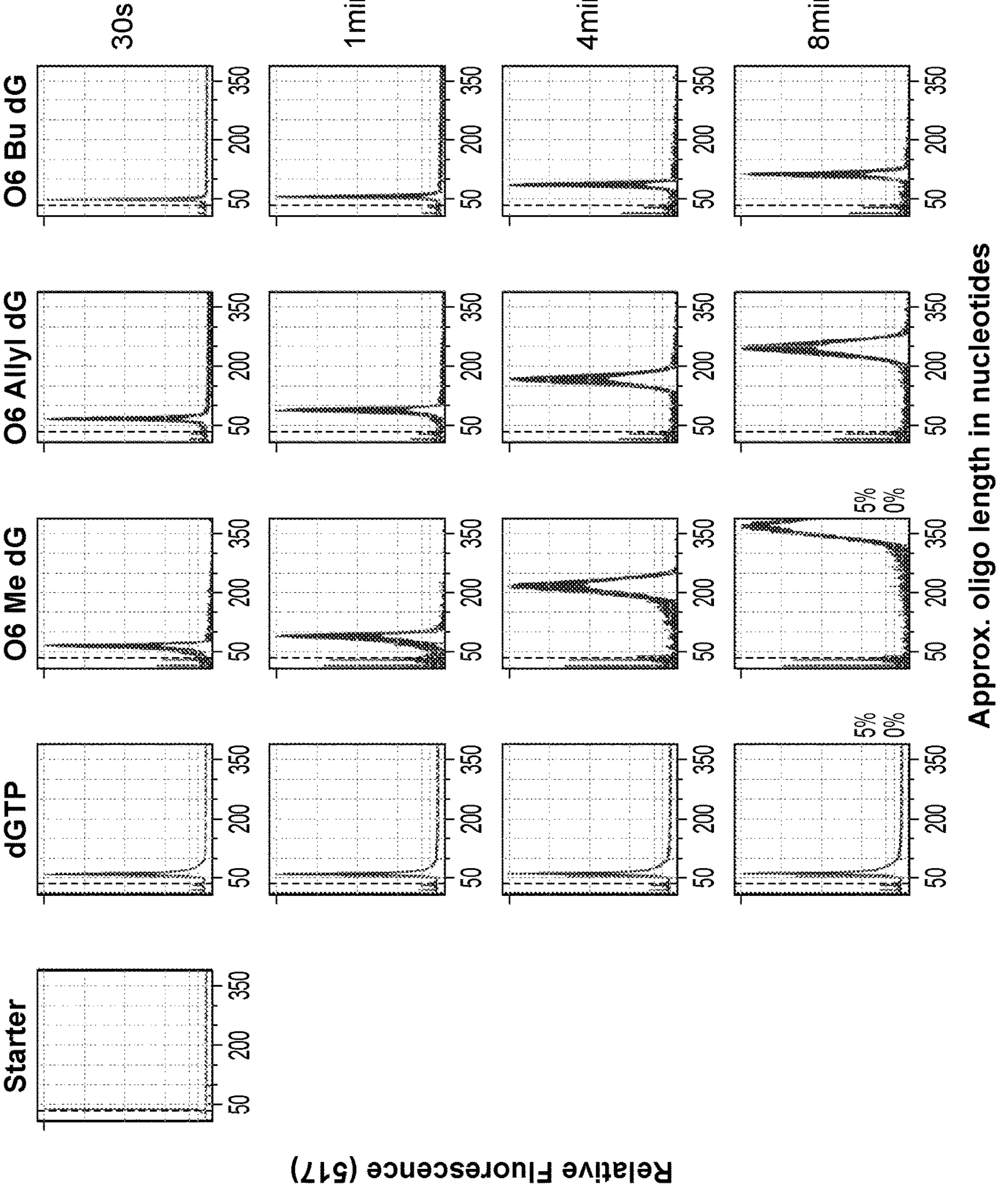
FIGS. 12A and 12B show the result of polyG synthesis reactions performed without ("dGTP) and with an O6 alkyl modification at the 3' end of a polyT starter oligo (FIG. 12A) and at the 3' end of a polyC starter oligo (FIG. 12B).
Figure 12B:
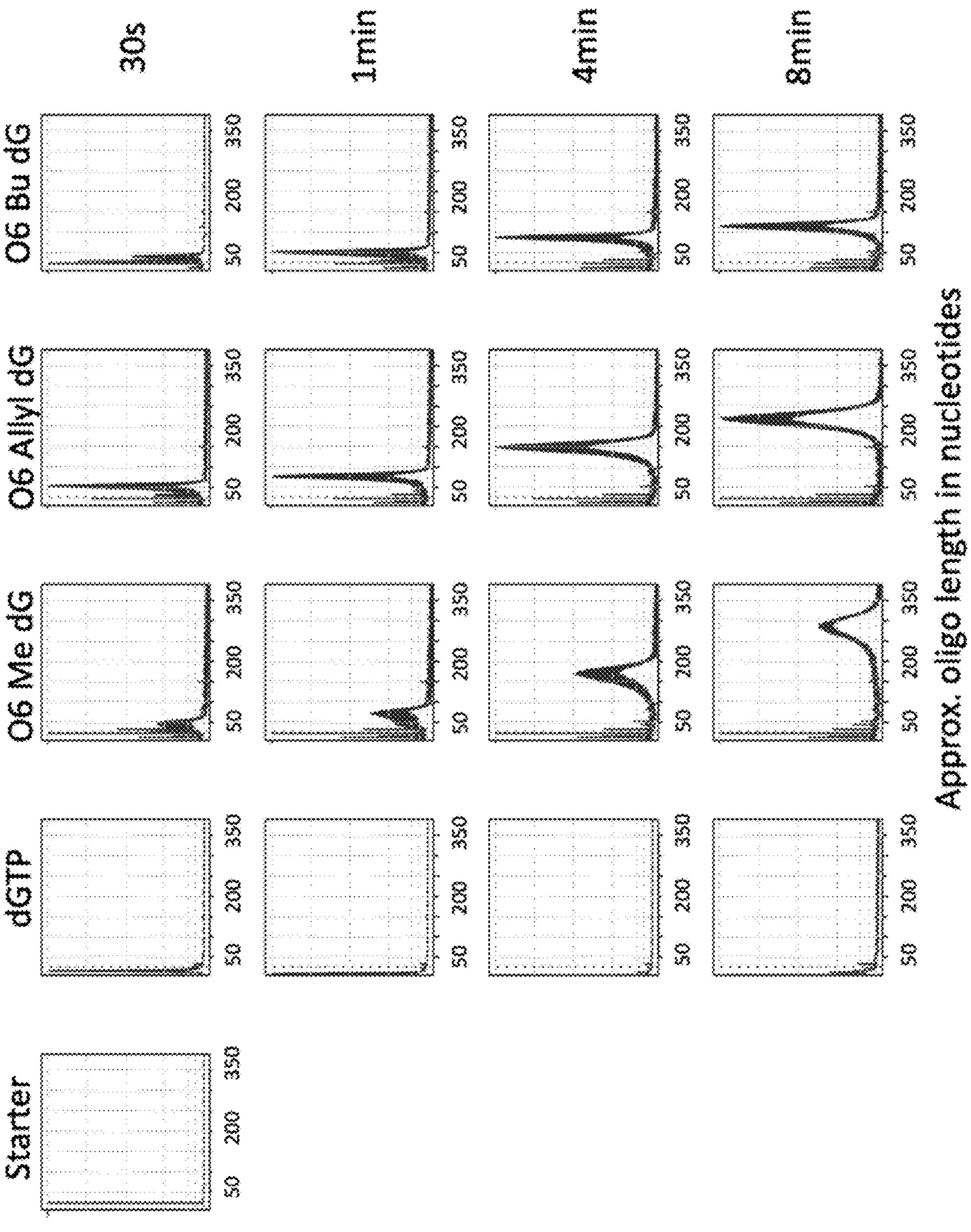

Result: FIGS. 12A and 12B show extension reactions performed for 30 seconds, 1 minute, 4 minutes, or 8 minutes. The x-axis is the approximate oligo length in nucleotides and the y-axis is relative fluorescence of fluorescein at 517 nm. The red-dashed line in each plot represents the position of the starter. FIG. 12A shows data using the polyT starter with dG (left column), 06Me dG, O6Allyl dG, and O6Bu dG. Extension reaction with TdT and dGTP produces short products where extension stalls (as G-quadruplexes form). In contrast, extension with dGTP containing modified nucleotides shows robust and continuous extension without stalling.

FIG. 12B shows an experiment using the oligonucleotide starter containing a sequence of all C's, TdT and various nucleotides, dG (left column), 06Me dG, O6Allyl dG, and O6Bu dG. The extension reaction with dGTP is quite slow and base-pairing with the C template prevents extension of the starter. However, nucleotide extension containing O6-position modifications has continuous nucleotide turnover. Thus, as shown in all the above experiments, the use of nucleotides containing modifications at the O6 position in dG improves polynucleotide synthesis and inhibits secondary structure formation.

Example 10. Dealkylation of Oligos with Terminal, Single-Extension Scarred Nucleotide In these experiments, we have tested if we are able to remove the scars from our scarred nucleotides.

Terminal, singly-extended oligos were produced by using the following reagents: 300 nM starter oligo (5'-6-FAM-CTGACAGAGATGATGAAGTCACATGAGACAT-GAACTGAGTCTTTT-3' (SEQ ID NO: 27)), 70 mM tris potassium buffer pH 8, 100 μM cobalt-acetate, 6 μM bacterial phosphatase, and 1.5 uM of corresponding conjugate (polymerase-nucleotide conjugate cleavable by proK—after proK cleavage leaves 'scarred nucleotide' of allyl-06 dGTP, butyl(Bu)-O6-dGTP, allyl-O4 dUTP, or propargyl(Prg)-O4 dUTP).

Reactions were started by adding the appropriate conjugate to the oligo mix and incubating at room temperature for 5 minutes. Reactions were quenched by the addition of 0.5 mM DM-nitrophen. Polymerase was separated from the nucleotide by the addition of 0.05 mg/mL thermolabile proteinase K and an incubation at 37° C. for 25 minutes. Thermolabile proteinase K was heat-denatured with a 10-minute incubation at 65° C. DM-nitrophen was broken down with a 3-minute UV light treatment. Oligonucleotides were analyzed for +1 addition of nucleotide through capillary electrophoresis.

Figure 13:
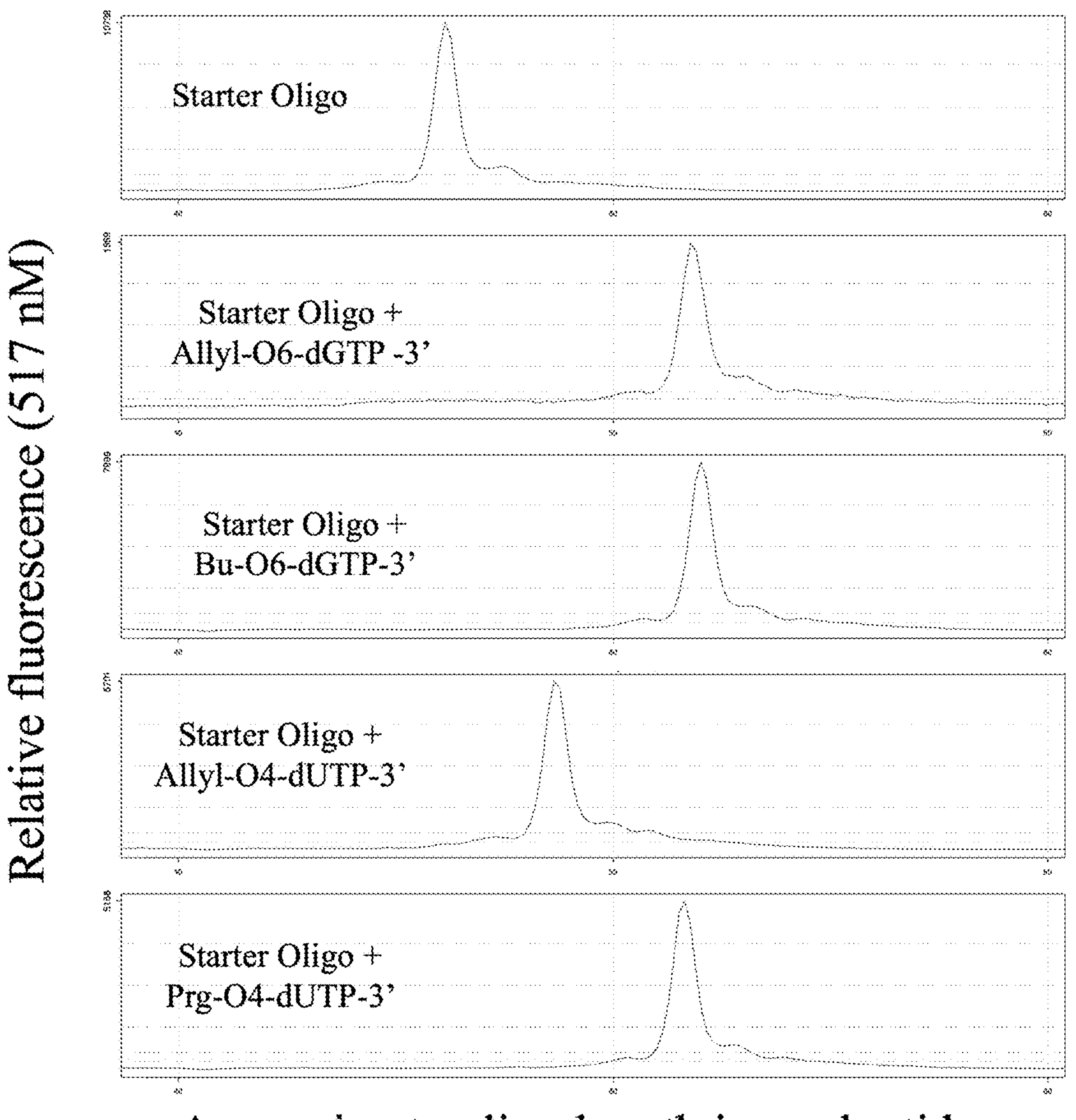
FIG. 13 shows the results of incorporation of alkylated G and U nucleotides at the 3' end of an oligonucleotide by a polymerase-nucleotide conjugate, followed by cleavage of the polymerase, leaving an alkyl scar on the G or U nucleotides.
Figures 14A, 14B:
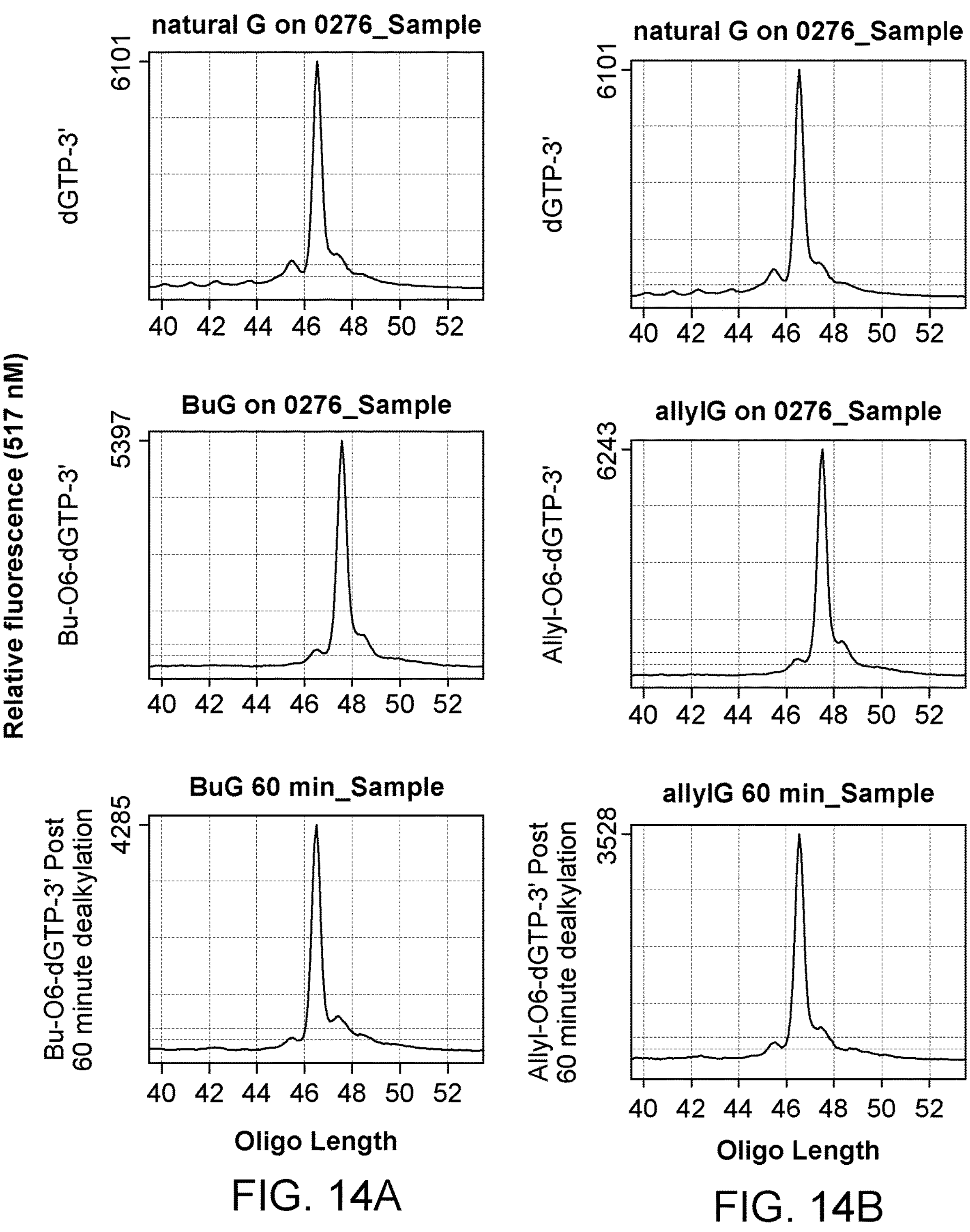
FIG. 14A-D shows the successful dealkylation of the synthesized oligonucleotides from FIG. 13 by AGT, resulting in scarless conjugate-based oligonucleotide synthesis.
Figures 14C, 14D:
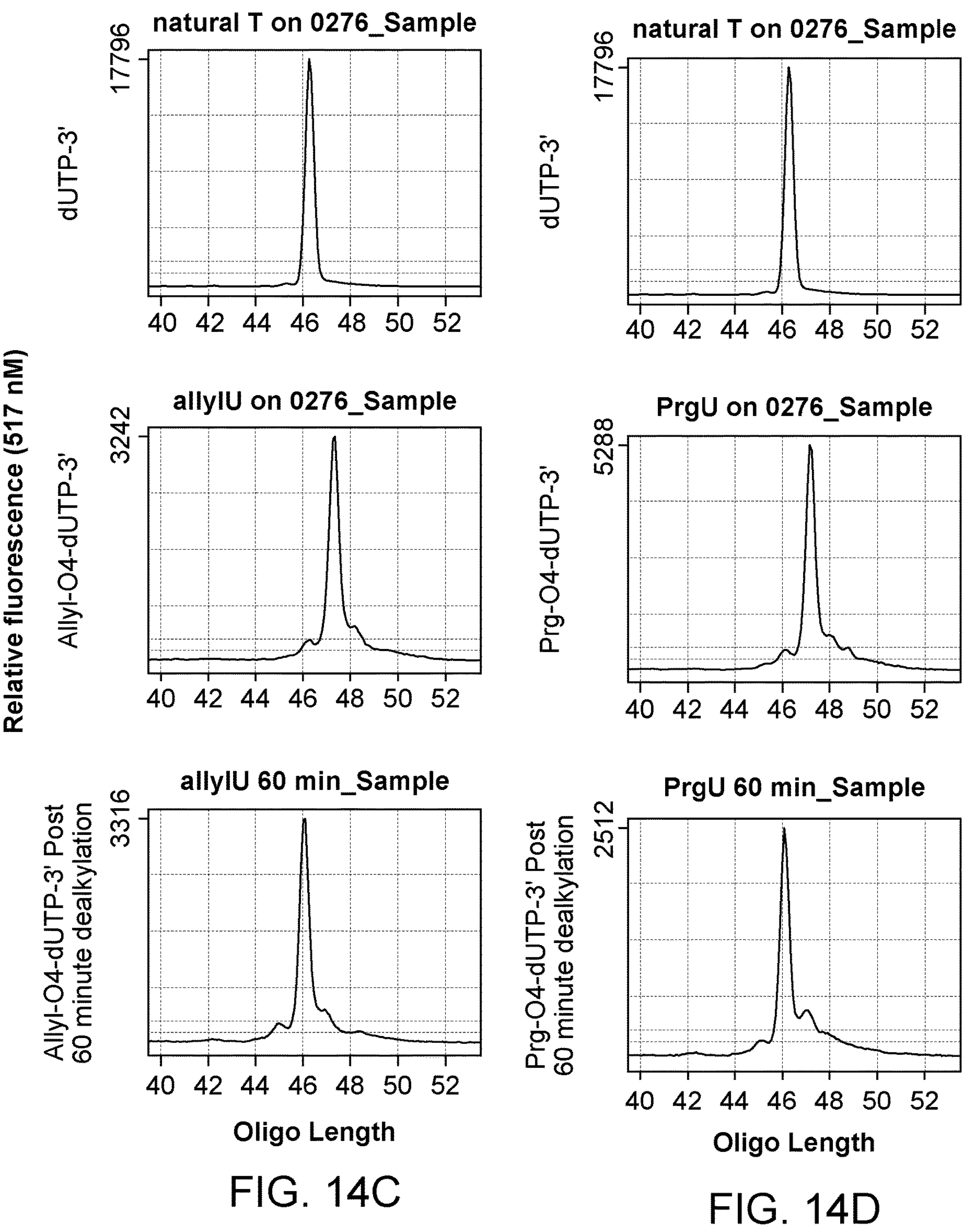

RESULT: FIG. 13 demonstrates the results of the extension reactions as measured by capillary electrophoresis. The x-axis represents the approximate oligo length in nucleotides and the y-axis represents the fluorescence of fluorescein at 517 nm. Starter is unmodified starter oligo as described above. Extension reaction with each of the conjugates leads to a shift to the right compared to the starter oligo, indicating the addition of a scarred nucleotide. Thus, TdT conjugated to the nucleotides successfully was added to the starter oligonucleotide at the 3' end, generating singly-extended substrates. These were then used for the following dealkylation experiments.

Dealkylation of singly-extended oligos was performed by using the following reagents: 40 μM 06 methylguanine dna methyltransferase from *Ferroplasma acidarmanus* (Fa MGMT), 10 mM dithiothreitol, 70 mM tris potassium buffer pH 9, 5 mM ethylenediaminetetraacetic acid, and 35 nM of singly-extended oligo having the following modified nucleotides at the 3' end: Allyl-O6-dGTP-3'; Bu-O6-dGTP-3'; Allyl-O4-dUTP-3'; or Prg-O4-dUTP-3'. Natural controls were purchased from IDT having unmodified dGTP and dUTP at the 3' end of the same oligo sequence as the modified nucleotides.

Reactions were started by adding the appropriate singly-extended oligo to the Fa MGMT mix and incubating at 37° C. Reactions were quenched after 60 minutes by the addition of sodium dodecyl sulfate to 0.5%. Oligonucleotides were analyzed for dealkylation of scarred-nucleotide through capillary electrophoresis.

RESULT: FIG. 14A-14D demonstrate the results of the 60 minute dealkyation reactions. The x-axis represents the approximate oligo length in nucleotides and the y-axis represents the fluorescence of fluorescein at 517 nm. Scarred singly-extended oligos run to the right of singly-extended oligos with natural nucleotides because of the scars. Dealkylation reactions with Fa MGMT result in a shift to the left of the species that have been dealkylated, approximately where singly-extended oligos with natural nucleotides run, representing the removal of the scars. This is observed in FIG. 14A for Bu-O6-dGTP-3', FIG. 14B for Allyl-O6-dGTP-3', in FIG. 14C for Allyl-O4-dUTP-3', and FIG. 14 D for Prg-O4-dUTP-3'. Thus, we are able to dealkylate our scarred nucleotides to natural nucleotides after oligonucleotide synthesis with Fa MGMT treatment.

Other Embodiments

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

The invention claimed is:

1. A method of synthesizing a polynucleotide, comprising:

providing a polynucleotide comprising one or more alkylated nucleobases;

enzymatically removing one or more alkyl groups from said one or more alkylated nucleobases.

2. The method of claim 1, wherein providing said polynucleotide comprises:

contacting a precursor polynucleotide with a polymerase and a nucleotide comprising said alkylated nucleobase;

adding said nucleotide to the 3' end of said precursor polynucleotide via said polymerase.

3. The method of claim 1, wherein providing said polynucleotide comprises:

contacting a precursor polynucleotide with a conjugate comprising a nucleotide covalently linked to a polymerase via a linker, wherein said nucleotide comprises said alkylated nucleobase; and adding said nucleotide to the 3' end of said precursor polynucleotide via said polymerase.

4. The method of claim 3, further comprising cleaving said linker after addition of said nucleotide to said precursor polynucleotide.

5. The method of claim 2, wherein said polymerase is a template independent polymerase.

6. The method of claim 2, wherein the nucleotide comprises a 2' or 3' modification.

7. The method of claim 1, wherein said removal of said one or more alkyl groups comprises contacting said polynucleotide with an enzyme capable of removing said one or more alkyl groups from said alkylated nucleobases.

8. The method of claim 7, wherein said enzyme is an alkyl transferase.

9. The method of claim 3, wherein the conjugate is represented by:

III

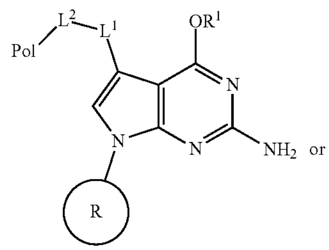

or

IV

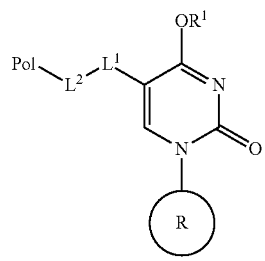

wherein $L^1$ is selected from the group consisting of an optionally substituted $C_{1-4}$ alkylene chain, wherein 1-2 methylene units is optionally and independently replaced with —O—, —N($R^a$)—, —C(O)—, —S—, —S(O)—, —$S(O)_2$—, or phenylene;

$L^2$ is a cleavable linker;

each $R^a$ is independently hydrogen or $C_{1-6}$ alkyl;

$R^1$ is $C_{1-6}$ alkyl, $C_{2-6}$ alkenyl, $C_{1-6}$ alkynyl, and —$(CH_2)_{0-3}$Ph, wherein $R^1$ is optionally substituted with 1-6 instances of $R^{1a}$;

each $R^{1a}$ is independently selected from halogen, $C_{1-6}$ alkyl, —$(CH_2)_{0-3}OR^{1b}$, —$NO_2$, —$N_3$, —$OPO_2OH$, and —$(CH_2)_{0-3}NHR^{1b}$; and each $R^{1b}$ is independently selected from hydrogen, $C_{1-6}$ alkyl, —C(O)($C_{1-6}$ alkyl), $C_{1-6}$ haloalkyl, —C(O)($C_{1-6}$ haloalkyl), and —$CH_2OAc$;

R is a ribose polyphosphate or deoxyribose polyphosphate; and

Pol is a polymerase.

10. The method of claim 9, wherein $R^1$ is $C_{1-3}$ alkyl.

11. The method of claim 10, wherein $R^1$ is methyl.

12. The method of claim 9, wherein the conjugate is

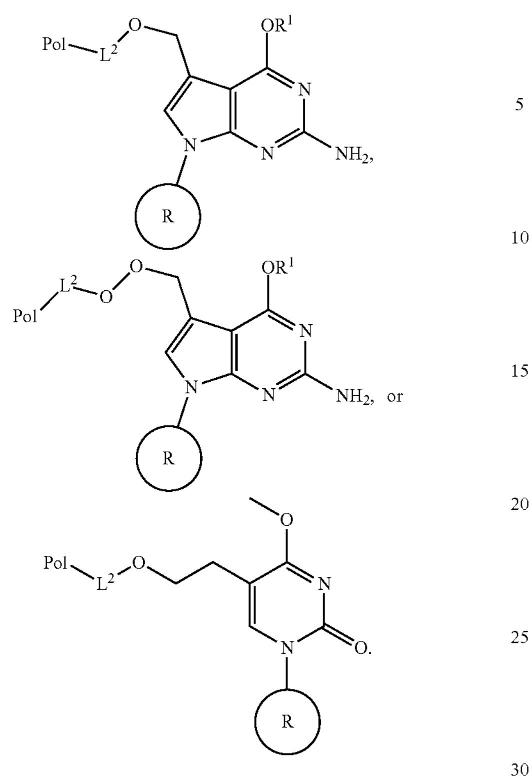
or
* * * * *

SEQUENCE LISTING

```
Sequence total quantity: 33
SEQ ID NO: 1             moltype = AA  length = 207
FEATURE                  Location/Qualifiers
source                   1..207
                         mol_type = protein
                         organism = Homo sapiens
SEQUENCE: 1
MDKDCEMKRT TLDSPLGKLE LSGCEQGLHE IKLLGKGTSA ADAVEVPAPA AVLGGPEPLM  60
QCTAWLNAYF HQPEAIEEFP VPALHHPVFQ QESFTRQVLW KLLKVVKFGE VISYQQLAAL  120
AGNPKAARAV GGAMRGNPVP ILIPCHRVVC SSGAVGNYSG GLAVKEWLLA HEGHRLGKPG  180
LGGSSGLAGA WLKGAGATSG SPPAGRN                                     207

SEQ ID NO: 2             moltype = AA  length = 171
FEATURE                  Location/Qualifiers
source                   1..171
                         mol_type = protein
                         organism = Escherichia coli
SEQUENCE: 2
MLRLLEEKIA TPLGPLWVIC DEQFRLRAVE WEEYSERMVQ LLDIHYRKEG YERISATNPG  60
GLSDKLREYF AGNLSIIDTL PTATGGTPFQ REVWKTLRTI PCGQVMHYGQ LAEQLGRPGA  120
ARAVGAANGS NPISIVVPCH RVIGRNGTMT GYAGGVQRKE WLLRHEGYLL L          171

SEQ ID NO: 3             moltype = AA  length = 354
FEATURE                  Location/Qualifiers
source                   1..354
                         mol_type = protein
                         organism = Escherichia coli
SEQUENCE: 3
MKKATCLTDD QRWQSVLARD PNADGEFVFA VRTTGIFCRP SCRARHALRE NVSFYANASE  60
ALAAGFRPCK RCQPEKANAQ QHRLDKITHA CRLLEQETPV TLEALADQVA MSPFHLHRLF  120
KATTGMTPKA WQQAWRARRL RESLAKGESV TTSILNAGFP DSSSYYRKAD ETLGMTAKQF  180
RHGGENLAVR YALADCELGR CLVAESERGI CAILLGDDDA TLISELQQMF PAADNAPADL  240
MFQQHVREVI ASLNQRDTPL TLPLDIRGTA FQQQVWQALR TIPCGETVSY QQLANAIGKP  300
KAVRAVASAC AANKLAIIIP CHRVVRGDGT LSGYRWGVSR KAQLLRREAE NEER        354

SEQ ID NO: 4             moltype = AA  length = 147
FEATURE                  Location/Qualifiers
source                   1..147
                         mol_type = protein
                         organism = Archaeoglobus fulgidus
SEQUENCE: 4
MFSVKWGELY FNVVMEGGKA VKSYFSTYPS FSSSDSEYAR QLERYFSGER VEVRIPYRLK  60
ASSFTRRVLE EVSRIPYGMV RMYSDIAKAL NTSPRAVGQA VKRNPLPVII PCHRVVGKKE  120
IGGYTVSCSD IDGKSLKKRL LRLEGVF                                     147

SEQ ID NO: 5             moltype = AA  length = 201
FEATURE                  Location/Qualifiers
source                   1..201
                         mol_type = protein
                         organism = Aquifex sp.
SEQUENCE: 5
MSTERRREVI SGTSAQIALI ILRKITIRGA ELQDLPEERY VKSVYSLKSQ TKKTVIPITV  60
LKTALTPSLS LEIFFDKGKI SKISILKKKE QKIIPEFLLY FLKEGDPLIN LEYLDLKRIN  120
PKCIKVYLKL KEVASFGKII TYGELARLTD LHPRFVGYCM KINPFPVIIP CHRVISKRDL  180
GGFNQGIEIK SELLKHEGLI L                                           201

SEQ ID NO: 6             moltype = AA  length = 173
FEATURE                  Location/Qualifiers
source                   1..173
                         mol_type = protein
                         organism = Ferroplasma sp.
SEQUENCE: 6
MKNNNIKIQY YKTKIGELIL GSFEGNLCIL DFRYSKKRTT IDNRIKTGLK ANFLEEEDEI  60
LAETKKQVAE YLDGNRKEFD IPLLMVGTDF QKNVWNALLK IPYGTTITYL QLAKNIGNAK  120
AVRAVANADG ANAMAVIIPC HRVIESNGGL GGYGGGVAIK KQLLELEKGN PEQ        173

SEQ ID NO: 7             moltype = AA  length = 167
FEATURE                  Location/Qualifiers
source                   1..167
                         mol_type = protein
```

```
                          organism = Methanocaldococcus jannaschii
SEQUENCE: 7
MIIQIEEYFI GMIFKGNQLV RNTIPLRREE IFNFMDGEVV SNPEDEHLKV AEIILKLYFA  60
EIDDKKVREL ISYKLEVPEF TKKVLDIVKD IEFGKTLTYG DIAKKLNTSP RAVGMALKRN  120
PLPLIIPCHR VVAKNSLGGY SYGLDKKKFI LERERLNMVS FKFNKVY                167

SEQ ID NO: 8              moltype = AA  length = 165
FEATURE                   Location/Qualifiers
source                    1..165
                          mol_type = protein
                          organism = Mycobacterium tuberculosis
SEQUENCE: 8
MIHYRTIDSP IGPLTLAGHG SVLTNLRMLE QTYEPSRTHW TPDPGAFSGA VDQLNAYFAG  60
ELTEFDVELD LRGTDFQQRV WKALLTIPYG ETRSYGEIAD QIGAPGAARA VGLANGHNPI  120
AIIVPCHRVI GASGKLTGYG GGINRKRALL ELEKSRAPAD LTLFD                  165

SEQ ID NO: 9              moltype = AA  length = 174
FEATURE                   Location/Qualifiers
source                    1..174
                          mol_type = protein
                          organism = Pyrococcus furiosus
SEQUENCE: 9
MILEVRKFQV KNKAVYIGTL SEDKIFGIIF SIDEPEVIRH RIPTLINFLE KRLNKKLEIK  60
EGNSGFSDVV FKTLIGKISN EEAAEFIEVS YLTKFERKLY IYLVENVKRG EVITYGELAK  120
ILNTSSRAVG AAVKRNPYPI IVPCHRVIGR KNPYLYTPKP EYKKFLLEVE GWTS        174

SEQ ID NO: 10             moltype = AA  length = 151
FEATURE                   Location/Qualifiers
source                    1..151
                          mol_type = protein
                          organism = Sulfolobus solfataricus
SEQUENCE: 10
MLVYGLYKSP LGYITVAKDD KGFIMLDFCD CVEGNSRDDS SFTEFFHKLD LYFEGKPINL  60
REPINLKTYP FRLSVFKEVM KIPWGKVMTY KQIADSLGTS PRAVGMALSK NPILLIIPCH  120
RVIAENGIGG YSRGVKLKRA LLELEGVKIP E                                151

SEQ ID NO: 11             moltype = AA  length = 156
FEATURE                   Location/Qualifiers
source                    1..156
                          mol_type = protein
                          organism = Sulfolobus tokodaii
SEQUENCE: 11
MIVYGLYKSP FGPITVAKNE KGFVMLDFCD CAERSSLDND YFTDFFYKLD LYFEGKKVDL  60
TEPVDFKPFN EFRIRVFKEV MRIKWGEVRT YKQVADAVKT SPRAVGTALS KNNVLLIIPC  120
HRVIGEKSLG GYSRGVELKR KLLELEGIDV AKFIEK                           156

SEQ ID NO: 12             moltype = AA  length = 174
FEATURE                   Location/Qualifiers
source                    1..174
                          mol_type = protein
                          organism = Thermococcus kodakarensis
SEQUENCE: 12
MLSVEKFRVG ERVVWIGVIF SGRVQGIAFA FDRGTLMKRI HDLAEHLGKR GVSISLDVQP  60
SDYPEKVFKV LIGELDNASF LRELSFEGVT PFEKKVYEWL TKNVKRGSVI TYGDLAKALN  120
TSPRAVGGAM KRNPYPIVVP CHRVVAHDGI GYYSSGIEEK KFLLEIEGVK EWTS        174

SEQ ID NO: 13             moltype = AA  length = 174
FEATURE                   Location/Qualifiers
source                    1..174
                          mol_type = protein
                          organism = Thermotoga neapolitana
SEQUENCE: 13
MRDRFFHRSD RSQIYTPFME SSSNEPVIIL SGGGDFFMKD LPGNISVRVE NGKVVEIKLG  60
SDESNCPPKV KKELEEYFSG KRKEFSFPVE IRGTSFQKKV WEEVRKIPYG ETRTYREIAE  120
KLNTSPRAVG QALAKNPLPL YIPCHRVVSK RGLGGFSAGL EWKRFLIDLE RGSR        174

SEQ ID NO: 14             moltype = AA  length = 207
FEATURE                   Location/Qualifiers
source                    1..207
                          mol_type = protein
                          organism = synthetic construct
SEQUENCE: 14
MDKDCEMKRT TLDSPLGKLE LSGCEQGLHE IKLLGKGTSA ADAVEVPAPA AVLGGPEPLM  60
QCTAWLNAYF HQPEAIEEFP VPALHHPVFQ QESFTRQVLW KLLKVVKFGE VISYQQLAAL  120
AGNPKAARAV GGAMRGNPIP IVVPCHRVIG RNGTMTGYAG GLAVKEWLLA HEGHRLGKPG  180
LGGSSGLAGA WLKGAGATSG SPPAGRN                                     207

SEQ ID NO: 15             moltype = AA  length = 171
FEATURE                   Location/Qualifiers
```

-continued

```
source                  1..171
                        mol_type = protein
                        organism = synthetic construct
SEQUENCE: 15
MLRLLEEKIA TPLGPLWVIC DEQFRLRAVE WEEYSERMVQ LLDIHYRKEG YERISATNPG  60
GLSDKLREYF AGNLSIIDTL PTATGGTPFQ REVWKTLRTI PCGQVMHYGQ LAEQLGRPGA  120
ARAVGAANGS NPIPIVVPCH RVIGRNGTMT GYAGGVQRKE WLLRHEGYLL L           171

SEQ ID NO: 16           moltype = AA  length = 207
FEATURE                 Location/Qualifiers
source                  1..207
                        mol_type = protein
                        organism = synthetic construct
SEQUENCE: 16
MDKDCEMKRT TLDSPLGKLE LSGCEQGLHE IKLLGKGTSA ADAVEVPAPA AVLGGPEPLM  60
QCTAWLNAYF HQPEAIEEFP VPALHHPVFQ QESFTRQVLW KLLKVVKFGE VISYQQLAAL  120
AGNPKAARAV GGAMRGNPVP ILIPCHRVVC SSGAVGGYEG GLAVKEWLLA HEGHRLGKPG  180
LGGSSGLAGA WLKGAGATSG SPPAGRN                                     207

SEQ ID NO: 17           moltype = AA  length = 207
FEATURE                 Location/Qualifiers
source                  1..207
                        mol_type = protein
                        organism = synthetic construct
SEQUENCE: 17
MDKDCEMKRT TLDSPLGKLE LSGCEQGLHE IKLLGKGTSA ADAVEVPAPA AVLGGPEPLM  60
QCTAWLNAYF HQPEAIEEFP VPALHHPVFQ QESFTRQVLW KLLKVVKFGE VISYQQLAAL  120
AGNPKAARAV GGAMRGNPVP ILIPCHRVVC SSGAVGGYEA GLAVKEWLLA HEGHRLGKPG  180
LGGSSGLAGA WLKGAGATSG SPPAGRN                                     207

SEQ ID NO: 18           moltype = AA  length = 207
FEATURE                 Location/Qualifiers
source                  1..207
                        mol_type = protein
                        organism = synthetic construct
SEQUENCE: 18
MDKDCEMKRT TLDSPLGKLE LSGCEQGLHE IKLLGKGTSA ADAVEVPAPA AVLGGPEPLM  60
QCTAWLNAYF HQPEAIEEFP VPALHHPVFQ QESFTRQVLW KLLKVVKFGE VISYQQLAAL  120
AGNPKAARAV VHALRGNPVP ILIPCHRVVC SSGAVGGYEG GLAVKEWLLA HEGHRLGKPG  180
LGGSSGLAGA WLKGAGATSG SPPAGRN                                     207

SEQ ID NO: 19           moltype = AA  length = 207
FEATURE                 Location/Qualifiers
source                  1..207
                        mol_type = protein
                        organism = synthetic construct
SEQUENCE: 19
MDKDCEMKRT TLDSPLGKLE LSGCEQGLHE IKLLGKGTSA ADAVEVPAPA AVLGGPEPLM  60
QCTAWLNAYF HQPEAIEEFP VPALHHPVFQ QESFTRQVLW KLLKVVKFGE VISYQQLAAL  120
AGNPKAARAV KTALSGNPVP ILIPCHRVVC SSGAVGGYEG GLAVKEWLLA HEGHRLGKPG  180
LGGSSGLAGA WLKGAGATSG SPPAGRN                                     207

SEQ ID NO: 20           moltype = AA  length = 207
FEATURE                 Location/Qualifiers
source                  1..207
                        mol_type = protein
                        organism = synthetic construct
SEQUENCE: 20
MDKDCEMKRT TLDSPLGKLE LSGCEQGLHE IKLLGKGTSA ADAVEVPAPA AVLGGPEPLM  60
QCTAWLNAYF HQPEAIEEFP VPALHHPVFQ QESFTRQVLW KLLKVVKFGE VISYQQLAAL  120
AGNPKAARAV GGAMRGNPVP ILIPCHRVVY SRGSGGTYSG GLAVREWLLA HEGHRLGKPG  180
LGGSSGLAGA WLKGAGATSG SPPAGRN                                     207

SEQ ID NO: 21           moltype = AA  length = 207
FEATURE                 Location/Qualifiers
source                  1..207
                        mol_type = protein
                        organism = synthetic construct
SEQUENCE: 21
MDKDCEMKRT TLDSPLGKLE LSGCEQGLHE IKLLGKGTSA ADAVEVPAPA AVLGGPEPLM  60
QCTAWLNAYF HQPEAIEEFP VPALHHPVFQ QESFTRQVLW KLLKVVKFGE VISYQQLAAL  120
AGNPKAARAV GGAMRGNPIS IVVPCHRVIG RNGTMTGYAG GVQRKEWLLA HEGHRLGKPG  180
LGGSSGLAGA WLKGAGATSG SPPAGRN                                     207

SEQ ID NO: 22           moltype = AA  length = 207
FEATURE                 Location/Qualifiers
source                  1..207
                        mol_type = protein
                        organism = synthetic construct
```

```
SEQUENCE: 22
MDKDCEMKRT TLDSPLGKLE LSGCEQGLHE IKLLGKGTSA ADAVEVPAPA AVLGGPEPLM  60
QCTAWLNAYF HQPEAIEEFP VPALHHPVFQ QESFTRQVLW KLLKVVKFGE VISYQQLAAL  120
AGNPKAARAV GGAMRGNPIS IVVPCHRVIG RNGTMTGYAG GVQRKEWLLA HEGHRLGKPG  180
LGGSSGLAGA WLKGAGATSG SPPAGRN                                     207

SEQ ID NO: 23          moltype = AA  length = 207
FEATURE                Location/Qualifiers
source                 1..207
                       mol_type = protein
                       organism = synthetic construct
SEQUENCE: 23
MDKDCEMKRT TLDSPLGKLE LSGCEQGLHE IKLLGKGTSA ADAVEVPAPA AVLGGPEPLM  60
QCTAWLNAYF HQPEAIEEFP VPALHHPVFQ QESFTRQVLW KLLKVVKFGE VISYQQLAAL  120
AGNPKAARAV GGAMRGNPVP ILIPCHRVIG RNGTMTGYSG GLAVKEWLLA HEGHRLGKPG  180
LGGSSGLAGA WLKGAGATSG SPPAGRN                                     207

SEQ ID NO: 24          moltype = DNA  length = 30
FEATURE                Location/Qualifiers
source                 1..30
                       mol_type = other DNA
                       organism = synthetic construct
SEQUENCE: 24
ttttttttt tttttgccgc gtttcgcggc                                   30

SEQ ID NO: 25          moltype = DNA  length = 30
FEATURE                Location/Qualifiers
source                 1..30
                       mol_type = other DNA
                       organism = synthetic construct
modified_base          28
                       mod_base = OTHER
                       note = O6-methylguanosine
SEQUENCE: 25
ttttttttt tttttgccgc gtttcgcggc                                   30

SEQ ID NO: 26          moltype = DNA  length = 50
FEATURE                Location/Qualifiers
source                 1..50
                       mol_type = other DNA
                       organism = synthetic construct
SEQUENCE: 26
aaccgaccaa gctacggttc agaaaattcg cgatgcaatt cgcgatcagc            50

SEQ ID NO: 27          moltype = DNA  length = 45
FEATURE                Location/Qualifiers
source                 1..45
                       mol_type = other DNA
                       organism = synthetic construct
SEQUENCE: 27
ctgacagaga tgatgaagtc acatgagaca tgaactgagt ctttt                 45

SEQ ID NO: 28          moltype = DNA  length = 40
FEATURE                Location/Qualifiers
source                 1..40
                       mol_type = other DNA
                       organism = synthetic construct
SEQUENCE: 28
gggcgggcgg cggggttttt ccccgccgcc cgcccttttt                       40

SEQ ID NO: 29          moltype = DNA  length = 41
FEATURE                Location/Qualifiers
source                 1..41
                       mol_type = other DNA
                       organism = synthetic construct
SEQUENCE: 29
ctgacagaga tgatgaagtc acatgagaca tgaactgagt c                     41

SEQ ID NO: 30          moltype = DNA  length = 30
FEATURE                Location/Qualifiers
source                 1..30
                       mol_type = other DNA
                       organism = synthetic construct
SEQUENCE: 30
ttttttttt tttttgccgc gtttcgcggc                                   30

SEQ ID NO: 31          moltype = AA  length = 6
FEATURE                Location/Qualifiers
source                 1..6
```

-continued

```
                         mol_type = protein
                         organism = synthetic construct
SEQUENCE: 31
HHHHHH                                                              6

SEQ ID NO: 32            moltype = DNA  length = 35
FEATURE                  Location/Qualifiers
source                   1..35
                         mol_type = other DNA
                         organism = synthetic construct
SEQUENCE: 32
ttttttttt ttttttttt ttttttttt ttttt                                 35

SEQ ID NO: 33            moltype = DNA  length = 30
FEATURE                  Location/Qualifiers
source                   1..30
                         mol_type = other DNA
                         organism = synthetic construct
SEQUENCE: 33
cccccccccc cccccccccc cccccccccc                                    30
```